(12) United States Patent
Banner et al.

(10) Patent No.: US 8,524,710 B2
(45) Date of Patent: Sep. 3, 2013

(54) PYRROLIDINE DERIVATIVES

(75) Inventors: David Banner, Basel (CH); Uwe Grether, Efringen-Kirchen (DE); Wolfgang Haap, Loerrach (DE); Holger Kuehne, Loerrach (DE); Harald Mauser, Birsfelden (CH); Jean-Marc Plancher, Hagenthal-le-Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 182 days.

(21) Appl. No.: 13/279,364

(22) Filed: Oct. 24, 2011

(65) Prior Publication Data

US 2012/0115843 A1    May 10, 2012

(30) Foreign Application Priority Data

Nov. 5, 2010  (EP) ..................... 10190239

(51) Int. Cl.
- *C07D 401/04* (2006.01)
- *C07D 487/04* (2006.01)
- *A61K 31/506* (2006.01)

(52) U.S. Cl.
USPC .............. 514/235.8; 514/252.19; 514/253.09; 514/255.05; 514/256; 514/249; 514/258.1; 514/265.1; 514/343; 544/120; 544/122; 544/253; 544/280; 544/295; 544/326; 544/336; 546/278.4

(58) Field of Classification Search
USPC ................ 544/120, 122, 253, 280, 295, 326, 544/336; 546/278.4; 514/235.8, 249, 252.19, 514/253.09, 255.05, 256, 258.1, 265.1, 343
See application file for complete search history.

(56) References Cited

FOREIGN PATENT DOCUMENTS

| WO | 01/47886 | 7/2005 |
|---|---|---|
| WO | 2010/121918 | 10/2010 |

OTHER PUBLICATIONS

Burns-Kurtis et al., "Cardiovascular Research" 62(3):610-620 ( 2004).
Wang et al., "J. Biol. Chem." 281(9):6020-6029 ( 2006).
Burden et al., "Clin. Cancer Res." 15(19):6042-6051 ( 2009).
Funkelstein et al., "Journal of Biological Chemistry" 283(51):35652-35659 ( 2008).
Roberts, R., "Drug News & Perspectives" 18(10):605-614 ( 2005).
Kitamoto et al., "Circulation" 115(15):2065-2075 ( 2007).
Shi et al., "Circulation Research" 92(5):493-500 ( 2003).
Denooijer et al., "Arteriosclerosis Thromb. Vascular Biology" 29(2):188-194 ( 2009).
Hsing et al., "Immunological Reviews" 207:229-241 ( 2005).
Rodgers et al., "Arteriosclerosis Thromb. Vascular Biology" 26(4):851-856 ( 2006).
Sukhova et al., "Journal of Clinical Investigation" 102(3):576-583 ( 1998).
Driessen et al., "Journal of Cellular Biology" 147(4):775-790 ( 1999).
Rudensky et al., "Ernst Schering Research Foundation Workshop" 56:81-95 ( 2006).
Sever et al., "J. Clin. Invest." 117(8):2095-2104 ( 2007).
Liu et al., "Atherosclerosis" 186(2):411-419 ( 2006).
Funkelstein et al., "Journal of Neurochemistry" 106:384-391 ( 2008).
"International Search Report PCT/EP2011/069219 mailed Nov. 22, 2011".
Aikawa et al., "Circulation" 119(13):1785-1794 ( 2009).
Bromme, D., "Current Protocols in Protein Science" ((Suppl. 21)),:21.2.1-21.2.14 ( 2000).
Cheng et al., "American Journal of Pathology" 164(1):243-251 ( 2004).
Williams et al., "Pulmonary Pharmacology & Therapeutics" 22(1):27-32 ( 2009).
Sukhova et al., "Journal of Clinical Investigation" 111(6):897-906 ( 2003).

*Primary Examiner* — Deepak Rao

(57) ABSTRACT

The invention relates to a compound of formula (I)

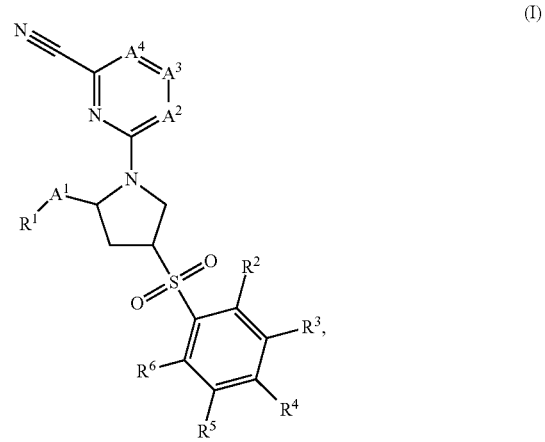

wherein $A^1$ to $A^4$ and $R^1$ to $R^6$ are defined as in the description and in the claims. The compound of formula (I) can be used, for example, as inhibitors of the cysteine protease cathepsin.

32 Claims, No Drawings

PYRROLIDINE DERIVATIVES

PRIORITY TO RELATED APPLICATION(S)

This application claims the benefit of European Patent Application No. 10190239.3, filed Nov. 5, 2010, which is hereby incorporated by reference in its entirety.

FIELD OF THE INVENTION

The present invention relates to organic compounds useful for therapy and/or prophylaxis in a mammal, and in particular to compounds that are preferential inhibitors of the cysteine protease cathepsin, in particular of the cysteine protease cathepsin S or L.

BACKGROUND OF THE INVENTION

The compounds of the invention are preferential inhibitors of the cysteine protease Cathepsin (Cat), in particular Cathepsin S or Cathepsin L and are therefore useful to treat metabolic diseases like diabetes, atherosclerosis, abdominal aortic aneurysm, peripheral arterial disease, cancer, reduction of cardiovascular events in chronic kidney disease, glomerulonephritis, age related macular degeneration, diabetic nephropathy and diabetic retinopathy. In addition, immune mediated diseases like rheumatoid arthritis, crohn's disease, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells. (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500;

Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

Cathepsin L shows a broader expression profile than cathepsin S and there are also data which suggest a role of cathepsin L in atherosclerosis, e.g. LDLrec & Cat L deficient mice show a reduced atherosclerotic phenotype (Kitamoto, S., et al. (2007), 'Cathepsin L deficiency reduces diet-induced atherosclerosis in low-density lipoprotein receptor-knockout mice', Circulation, 115 (15), 2065-75). In addition, Cat L was suggested to be involved in metabolic syndrome as it controls adipogenesis and peripheral glucose tolerance. In renal disease Cathepsin L is described to regulate podocyte function by proteolytically processing dynamin and thereby proteinuria (Sever, S., et al. (2007), 'Proteolytic processing of dynamin by cytoplasmic cathepsin L is a mechanism for proteinuric kidney disease', J Clin Invest, 117 (8), 2095-104).

Tissue remodelling, extracellular matrix degradation, the generation of active neuropeptides and roles in antigen presentation in thymic epithelial cells are cellular activities described for Cathepsin L (Funkelstein et al. 2008; Rudensky and Beers 2006).

SUMMARY OF THE INVENTION

The present invention relates to a compound of formula (I)

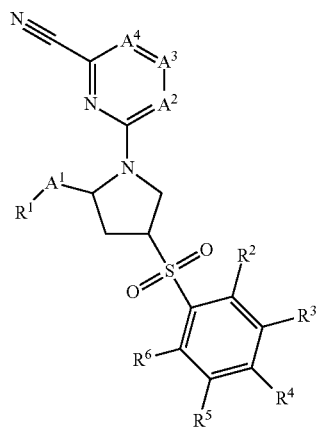

(I)

wherein $R^1$ is selected from the group consisting of hydrogen, alkyl, morpholinyl, haloalkylamino, alkyloxadiazolyl, hydroxyl, halopyrrolidinyl, azetidinyl, alkylamino, amino, cyanoalkylamino, halophenylalkylamino and cyanocycloalkylamino;

$R^2$, $R^3$, $R^4$, $R^5$ and $R^6$ are each independently selected from the group consisting of hydrogen, alkyl, haloalkyl, hydroxyalkyl, alkoxy, haloalkyloxy, halogen, hydroxyl, cyanopyrazinyloxy, pyrazolyl, alkylpyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxomorpholinyl, oxo-pyridinyl, 2-oxo-2H-pyrazinyl, difluoropiperidinyl, haloalkylpiperidinyl, piperidinylalkoxy, oxetanyloxy, alkylpyrazolyl, halopyridinyl, alkylpyridinyl, cycloalkyl, cycloalkylalkyl, halophenyl, alkylcarbonylaminocycloalkylalkyl, haloalkylpiperazinyl, alkylamino, alkoxyalkylpiperazinyl, cycloalkylpiperazinyl, hexahydropyrrolo[1,2-a]pyrazinyl, 5,6-dihydro-8H-[1,2,4]triazolo[4,3-a]pyrazin-7-yl, alkylimidazolyl, azetidinyl, cycloalkylpiperazinyl, alkylimidazolyl, alkoxyalkoxy, imidazo[4,5-c]pyridinyl, alkylpiperazinyl, hexahydro-pyrrolo[1,2-a]pyrazinyl, haloazetidinyl, pyrimindinyl and alkenyloxy;

$A^1$ is —$CH_2$—, carbonyl, —C(O)O— or absent;
$A^2$ is nitrogen or $CR^7$;
$A^3$ is nitrogen or $CR^8$;
$A^4$ is nitrogen or $CR^9$;
$R^7$ is selected from the group consisting of hydrogen, alkyl, haloalkyl, halogen, hydroxyl, haloalkylaminocarbonyl; halophenylalkylaminocarbonyl, phenylcycloalkylaminocarbonyl, haloalkylphenylalkylaminocarbonyl, halophenylcycloalkylaminocarbonyl and halophenylcycloalkylalkylaminocarbonyl;
$R^8$ is selected from the group consisting of hydrogen, alkyl, haloalkyl, halogen and hydroxyl;
or $R^7$ and $R^8$ together with the carbon atom to which they are attached form cycloalkyl or substituted pyrrolidine, wherein substituted pyrrolidine is pyrrolidine N-substituted with haloalkyl or formyl;
$R^9$ is selected from the group consisting of hydrogen, alkyl, haloalkyl, halogen and nitro;
or $R^8$ and $R^9$ together with the carbon atom to which they are attached form cycloalkyl;
or a pharmaceutically acceptable salt thereof.

The present invention also relates to a pharmaceutical composition comprising a compound as described above and a pharmaceutically inert carrier.

DETAILED DESCRIPTION OF THE INVENTION

In the present description the term "alkyl", alone or in combination, signifies a straight-chain or branched-chain hydrocarbon group with 1 to 8 carbon atoms. In an embodiment, it is a straight or branched-chain hydrocarbon group with 1 to 6 carbon atoms. In another embodiment, it is a straight or branched-chain hydrocarbon group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls. In an embodiment, the alkyl is methyl, ethyl, propyl, isopropyl, isobutyl or tert.-butyl.

The term "cycloalkyl", alone or in combination, signifies a hydrocarbon ring with 3 to 8 carbon atoms. In an embodiment, it is a hydrocarbon ring with 3 to 6 carbon atoms. Examples of $C_3$-$C_8$ cycloalkyl are cyclopropyl, cyclobutyl, cyclopentyl, cyclohexyl, cycloheptyl and cyclooctyl. In an embodiment, the cycloalkyl is cyclopropyl, cyclobutyl, cyclopentyl or cyclohexyl. In another embodiment, it is cyclopropyl or cyclobutyl. In another embodiment, it is cyclopropyl.

The term "alkoxy", alone or in combination, signifies a group of the formula alkyl-O— in which the term "alkyl" has the previously given significance. Examples of alkoxy include methoxy, ethoxy, n-propoxy, isopropoxy, n-butoxy, isobutoxy, sec. butoxy and tert.butoxy. In an embodiment, alkoxy is methoxy, ethoxy, propoxy or isopropoxy.

The term "cycloalkyloxy", alone or in combination, signifies a group of the formula cycloalkyl-O— in which the term "cycloalkyl" has the previously given significance, such as cyclobutyloxy, cyclopentyloxy or cyclohexyloxy.

The term "phenyloxy", alone or in combination, signifies a phenyl-O— group.

The term "oxy", alone or in combination, signifies the —O— group.

The term "halogen" or "halo", alone or in combination, signifies fluorine, chlorine, bromine or iodine. In an embodiment, the halogen or halo is fluorine, chlorine or bromine. In another embodiment, it is fluorine or chlorine.

The terms "haloalkyl", "halocycloalkyl" and "haloalkoxy", alone or in combination, denote, respectively, an alkyl group, a cycloalkyl group and an alkoxy group substituted with at least one halogen. In an embodiment, substitution is with one to five halogens. In another embodiment, it is with one to three halogens. Fluoroalkyl is an alkyl group substituted with at least one fluorine atom, In an embodiment, substitution is with one to five fluorine atoms. In another embodiment, it is with one to three halogens. Examples of haloalkyl are trifluoromethyl, trifluoroethyl and trifluoropropyl.

The terms "halophenyl", "halopyrrolidinyl", "halopyridinyl" and "haloazetidinyl", alone or in combination, denote, respectively, a phenyl group, a pyrrolidinyl group, a pyridinyl group and an azetidinyl group substituted with at least one halogen. In an embodiment, substitution is with one to three halogens.

The terms "hydroxyl" and "hydroxy", alone or in combination, signify the —OH group.

The term "carbonyl", alone or in combination, signifies the —C(O)— group.

The term "carboxy", alone or in combination, signifies the —COOH group.

The term "amino", alone or in combination, signifies the primary amino group (—NH$_2$), the secondary amino group (—NH—), or the tertiary amino group (—N—).

The term "formyl", alone or in combination, signifies the group HC(O)—.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins. The compound of formula (I) can also be present in the form of zwitterions. In a particular embodiment, the pharmaceutically acceptable salts of compounds of formula (I) are the salts of hydrochloric acid, hydrobromic acid, sulfuric acid, phosphoric acid and methanesulfonic acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The present invention relates to a compound of formula (I)

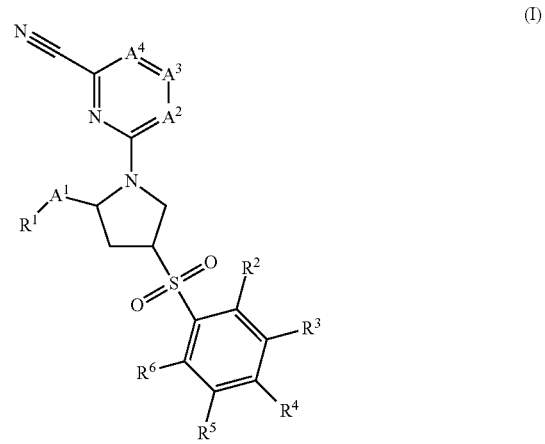

wherein $R^1$ is selected from the group consisting of hydrogen, alkyl, morpholinyl, haloalkylamino, alkyloxadiazolyl, hydroxyl, halopyrrolidinyl, azetidinyl, alkylamino, amino, cyanoalkylamino, halophenylalkylamino and cyanocycloalkylamino;

$R^2$, $R^3$, $R^4$, $R^5$ and $R^6$ are each independently selected from the group consisting of hydrogen, alkyl, haloalkyl, hydroxyalkyl, alkoxy, haloalkyloxy, halogen, hydroxyl, cyanopyrazinyloxy, pyrazolyl, alkylpyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, haloalkylpiperidinyl, piperidinylalkoxy, oxetanyloxy, alkylpyrazolyl, halopyridinyl, alkylpyridinyl, cycloalkyl, cycloalkylalkyl, halophenyl, alkylcarbonylaminocycloalkylalkyl, haloalkylpiperazinyl, alkylamino, alkoxyalkylpiperazinyl, cycloalkylpiperazinyl, hexahydropyrrolo[1,2-a]pyrazinyl, 5,6-dihydro-8H-[1,2,4]triazolo[4,3-a]pyrazin-7-yl, alkylimidazolyl, azetidinyl, cycloalkylpiperazinyl, alkylimidazolyl, alkoxyalkoxy, imidazo[4,5-c]pyridinyl, alkylpiperazinyl, hexahydro-pyrrolo[1,2-a]pyrazinyl, haloazetidinyl, pyrimindinyl and alkenyloxy;

$A^1$ is —CH$_2$—, carbonyl, —C(O)O— or absent;

$A^2$ is nitrogen or CR$^7$;

$A^3$ is nitrogen or CR$^8$;

$A^4$ is nitrogen or CR$^9$;

$R^7$ is selected from the group consisting of hydrogen, alkyl, haloalkyl, halogen, hydroxyl, haloalkylaminocarbonyl; halophenylalkylaminocarbonyl, phenylcycloalkylaminocarbonyl, haloalkylphenylalkylaminocarbonyl, halophenylcycloalkylaminocarbonyl and halophenylcycloalkylalkylaminocarbonyl;

$R^8$ is selected from the group consisting of hydrogen, alkyl, haloalkyl, halogen and hydroxyl;

or $R^7$ and $R^8$ together with the carbon atom to which they are attached form cycloalkyl or substituted pyrrolidine, wherein substituted pyrrolidine is pyrrolidine N-substituted with haloalkyl or formyl;

$R^9$ is selected from the group consisting of hydrogen, alkyl, haloalkyl, halogen and nitro;

or $R^8$ and $R^9$ together with the carbon atom to which they are attached form cycloalkyl;

or a pharmaceutically acceptable salt thereof.

In the definition of $R^1$, alkyl is for example methyl or ethyl. In the definition of $R^1$, haloalkylamino is for example trifluoroethylamino or trifluoropropylamino. In the definition of $R^1$, alkyloxadiazolyl is for example dimethyloxadiazolyl. In the definition of $R^1$, halopyrrolidinyl is for example difluoropyrrolidinyl. In the definition of $R^1$, alkylamino is for example ethylamino, propylamino or dimethylamino. In the definition of $R^1$, cyanoalkylamino is for example cyanomethylamino. In the definition of $R^1$, halophenylalkylamino is for example fluorophenylmethylamino. In the definition of $R^1$, cyanocycloalkylamino is for example cyanocyclopropylamino.

The invention also relates to a compound of formula (I) wherein $R^1$ is selected from the group consisting of hydrogen, methyl, ethyl, morpholinyl, trifluoroethylamino, trifluoropropylamino, dimethyloxadiazolyl, hydroxyl, difluoropyrrolidinyl, azetidinyl, ethylamino, propylamino, dimethylamino, amino, cyanomethylamino, fluorophenylmethylamino and cyanocyclopropylamino.

A particular compound according to the invention is a compound of formula (I) wherein $R^1$ is hydrogen or amino.

In an embodiment, the compound is a compound according to formula (I), wherein $R^7$ is selected from the group consisting of hydrogen, alkyl, haloalkyl, halogen and hydroxyl;

$R^8$ is selected from the group consisting of hydrogen, alkyl, haloalkyl, halogen and hydroxyl;

or $R^7$ and $R^8$ together with the carbon atom to which they are attached form cycloalkyl;

$R^9$ is selected from the group consisting of hydrogen, alkyl, haloalkyl and halogen;

or $R^8$ and $R^9$ together with the carbon atom to which they are attached form cycloalkyl.

Another particular compound according to the invention is a compound of formula (I) wherein $R^2$, $R^3$, $R^4$, $R^5$ and $R^6$ are each independently selected from the group consisting of hydrogen, halogen, hydroxyl, haloalkyl, cyanopyrazinyloxy, alkylpiperazinyl, hexahydro-pyrrolo[1,2-a]pyrazinyl, haloalkyloxy, pyrazolyl, cycloalkylpiperazinyl, imidazolyl and alkoxyalkoxy.

A further particular compound according to the invention is a compound of formula (I) wherein $R^2$ and $R^6$ are each independently selected from the group consisting of hydrogen, halogen and haloalkyl.

A compound of formula (I) wherein one of $R^2$ and $R^6$ is halogen or haloalkyl and the other one is hydrogen is another particular embodiment of the invention.

A compound of formula (I) wherein one of $R^2$ and $R^6$ is chloro or trifluoromethyl and the other one is hydrogen is another particular embodiment of the invention.

Still another particular compound of the invention is a compound of formula (I) wherein $R^3$ and $R^5$ are each independently selected from the group consisting of hydrogen, halogen and haloalkyl.

Furthermore, a particular compound of the invention is a compound of formula (I) wherein $R^3$ and $R^5$ are each independently selected from the group consisting of hydrogen, chloro and trifluoromethyl.

Moreover, a particular compound of the invention is also a compound of formula (I) wherein $R^3$ and $R^5$ are both hydrogen.

A compound of formula (I) wherein $R^4$ is selected from the group consisting of hydrogen, hydroxyl, halogen, cyanopyrazinyloxy, alkylpiperazinyl, hexahydropyrrolo[1,2-a]pyrazinyl, haloalkoxy, pyrazolyl, cycloalkylpiperazinyl, imidazolyl and alkoxyalkoxy is a particular embodiment of the invention.

In addition, a compound of formula (I) wherein $R^4$ is selected from the group consisting of hydrogen, halogen, alkylpiperazinyl, hexahydropyrrolo[1,2-a]pyrazinyl, haloalkoxy, pyrazolyl, cycloalkylpiperazinyl and alkoxyalkoxy is another particular embodiment of the invention.

Furthermore, a compound of formula (I) wherein $R^4$ is selected from the group consisting of hydrogen, halogen, methylpiperazinyl, tert-butylpiperazinyl, hexahydropyrrolo[1,2-a]pyrazinyl, trifluoroethyloxy, trifluoropropyloxy, pyrazolyl, cyclopropylpiperazinyl and methoxyethoxy is still another particular embodiment of the invention.

The invention is also directed in particular to a compound of formula (I) wherein $A^1$ is absent or carbonyl.

The invention further relates in particular to a compound of formula (I) wherein $A^2$ is CR$^7$.

Moreover, the invention is particularly concerned with a compound of formula (I) wherein $A^3$ is CR$^8$.

When $R^7$ and $R^8$ together with the carbon atom to which they are attached form cycloalkyl, a particular cycloalkyl is cyclopentyl.

A compound of formula (I) wherein $A^4$ is nitrogen is a further particular object of the invention.

A compound of formula (I) wherein $R^7$ is hydrogen is another particular object of the invention.

A compound of formula (I) wherein $R^8$ is hydrogen, alkyl or haloalkyl is also another particular object of the invention.

The invention also relates in particular to a compound of formula (I) wherein $R^8$ is trifluoromethyl.

The invention also relates in particular to a compound of formula (I) wherein $R^9$ is hydrogen.

When $R^8$ and $R^9$ together with the carbon atom to which they are attached form cycloalkyl, a particular cycloalkyl is cyclopentyl.

Particular compounds of formula (I) can be selected from the group consisting of:

6-[(2S,4S)-4-(2-Chloro-benzenesulfonyl)-2-(morpholine-4-carbonyl)-pyrrolidin-1-yl]-pyrazine-2-carbonitrile;

(2S,4S)-4-(2-Chloro-benzenesulfonyl)-1-(6-cyano-pyrazin-2-yl)-pyrrolidine-2-carboxylic acid methyl ester;

6-[3-(4-Hydroxy-benzenesulfonyl)-pyrrolidin-1-yl]-pyrazine-2-carbonitrile;
6-[3-({4-[(6-cyanopyrazin-2-yl)oxy]phenyl}sulfonyl)pyrrolidin-1-yl]pyrazine-2-carbonitrile;
(2S,4S)-4-(2-chloro-benzenesulfonyl)-1-(6-cyano-pyrazin-2-yl)-pyrrolidine-2-carboxylic acid;
(2S,4S)-4-(2-Chloro-benzenesulfonyl)-1-(6-cyano-pyrazin-2-yl)-pyrrolidine-2-carboxylic acid (2,2,2-trifluoroethyl)-amide;
(2R,4S)-4-(2-Chloro-benzenesulfonyl)-1-(6-cyano-pyrazin-2-yl)-pyrrolidine-2-carboxylic acid ethyl ester;
6-[(S)-3-(2-Chloro-benzenesulfonyl)-pyrrolidin-1-yl]-pyridine-2-carbonitrile;
6-[(S)-3-(2-Chloro-benzenesulfonyl)-pyrrolidin-1-yl]-pyrazine-2-carbonitrile;
6-[(2R,4S)-4-(2-Chloro-benzenesulfonyl)-2-(morpholine-4-carbonyl)-pyrrolidin-1-yl]-pyrazine-2-carbonitrile;
(2R,4S)-4-(2-Chloro-benzenesulfonyl)-1-(6-cyano-pyrazin-2-yl)-pyrrolidine-2-carboxylic acid (2,2,2-trifluoroethyl)-amide;
4-[(S)-3-(2-Chloro-benzenesulfonyl)-pyrrolidin-1-yl]-pyrimidine-2-carbonitrile;
4-[(2R,4S)-4-(2-Chloro-benzenesulfonyl)-2-(5-methyl-[1,3,4]oxadiazol-2-yl)-pyrrolidin-1-yl]-pyrimidine-2-carbonitrile;
4-[(S)-3-(2-Trifluoromethyl-benzenesulfonyl)-pyrrolidin-1-yl]-pyrimidine-2-carbonitrile;
4-[(2R,4S)-2-Hydroxymethyl-4-(2-trifluoromethyl-benzenesulfonyl)-pyrrolidin-1-yl]-pyrimidine-2-carbonitrile;
4-Methyl-6-[(S)-3-(2-trifluoromethyl-benzenesulfonyl)-pyrrolidin-1-yl]-pyrimidine-2-carbonitrile;
5-Trifluoromethyl-4-[(S)-3-(2-trifluoromethyl-benzenesulfonyl)-pyrrolidin-1-yl]-pyrimidine-2-carbonitrile;
5-Fluoro-4-[(S)-3-(2-trifluoromethyl-benzenesulfonyl)-pyrrolidin-1-yl]-pyrimidine-2-carbonitrile;
5-Hydroxy-4-[(S)-3-(2-trifluoromethyl-benzenesulfonyl)-pyrrolidin-1-yl]-pyrimidine-2-carbonitrile;
4-[(2R,4S)-2-Morpholin-4-ylmethyl-4-(2-trifluoromethyl-benzenesulfonyl)-pyrrolidin-1-yl]-pyrimidine-2-carbonitrile;
2-[(2R,4S)-2-Morpholin-4-ylmethyl-4-(2-trifluoromethyl-benzenesulfonyl)-pyrrolidin-1-yl]-pyrimidine-4-carbonitrile;
4-[(2R,4S)-2-(3,3-Difluoro-pyrrolidin-1-ylmethyl)-4-(2-trifluoromethyl-benzenesulfonyl)-pyrrolidin-1-yl]-pyrimidine-2-carbonitrile;
4-[(S)-3-(2,3-Dichloro-benzenesulfonyl)-pyrrolidin-1-yl]-pyrimidine-2-carbonitrile;
4-[(R)-3-(2-Bromo-benzenesulfonyl)-pyrrolidin-1-yl]-pyrimidine-2-carbonitrile;
4-[(S)-3-(3-Trifluoromethyl-benzenesulfonyl)-pyrrolidin-1-yl]-pyrimidine-2-carbonitrile;
(2S,4S)-1-(2-Cyano-pyrimidin-4-yl)-4-(2-trifluoromethyl-benzenesulfonyl)-pyrrolidine-2-carboxylic acid (2,2,2-trifluoro-ethyl)-amide;
4-[(2S,4S)-2-(Azetidine-1-carbonyl)-4-(2-trifluoromethyl-benzenesulfonyl)-pyrrolidin-1-yl]-pyrimidine-2-carbonitrile;
(2S,4S)-1-(2-Cyano-pyrimidin-4-yl)-4-(2-trifluoromethyl-benzenesulfonyl)-pyrrolidine-2-carboxylic acid ((S)-2,2,2-trifluoro-1-methyl-ethyl)-amide;
(2S,4S)-1-(2-Cyano-pyrimidin-4-yl)-4-(2-trifluoromethyl-benzenesulfonyl)-pyrrolidine-2-carboxylic acid diethylamide;
(2S,4S)-1-(2-Cyano-pyrimidin-4-yl)-4-(2-trifluoromethyl-benzenesulfonyl)-pyrrolidine-2-carboxylic acid;
(2S,4S)-1-(2-Cyano-pyrimidin-4-yl)-4-(2-trifluoromethyl-benzenesulfonyl)-pyrrolidine-2-carboxylic acid amide;
(2S,4S)-1-(2-Cyano-pyrimidin-4-yl)-4-(2-trifluoromethyl-benzenesulfonyl)-pyrrolidine-2-carboxylic acid ethylamide;
(2S,4S)-1-(2-Cyano-pyrimidin-4-yl)-4-(2-trifluoromethyl-benzenesulfonyl)-pyrrolidine-2-carboxylic acid cyanomethyl-amide;
4-[(2S,4S)-2-(3,3-Difluoro-pyrrolidine-1-carbonyl)-4-(2-trifluoromethyl-benzenesulfonyl)-pyrrolidin-1-yl]-pyrimidine-2-carbonitrile;
(2S,4S)-1-(2-Cyano-pyrimidin-4-yl)-4-(2-trifluoromethyl-benzenesulfonyl)-pyrrolidine-2-carboxylic acid 4-fluorobenzylamide;
(2S,4S)-1-(2-Cyano-pyrimidin-4-yl)-4-(2-trifluoromethyl-benzenesulfonyl)-pyrrolidine-2-carboxylic acid (1-cyanocyclopropyl)-amide;
(2S,4S)-1-(2-Cyano-pyrimidin-4-yl)-4-(2-trifluoromethyl-benzenesulfonyl)-pyrrolidine-2-carboxylic acid isopropylamide;
4-[(S)-3-(2-Trifluoromethyl-benzenesulfonyl)-pyrrolidin-1-yl]-6,7-dihydro-5H-cyclopentapyrimidine-2-carbonitrile;
5-Methyl-4-[(S)-3-(2-trifluoromethyl-benzenesulfonyl)-pyrrolidin-1-yl]-pyrimidine-2-carbonitrile;
4-Trifluoromethyl-6-[(S)-3-(2-trifluoromethyl-benzenesulfonyl)-pyrrolidin-1-yl]-pyrimidine-2-carbonitrile;
(S)-1-(2-Cyano-6-trifluoromethyl-pyrimidin-4-yl)-4-(2-trifluoromethyl-benzenesulfonyl)-pyrrolidine-2-carboxylic acid amide;
4-[(S)-3-(2-Chloro-4-fluoro-benzenesulfonyl)-pyrrolidin-1-yl]-6-trifluoromethyl-pyrimidine-2-carbonitrile;
4-{(S)-3-[2-Chloro-4-(4-methyl-piperazin-1-yl)-benzenesulfonyl]-pyrrolidin-1-yl}-6-trifluoromethyl-pyrimidine-2-carbonitrile;
4-{(S)-3-[4-(4-tert-Butyl-piperazin-1-yl)-2-chloro-benzenesulfonyl]-pyrrolidin-1-yl}-6-trifluoromethyl-pyrimidine-2-carbonitrile;
4-[(S)-3-((S)-2-Chloro-4-hexahydro-pyrrolo[1,2-a]pyrazin-2-yl-benzenesulfonyl)-pyrrolidin-1-yl]-6-trifluoromethyl-pyrimidine-2-carbonitrile;
4-{(S)-3-[2-Chloro-4-((S)-2,2,2-trifluoro-1-methylethoxy)-benzenesulfonyl]-pyrrolidin-1-yl}-6-trifluoromethyl-pyrimidine-2-carbonitrile;
4-[(S)-3-(2-Chloro-4-pyrazol-1-yl-benzenesulfonyl)-pyrrolidin-1-yl]-6-trifluoromethyl-pyrimidine-2-carbonitrile;
4-{(S)-3-[2-Chloro-4-(4-cyclopropyl-piperazin-1-yl)-benzenesulfonyl]-pyrrolidin-1-yl}-6-trifluoromethyl-pyrimidine-2-carbonitrile;
4-{(S)-3-[2-Chloro-4-(2,2,2-trifluoro-ethoxy)-benzenesulfonyl]-pyrrolidin-1-yl}-6-trifluoromethyl-pyrimidine-2-carbonitrile;
4-[(S)-3-(2-Chloro-4-imidazol-1-yl-benzenesulfonyl)-pyrrolidin-1-yl]-6-trifluoromethyl-pyrimidine-2-carbonitrile;
4-{(S)-3-[2-Chloro-4-(2-methoxy-ethoxy)-benzenesulfonyl]-pyrrolidin-1-yl}-6-trifluoromethyl-pyrimidine-2-carbonitrile;
4-[(S)-3-(2-Chloro-4-fluoro-benzenesulfonyl)-pyrrolidin-1-yl]-2-cyano-pyrimidine-5-carboxylic acid (2,2,2-trifluoro-ethyl)-amide;
4-{(S)-3-[4-(4-tert-Butyl-piperazin-1-yl)-2-chloro-benzenesulfonyl]-pyrrolidin-1-yl}-2-cyano-pyrimidine-5-carboxylic acid (2,2,2-trifluoro-ethyl)-amide;
4-{(S)-3-[2-Chloro-4-(2,2,2-trifluoro-ethoxy)-benzenesulfonyl]-pyrrolidin-1-yl}-2-cyano-pyrimidine-5-carboxylic acid (2,2,2-trifluoro-ethyl)-amide;

4-{(S)-3-[2-Chloro-4-(4-cyclopropyl-piperazin-1-yl)-benzenesulfonyl]-pyrrolidin-1-yl}-2-cyano-pyrimidine-5-carboxylic acid (2,2,2-trifluoro-ethyl)-amide;
4-[(S)-3-(2-Chloro-4-imidazol-1-yl-benzenesulfonyl)-pyrrolidin-1-yl]-2-cyano-pyrimidine-5-carboxylic acid (2,2,2-trifluoro-ethyl)-amide;
4-{(S)-3-[4-(4-tert-Butyl-piperazin-1-yl)-2-chloro-benzenesulfonyl]-pyrrolidin-1-yl}-2-cyano-pyrimidine-5-carboxylic acid [2-(4-chloro-phenyl)-propyl]-amide;
4-{(S)-3-[2-Chloro-4-(2,2,2-trifluoro-ethoxy)-benzenesulfonyl]-pyrrolidin-1-yl}-6-(2,2,2-trifluoro-ethyl)-6,7-dihydro-5H-pyrrolo[3,4-d]pyrimidine-2-carbonitrile;
4-[(S)-3-(2-Chloro-4-pyrazol-1-yl-benzenesulfonyl)-pyrrolidin-1-yl]-6-(2,2,2-trifluoro-ethyl)-6,7-dihydro-5H-pyrrolo[3,4-d]pyrimidine-2-carbonitrile;
4-[(S)-3-(2-Chloro-4-pyrazol-1-yl-benzenesulfonyl)-pyrrolidin-1-yl]-6-formyl-6,7-dihydro-5H-pyrrolo[3,4-d]pyrimidine-2-carbonitrile;
6-[(S)-3-((S)-2-Chloro-4-hexahydro-pyrrolo[1,2-a]pyrazin-2-yl-benzenesulfonyl)-pyrrolidin-1-yl]-pyridine-2-carbonitrile; compound with formic acid;
6-[(S)-3-((S)-2-Chloro-4-hexahydro-pyrrolo[1,2-a]pyrazin-2-yl-benzenesulfonyl)-pyrrolidin-1-yl]-pyrazine-2-carbonitrile; compound with formic acid;
2-[(S)-3-((S)-2-Chloro-4-hexahydro-pyrrolo[1,2-a]pyrazin-2-yl-benzenesulfonyl)-pyrrolidin-1-yl]-pyrimidine-4-carbonitrile; compound with formic acid;
6-[3-((S)-2-Chloro-4-hexahydro-pyrrolo[1,2-a]pyrazin-2-yl-benzenesulfonyl)-pyrrolidin-1-yl]-3-nitro-pyridine-2-carbonitrileformic acid;
(S)-6-(3-(2-(trifluoromethyl)phenylsulfonyl)pyrrolidin-1-yl)picolinonitrile;
(S)-2-(3-(2-(trifluoromethyl)phenylsulfonyl)pyrrolidin-1-yl)pyrimidine-4-carbonitrile;
(S)-6-(3-(2-(trifluoromethyl)phenylsulfonyl)pyrrolidin-1-yl)pyrazine-2-carbonitrile;
6-((S)-3-{2-Chloro-4-[4-(2-methoxy-ethyl)-piperazin-1-yl]-benzenesulfonyl}-pyrrolidin-1-yl)-pyrazine-2-carbonitrile;
2-((S)-3-{2-Chloro-4-[4-(2-methoxy-ethyl)-piperazin-1-yl]-benzenesulfonyl}-pyrrolidin-1-yl)-pyrimidine-4-carbonitrile;
6-((S)-3-{2-Chloro-4-[4-(2-methoxy-ethyl)-piperazin-1-yl]-benzenesulfonyl}-pyrrolidin-1-yl)-pyridine-2-carbonitrile;
6-((S)-3-{2-Chloro-4-[4-(2-methoxy-ethyl)-piperazin-1-yl]-benzenesulfonyl}-pyrrolidin-1-yl)-3-nitro-pyridine-2-carbonitrile;
(S)-6-(3-(2-chloro-4-fluorophenylsulfonyl)pyrrolidin-1-yl)picolinonitrile;
(S)-2-(3-(2-chloro-4-fluorophenylsulfonyl)pyrrolidin-1-yl)pyrimidine-4-carbonitrile;
(S)-6-(3-(2-chloro-4-fluorophenylsulfonyl)pyrrolidin-1-yl)pyrazine-2-carbonitrile;
(S)-2-(3-(2-chloro-4-(4-methylpiperazin-1-yl)phenylsulfonyl)pyrrolidin-1-yl)pyrimidine-4-carbonitrile;
(S)-6-(3-(2-chloro-4-(4-methylpiperazin-1-yl)phenylsulfonyl)pyrrolidin-1-yl)pyrazine-2-carbonitrile;
2-Cyano-4-[(S)-3-(2-trifluoromethyl-benzenesulfonyl)-pyrrolidin-1-yl]-pyrimidine-5-carboxylic acid (2-phenyl-cyclopropyl)-amide;
2-Cyano-4-[(S)-3-(2-trifluoromethyl-benzenesulfonyl)-pyrrolidin-1-yl]-pyrimidine-5-carboxylic acid [2-(4-chloro-phenyl)-propyl]-amide;
2-Cyano-4-[(S)-3-(2-trifluoromethyl-benzenesulfonyl)-pyrrolidin-1-yl]-pyrimidine-5-carboxylic acid 4-trifluoromethyl-benzylamide;
2-Cyano-4-[(S)-3-(2,3-dichloro-benzenesulfonyl)-pyrrolidin-1-yl]-pyrimidine-5-carboxylic acid 4-trifluoromethyl-benzylamide;
2-Cyano-4-[(S)-3-(2-trifluoromethyl-benzenesulfonyl)-pyrrolidin-1-yl]-pyrimidine-5-carboxylic acid [1-(4-fluoro-phenyl)-cyclopropyl]-amide;
2-Cyano-4-[(S)-3-(2,3-dichloro-benzenesulfonyl)-pyrrolidin-1-yl]-pyrimidine-5-carboxylic acid [1-(4-fluoro-phenyl)-cyclopropyl]-amide;
2-Cyano-4-[(S)-3-(2-trifluoromethyl-benzenesulfonyl)-pyrrolidin-1-yl]-pyrimidine-5-carboxylic acid (2,2,2-trifluoro-ethyl)-amide;
2-Cyano-4-[(S)-3-(2,3-dichloro-benzenesulfonyl)-pyrrolidin-1-yl]-pyrimidine-5-carboxylic acid (2,2,2-trifluoro-ethyl)-amide;
2-Cyano-4-[(S)-3-(2-trifluoromethyl-benzenesulfonyl)-pyrrolidin-1-yl]-pyrimidine-5-carboxylic acid [2-(4-chloro-phenyl)-propyl]-amide;
2-Cyano-4-[(S)-3-(2-trifluoromethyl-benzenesulfonyl)-pyrrolidin-1-yl]-pyrimidine-5-carboxylic acid [2-(4-chloro-phenyl)-propyl]-amide; and
2-Cyano-4-[(S)-3-(2-trifluoromethyl-benzenesulfonyl)-pyrrolidin-1-yl]-pyrimidine-5-carboxylic acid [1-(4-chloro-phenyl)-cyclopropylmethyl]-amide.

In an embodiment, the compound of formula (I) can be selected from the group consisting of:
4-Trifluoromethyl-6-[(S)-3-(2-trifluoromethyl-benzenesulfonyl)-pyrrolidin-1-yl]-pyrimidine-2-carbonitrile;
(S)-1-(2-Cyano-6-trifluoromethyl-pyrimidin-4-yl)-4-(2-trifluoromethyl-benzenesulfonyl)-pyrrolidine-2-carboxylic acid amide;
4-{(S)-3-[2-Chloro-4-(4-methyl-piperazin-1-yl)-benzenesulfonyl]-pyrrolidin-1-yl}-6-trifluoromethyl-pyrimidine-2-carbonitrile;
4-{(S)-3-[4-(4-tert-Butyl-piperazin-1-yl)-2-chloro-benzenesulfonyl]-pyrrolidin-1-yl}-6-trifluoromethyl-pyrimidine-2-carbonitrile;
4-[(S)-3-((S)-2-Chloro-4-hexahydro-pyrrolo[1,2-a]pyrazin-2-yl-benzenesulfonyl)-pyrrolidin-1-yl]-6-trifluoromethyl-pyrimidine-2-carbonitrile;
4-{(S)-3-[2-Chloro-4-((S)-2,2,2-trifluoro-1-methyl-ethoxy)-benzenesulfonyl]-pyrrolidin-1-yl}-6-trifluoromethyl-pyrimidine-2-carbonitrile;
4-[(S)-3-(2-Chloro-4-pyrazol-1-yl-benzenesulfonyl)-pyrrolidin-1-yl]-6-trifluoromethyl-pyrimidine-2-carbonitrile;
4-{(S)-3-[2-Chloro-4-(4-cyclopropyl-piperazin-1-yl)-benzenesulfonyl]-pyrrolidin-1-yl}-6-trifluoromethyl-pyrimidine-2-carbonitrile;
4-{(S)-3-[2-Chloro-4-(2,2,2-trifluoro-ethoxy)-benzenesulfonyl]-pyrrolidin-1-yl}-6-trifluoromethyl-pyrimidine-2-carbonitrile; and
4-{(S)-3-[2-Chloro-4-(2-methoxy-ethoxy)-benzenesulfonyl]-pyrrolidin-1-yl}-6-trifluoromethyl-pyrimidine-2-carbonitrile.

The compounds of the present invention can be prepared, for example, by the general synthetic procedures described below.

In the following schemes and description, $R^1$ to $R^6$ and $A^1$ to $A^4$ have, unless otherwise indicated, the meaning of $R^1$ to $R^6$ and $A^1$ to $A^4$ as defined above.

ABBREVIATIONS

ACN: Acetonitrile;
BOP: Benzotriazolyl-N-oxy-tris(dimethylamino)-phosphonium hexafluorophosphate;

BOP-Cl: Bis-(2-oxo-3-oxazolidinyl)-phosphinic acid chloride;
CDI: 1,1'-Carbonyldiimidazole;
DABCO: 1,4-Diazabicyclo[2.2.2]octan
DCM: Dichloromethane;
DIEA: Diisopropyl ethyl amine;
DMA: N,N-Dimethylacetamide;
DMF: N,N-Dimethylformamide;
EDCI: N-(3-Dimethylaminopropyl)-N'-ethyl-carbodiimide hydrochloride;
Fmoc: 9-Fluorenylmethyl carbamate;
HATU: O-(7-azabenzotriazol-1-yl)-1,1,3,3-tetramethyluronium hexafluorophosphate;
HOBT: 1-Hydroxybenzotriazole;
LiHMDS: Lithium bis(trimethylsilyl)amide;
MCPBA: 3-Chloroperbenzoic acid;
Mes-Cl: Mesyl chloride;
$Na_2SO_4$: Sodium sulfate
NMP=N-Methylpyrrolidinone;
Nos-Cl: 3-Nitrobenzenesulfonyl chloride;
PyBOP: Benzotriazol-1-yl-oxytripyrrolidinephosphonium hexafluorophosphate;
TEA: Triethylamine;
TBAF: Tetrabutylammonium fluoride;
TBTU: O-(Benzotriazol-1-yl)-N,N,N',N'-tetramethyluronium terafluoroborate;
Teoc: 2-Trimethylsilylethyl carbamate
TFA: Trifluoroacetic acid; and
THF: Tetrahydrofurane;
Tos-Cl: Toluene-4-sulfonyl chloride.

Scheme 1

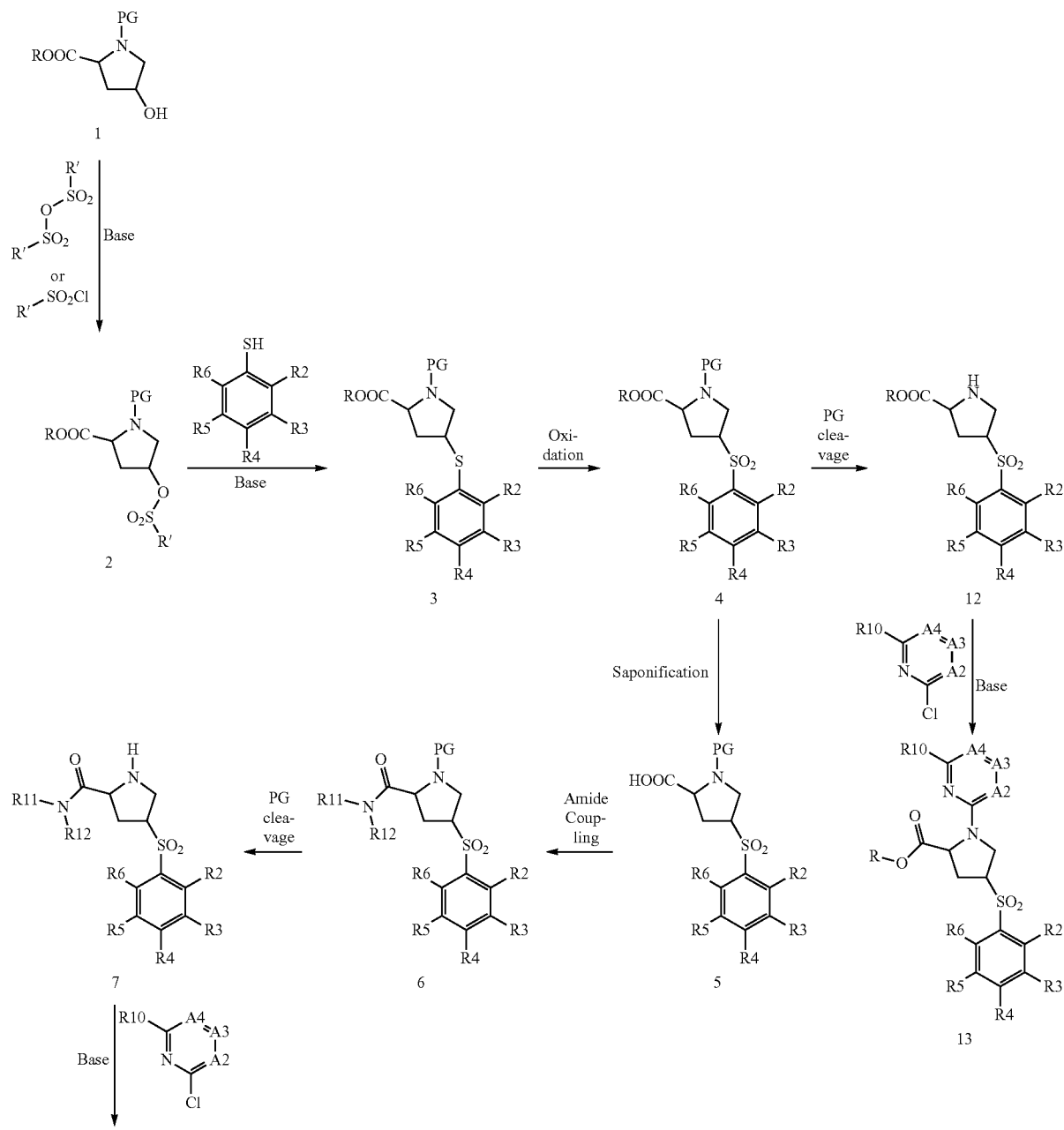

-continued

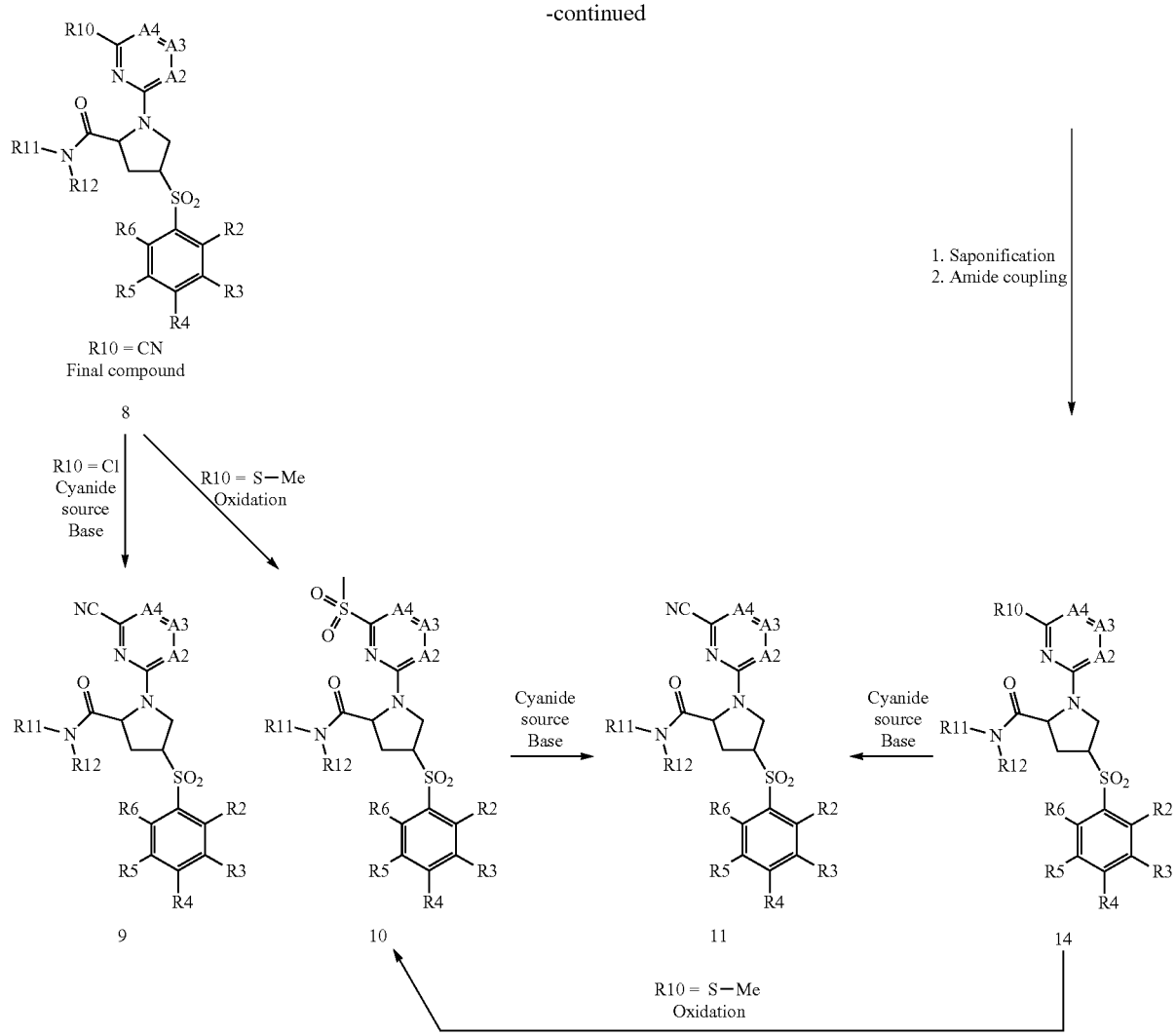

In scheme 1: R = methyl, ethyl or tert.-butyl; R' = methyl, trifluoromethyl, 3-nitrophenyl or 4-methylphenyl; R10 = CN, ——SMe or Cl; PG = Protecting group, e.g. Boc, Fmoc, Cbz or Teoc; R11 and R12 are independently selected from hydrogen, alkyl, haloalkylamino, hydroxyalkyl, alkylamino, amino, cyanoalkylamino, halophenylakylamino and cyanocycloalkylamino; or R11 and R12 togerther with the nitrogen atom to which they are attached form morpholinyl, halopyrrolidinyl or azetidinyl.

An appropriate orthogonally protected 4-hydroxy proline derivative such as (2S,4R)-4-hydroxy-pyrrolidine-1,2-dicarboxylic acid 1-tert-butyl ester 2-methyl ester or (2R,4R)-4-hydroxy-pyrrolidine-1,2-dicarboxylic acid 1-tert-butyl ester 2-methyl ester is reacted with a sulfonyl chloride such as Mes-Cl, Nos-Cl, Tos-Cl or triflic anhydride in the presence of a base such as TEA, DIEA, pyridine, etc. to yield compound 2. Reaction of 2 with thiols, in the presence of an appropriate base such as NaH, LiHMDS, DIEA, TEA, etc. yields compounds of type 3. Oxidation of the obtained thioether is accomplished by an appropriate oxidizing agent such as $H_2O_2$, oxone, MCPBA, etc. to yield compounds 4. Saponification of the ester is accomplished by using LiOH, NaOH in the case of R=methyl, ethyl; in the case of R=Boc, TFA or HCl or another appropriate acid can be used to yield compounds 5. Amide coupling is performed in presence of one of the various amide coupling reagents such as BOP-Cl, TBTU, BOP, PyBop, HATU, CDI, EDCI/HOBT, DIC/HOBT; DCC/HOBT, ammonium bicarbonate and di-tert.-butyl-dicarbonat etc. to yield corresponding amide 6. The protecting group PG is removed, in the case of Boc as protecting group with TFA, HCl or formic acid in an appropriate solvent such as THF, dioxane, $CH_2Cl_2$, etc. to yield compounds 7. In the case of PG=Fmoc, piperidine is used for cleavage. In the case of PG=Cbz, HBr in acetic acid or catalytic hydrogenation can be used. In the case of PG=Teoc, TBAF can be used for cleavage to yield compounds 7. Reaction of compounds 7 with chloro pyridine, chloro pyrimidine and chloro pyrazine derivatives in the presence of an appropriate base such as TEA, DIEA, pyridine, $Na_2CO_3$, $K_2CO_3$, $Cs_2CO_3$ and KF, NaF and CsF etc. yields compounds 8. In the case of R10=CN these are the final compounds. In case of R10=Cl, compounds 8 are reacted with a cyanide source such as NaCN, KCN or tetrabutylammonium cyanide in the presence of an appropriate base such as DABCO, pyridine, TEA, DIEA to yield the final compounds 9. In case R10=S-Me, compounds 8 are oxidized to the corresponding methylsulfones 10 with e.g. $H_2O_2$, oxone, MCPBA, etc. Finally, compounds 10 are reacted with a cyanide source such as NaCN, KCN or tetrabutylammonium cyanide to yield the final compounds 11. Alternatively, compounds 4 can be transformed to compounds 12 by cleavage of the protecting group PG. The protecting group PG is removed, in the case of Boc as protecting group with TFA, HCl or formic acid in an appropriate solvent such as THF, dioxane, CH$_2$Cl$_2$, etc. to yield compounds 7. In the case of PG=Fmoc, piperidine is used for cleavage, in the case of PG=Cbz, HBr in acetic acid or catalytic hydrogenation can be used. In the case of PG=Teoc, TBAF can be used for cleavage to yield compounds 12. Reaction of compounds 12 with chloro pyridine, chloro pyrimidine and chloro pyrazine derivatives in the presence of an appropriate base such as TEA, DIEA, pyridine, Na$_2$CO$_3$, K$_2$CO$_3$, Cs$_2$CO$_3$ and KF, NaF and CsF etc. yields compounds 13. Saponification of the ester 13 is accomplished by using LiOH, NaOH in the case of R=methyl, ethyl; in the case of R=Boc, TFA or HCl or another appropriate acid can be used. Subsequent amide coupling is performed in presence of one of the various amide coupling reagents such as BOP-Cl, TBTU, BOP, PyBop, HATU, CDI, EDCI/HOBT, DIC/HOBT; DCC/HOBT, ammonium bicarbonate and di-tert.-butyl-dicarbonate etc. to yield corresponding amide 14. In case of R10=Cl, compounds 14 are reacted with a cyanide source such as NaCN, KCN or tetrabutylammonium cyanide in the presence of an appropriate base such as DABCO, pyridine, TEA, DIEA to yield the final compounds 11. In case R10=S-Me, compounds 14 are oxidized to the corresponding methylsulfones 10 with e.g. H$_2$O$_2$, oxone, MCPBA, etc. Finally, compounds 10 are reacted with a cyanide source such as NaCN, KCN or tetrabutylammonium cyanide to yield the final compounds 11.

Scheme 2

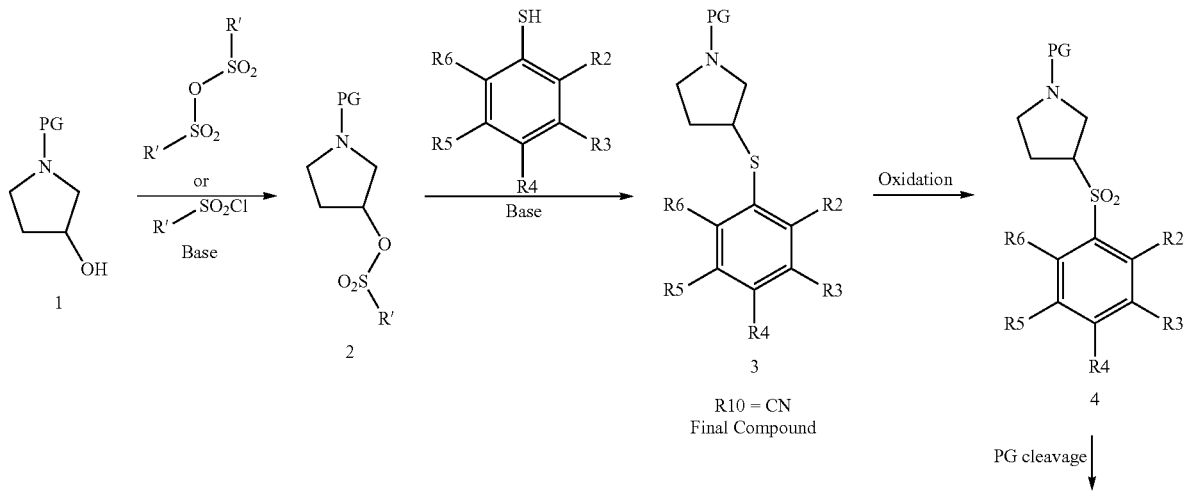

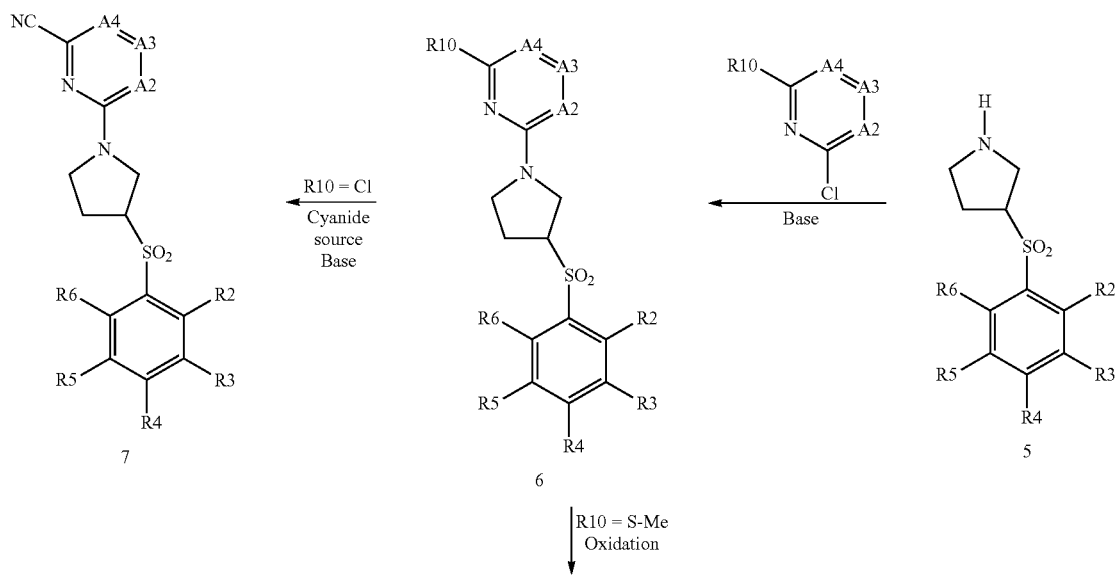

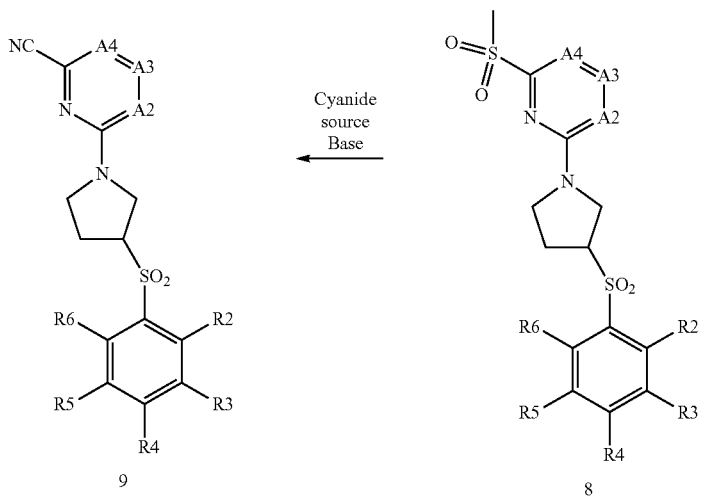

In scheme 2: PG = Protecting group e.g. Boc, Fmoc, Cbz or Teoc; R' = methyl, trifluoromethyl, 3-nitrophenyl or 4-methylphenyl; R10 = CN, -SMe or Cl.

An appropriate protected 3-hydroxy pyrrolidine derivative such as (R)-3-hydroxy-pyrrolidine-1-carboxylic acid tert-butyl ester is reacted with a sulfonyl chloride such as Mes-Cl, Nos-Cl, Tos-Cl or triflic anhydride in the presence of a base such as TEA, DIEA, pyridine, etc. to yield compound 2. Reaction of 2 with thiols, in the presence of an appropriate base such as NaH, LiHMDS, DIEA, TEA, etc yields compounds of type 3. Oxidation of the obtained thioether is accomplished by an appropriate oxidizing agent such as $H_2O_2$, Oxone, MCPBA, etc. to yield compounds 4. The protecting group PG is removed, in the case of Boc as protecting group with TFA, HCl or formic acid in an appropriate solvent such as THF, dioxane, $CH_2Cl_2$, etc. to yield compounds 5. In the case of PG=Fmoc, piperidine is used for cleavage, in the case of PG=Cbz, HBr in acetic acid or catalytic hydrogenation can be used. In the case of PG=Teoc, TBAF can be used for cleavage to yield compounds 5. Reaction of compounds 5 with chloro pyridine, chloro pyrimidine and chloro pyrazine derivatives in the presence of an appropriate base such as TEA, DIEA, pyridine, $Na_2CO_3$, $K_2CO_3$, $Cs_2CO_3$ and KF, NaF and CsF etc. yields compounds 6. In the case of R10=CN these are the final compounds. In case of R10=Cl, compounds 6 are reacted with a cyanide source such as NaCN, KCN or tetrabutyl-ammonium cyanide in the presence of an appropriate base such as DABCO, pyridine, TEA, DIEA to yield the final compounds 7. In case R10=S-Me, compounds 6 are oxidized to the corresponding methylsulfones 8 with e.g. $H_2O_2$, oxone, MCPBA, etc. Finally, compounds 8 are reacted with a cyanide source such as NaCN, KCN or tetrabutylammonium cyanide to yield the final compounds 9.

Scheme 3

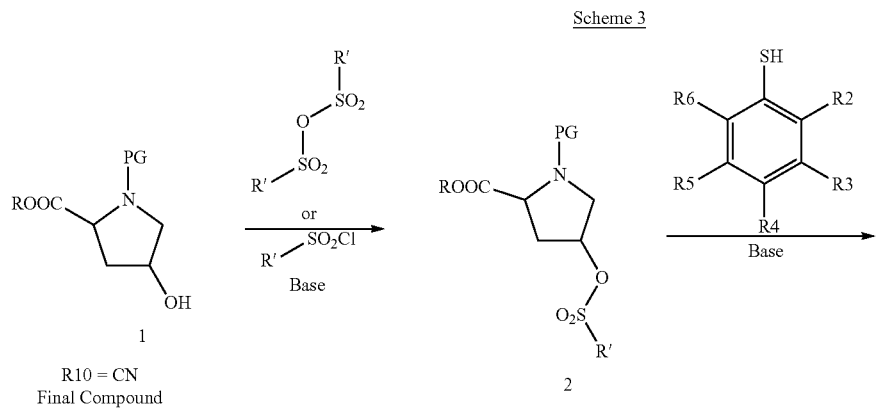

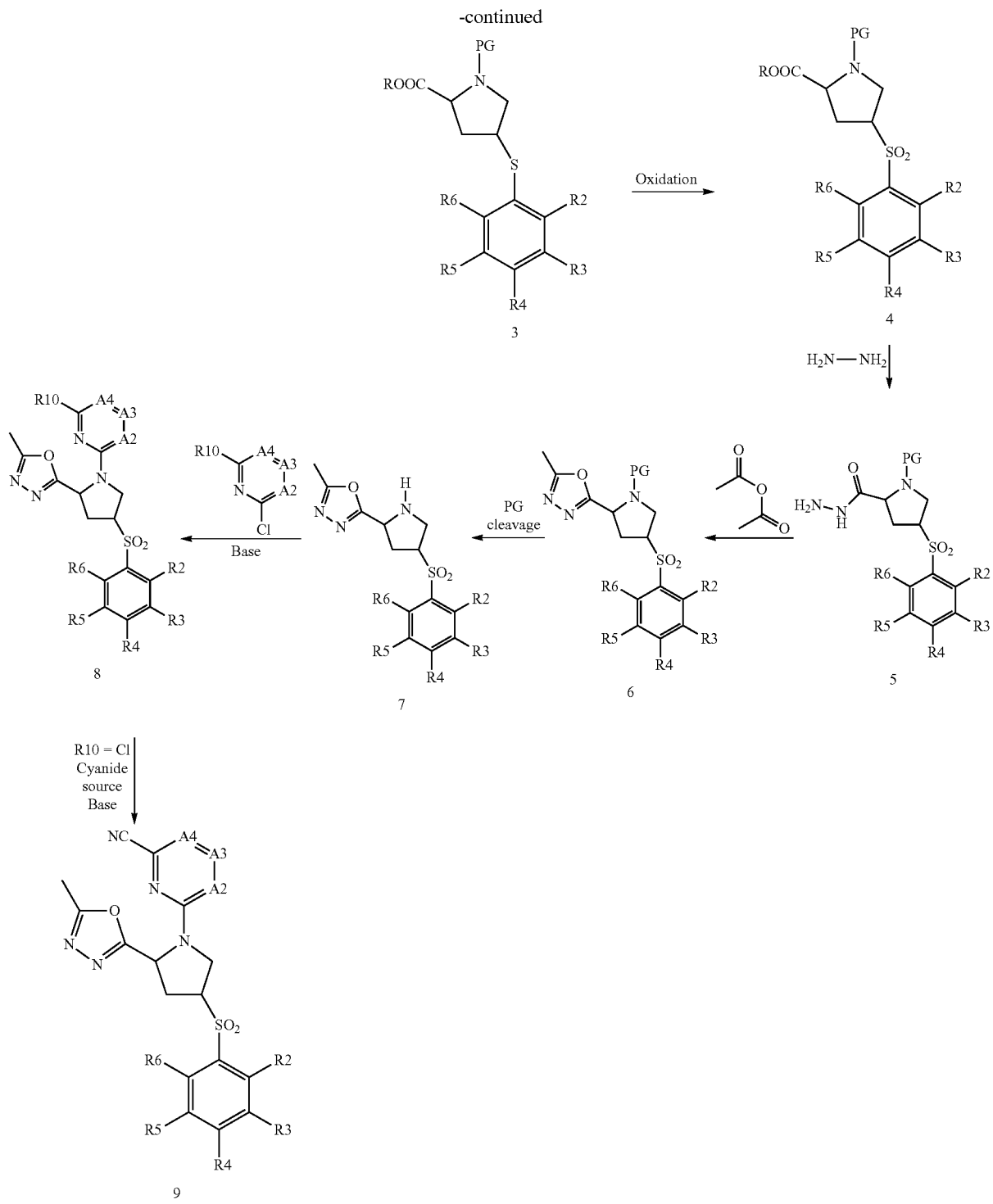

In scheme 3: R = methyl, ethyl or tert.-butyl; R' = methyl, trifluoromethyl, 3-nitrophenyl or 4-methylphenyl; R10 = CN or Cl; PG = Protecting group e.g. Boc, Fmoc, Cbz or Teoc.

An appropriate orthogonally protected 4-hydroxy proline derivative such as (2S,4R)-4-hydroxy-pyrrolidine-1,2-dicarboxylic acid 1-tert-butyl ester 2-methyl ester or (2R,4R)-4-hydroxy-pyrrolidine-1,2-dicarboxylic acid 1-tert-butyl ester 2-methyl ester is reacted with a sulfonyl chloride such as Mes-Cl, Nos-Cl, Tos-Cl or triflic anhydride in the presence of a base such as TEA, DIEA, pyridine, etc. to yield compound 2. Reaction of 2 with thiols, in the presence of an appropriate base such as NaH, LiHMDS, DIEA, TEA, etc yields compounds of type 3. Oxidation of the obtained thioether is accomplished by an appropriate oxidizing agent such as $H_2O_2$, oxone, MCPBA, etc. to yield compounds 4. Reaction of the esters 4 with hydrazine hydrate yields compounds 5. To accomplish the formation of the 1,3,4-oxadiazole derivatives 6, the hydrazides 5 are condensed with acetic acid anhydride in the presence of hexachloroethane and a phophane derivative such as e.g. triphenyl phosphane, tricyclohexyl phosphane. The protecting group PG is removed, in the case of Boc as protecting group with TFA, HCl or formic acid in an appropriate solvent such as THF, dioxane, $CH_2Cl_2$, etc. to yield compounds 7. In the case of PG=Fmoc, piperidine is used for cleavage; in the case of PG=Cbz, HBr in acetic acid or catalytic hydrogenation can be used. In the case of PG=Teoc, TBAF can be used for cleavage to yield compounds 7. Reaction of compounds 7 with chloro pyridine, chloro pyrimidine and chloro pyrazine derivatives in the presence of an appropriate base such as TEA, DIEA, pyridine, $Na_2CO_3$, $K_2CO_3$, $Cs_2CO_3$ and KF, NaF and CsF etc. yields compounds 8. In the case of R10=CN, these are the final compounds. In case of R10=Cl, compounds 8 are reacted with a cyanide source such as NaCN, KCN or tetrabutylammonium cyanide in the presence of an appropriate base such as DABCO, pyridine, TEA, DIEA to yield the final compounds 9.

Scheme 4

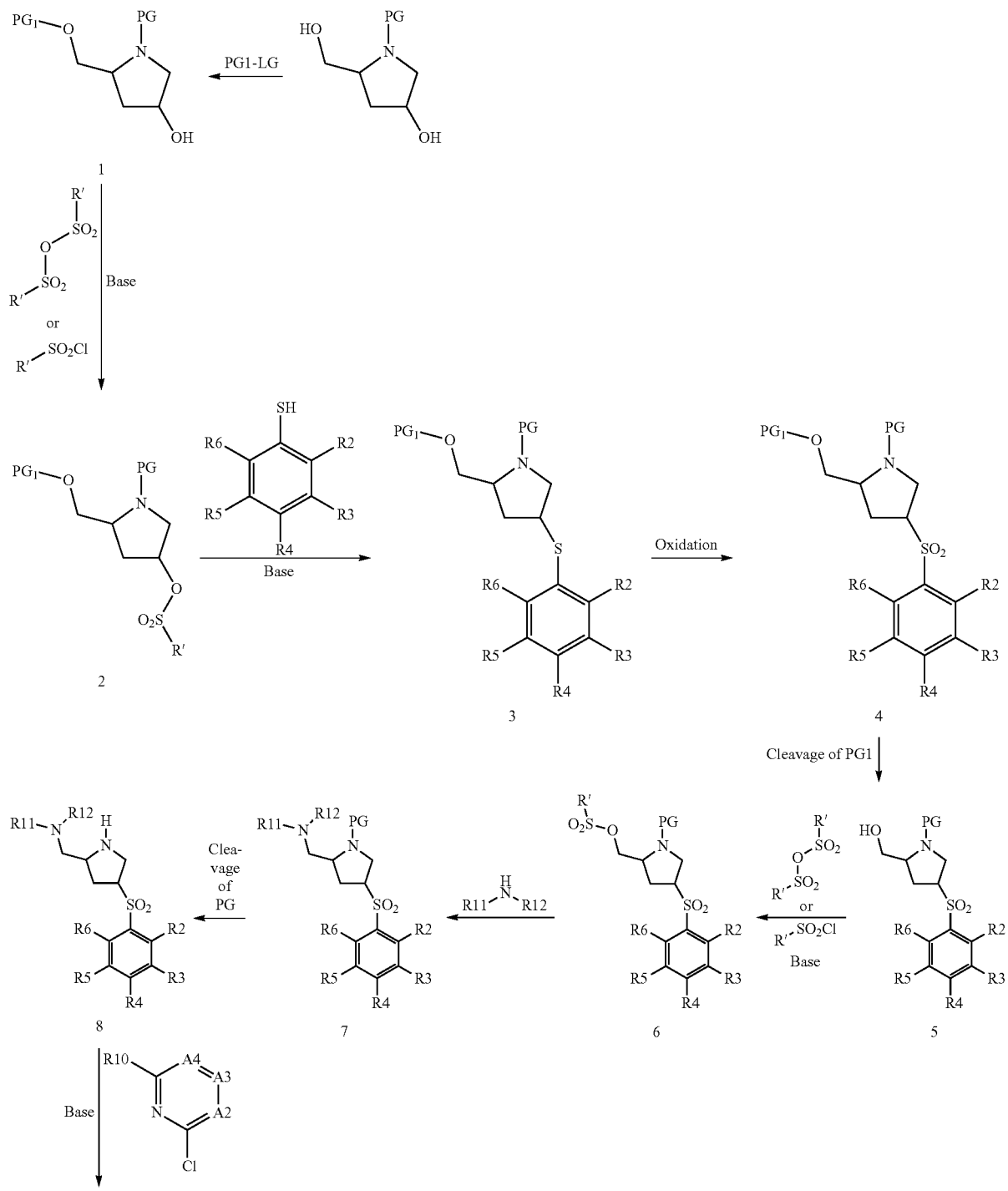

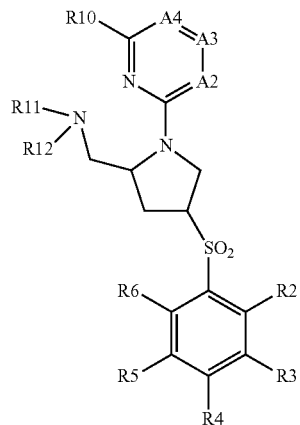

9
R10 = CN
Final compound

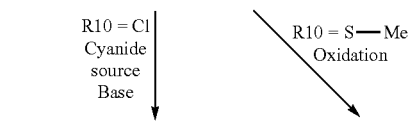

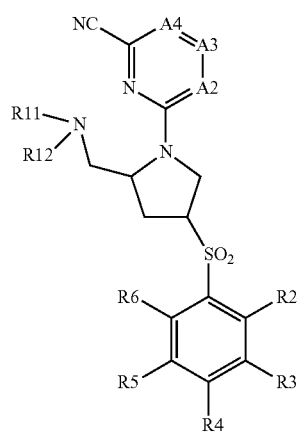

10

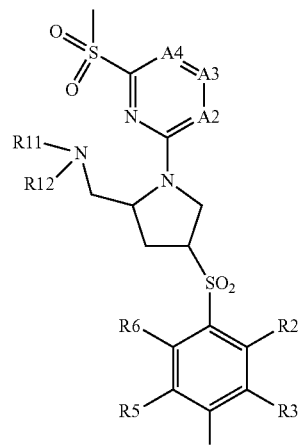

11

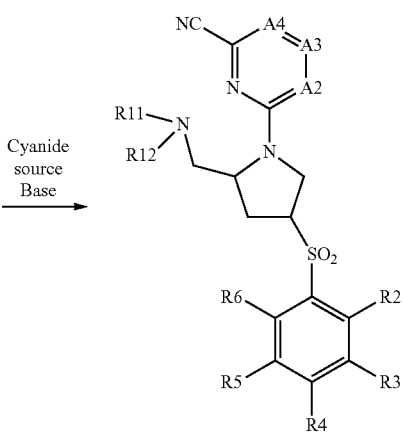

12

In scheme 4: PG = protecting group e.g. Boc, Fmoc or Cbz; PG1 = Protecting group e.g. thexyldimethylsilyl, trimethylsilyl, tert. butyldimethylsilyl or triphenylsilyl; R' = methyl, trifluoromethyl, 3-nitrophenyl or 4-methylphenyl; LG = e.g. Cl or Br; R10 = CN, —SMe or Cl; R11 and R12 are independently selected from hydrogen, alkyl, haloalkylamino, hydroxyalkyl, alkylamino, amino, cyanoalkylamino, halophenylalkylamino and cyanocycloalkylamino; or R11 and R12 together with the nitrogen atom to which they are attached form morpholinyl, halopyrrodinyl, piperazinyl, alkylpiperazinyl or azetidinyl.

An appropriate protected 4-hydroxy-2-hydroxymethylpyrrolidine derivative such as (2R,4R)-4-hydroxy-2-hydroxymethyl-pyrrolidine-1-carboxylic acid tert-butyl ester is reacted with a silylchloride such as thexyldimethylchlorsilane, trimethylchlorosilane or tert.-butyldimethylchlorosilane in the presence of imidazole to yield compound 1. Compound 1 is then reacted with a sulfonyl chloride such as Mes-Cl, Nos-Cl, Tos-Cl or triflic anhydride in the presence of a base such as TEA, DIEA, pyridine, etc. to yield compound 2. Reaction of 2 with thiols, in the presence of an appropriate base such as NaH, LiHMDS, DIEA, TEA, etc yields compounds of type 3. Oxidation of the obtained thioether is accomplished by an appropriate oxidizing agent such as $H_2O_2$, Oxone, MCPBA, etc. to yield compounds 4. Cleavage of PG1 is accomplished by a fluoride source such as TBAF, KF, etc. to yield compounds 5. The alcohol 5 is then reacted with a sulfonyl chloride such as Mes-Cl, Nos-Cl, Tos-Cl or triflic anhydride in the presence of a base such as TEA, DIEA, pyridine, etc. to yield compound 6. Nucleophilic displacement of the sulfonates of compounds 6 with amines R11-NH—R12 furnishes compounds 7. The protecting group PG is removed, in the case of Boc as protecting group with TFA, HCl or formic acid in an appropriate solvent such as THF, dioxane, $CH_2Cl_2$, etc. to yield compounds 8. In the case of PG=Fmoc, piperidine is used for cleavage; in the case of PG=Cbz, HBr in acetic acid or catalytic hydrogenation can be used. Reaction of compounds 8 with chloro pyridine, chloro pyrimidine and chloro pyrazine derivatives in the presence of an appropriate base such as TEA, DIEA, pyridine, $Na_2CO_3$, $K_2CO_3$, $Cs_2CO_3$ and KF, NaF and CsF etc. yields compounds 9. In the case of R10=CN, these are the final compounds. In case of R10=Cl, compounds 9 are reacted with a cyanide source such as NaCN, KCN or tetrabutylammonium cyanide in the presence of an appropriate base such as DABCO, pyridine, TEA, DIEA to yield the final compounds 10. In case R10=S-Me, compounds 9 are oxidized to the corresponding methylsulfones 11 with e.g. H$_2$O$_2$, oxone, MCPBA, etc.
Finally, compounds 11 are reacted with a cyanide source such as NaCN, KCN or tetrabutylammonium cyanide to yield the final compounds 12.
Scheme 5
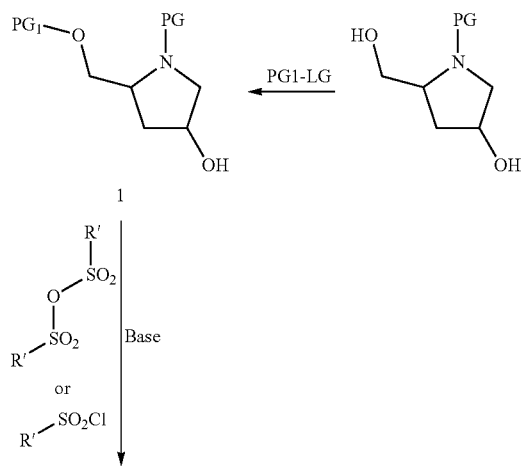
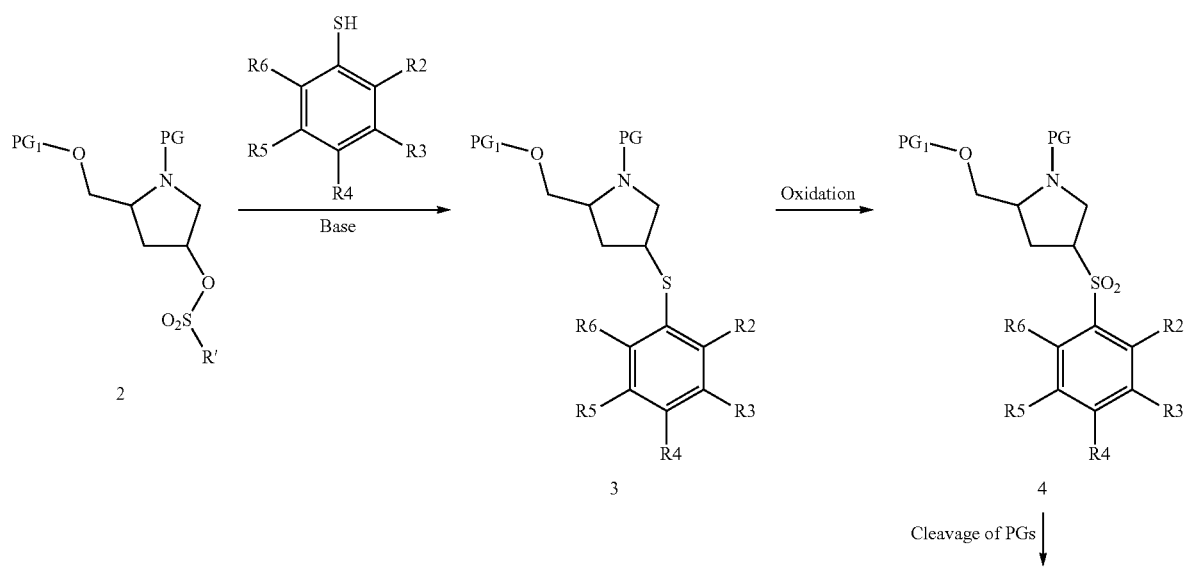
Cleavage of PGs

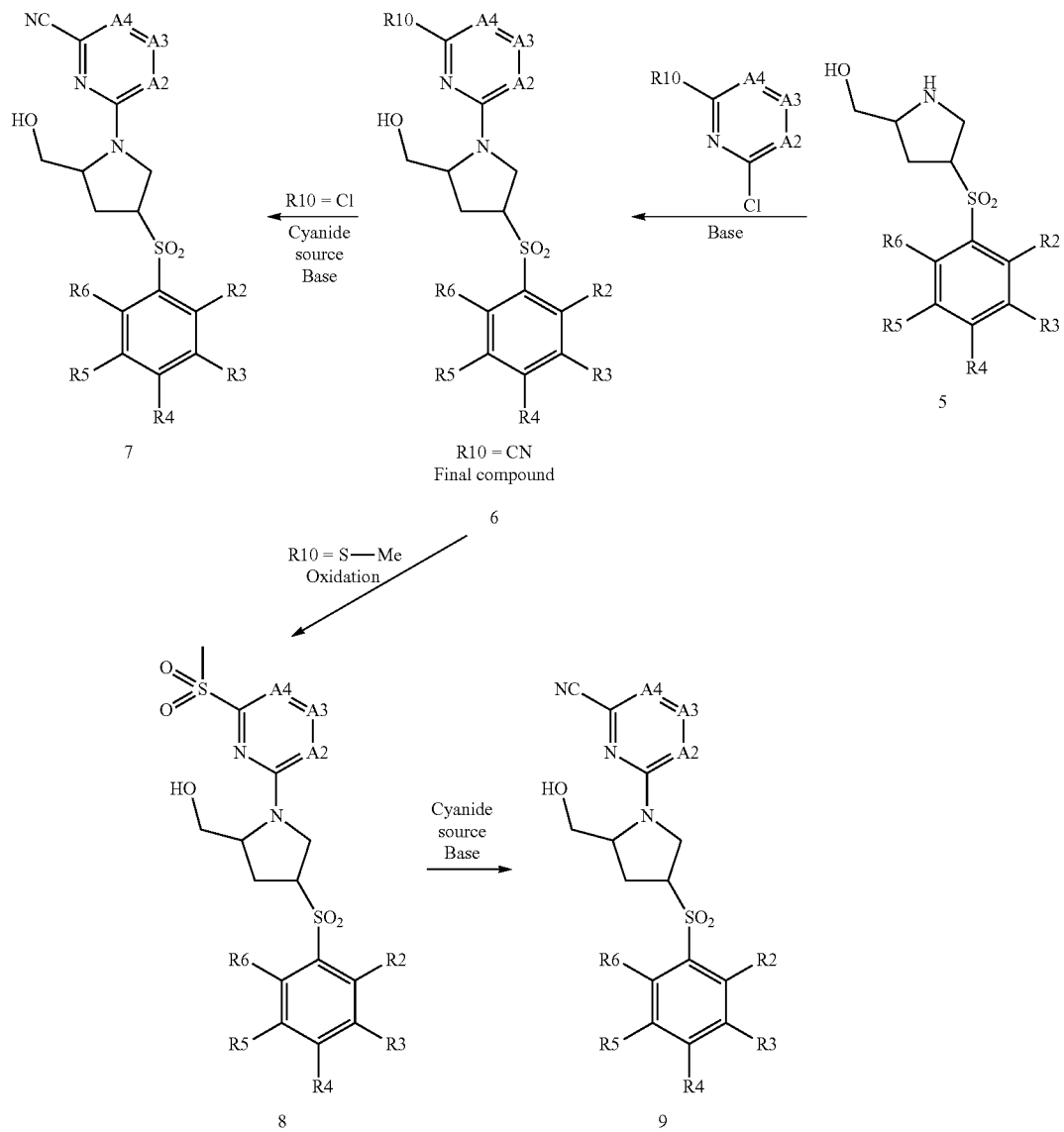

In scheme 5: PG = Protecting group e.g. Boc, Fmoc or Cbz; R10 = CN, ——SMe or Cl; PG1 = Protecting group e.g. thexyldimethylsilyl, trimethylsilyl, tert. butyldimethylsilyl or triphenylsilyl; R' = methyl, trifluoromethyl, 3-nitrophenyl or 4-methylphenyl; LG = e.g. Cl or Br.

An appropriate protected 4-hydroxy-2-hydroxymethylpyrrolidine derivative such as (2R,4R)-4-hydroxy-2-hydroxymethyl-pyrrolidine-1-carboxylic acid tert-butyl ester is reacted with a silylchloride such as thexyldimethylchlorsilane, trimethylchlorosilane or tert.-butyldimethylchlorosilane in the presence of imidazole to yield compound 1. Compound 1 is then reacted with a sulfonyl chloride such as Mes-Cl, Nos-Cl, Tos-Cl or triflic anhydride in the presence of a base such as TEA, DIEA, pyridine, etc. to yield compound 2. Reaction of 2 with thiols, in the presence of an appropriate base such as NaH, LiHMDS, DIEA, TEA, etc yields compounds of type 3. Oxidation of the obtained thioether is accomplished by an appropriate oxidizing agent such as $H_2O_2$, oxone, MCPBA, etc. to yield compounds 4. Cleavage of PG and PG1 is accomplished by an acid such as TFA, HCl, methanesulfonic acid, HBr in acetic acid, etc. to yield compounds 5. Reaction of compounds 5 with chloro pyridine, chloro pyrimidine and chloro pyrazine derivatives in the presence of an appropriate base such as TEA, DIEA, pyridine, $Na_2CO_3$, $K_2CO_3$, $Cs_2CO_3$ and KF, NaF and CsF etc. yields compounds 6. In the case of R10=CN, these are the final compounds. In case of R10=Cl, compounds 6 are reacted with a cyanide source such as NaCN, KCN or tetrabutylammonium cyanide in the presence of an appropriate base such as DABCO, pyridine, TEA, DIEA to yield the final compounds 7. In case R10=—S-Me, compounds 6 are oxidized to the corresponding methylsulfones 8 with e.g. $H_2O_2$, oxone, MCPBA, etc. Finally, compounds 8 are reacted with a cyanide source such as NaCN, KCN or tetrabutylammonium cyanide to yield the final compounds 9.

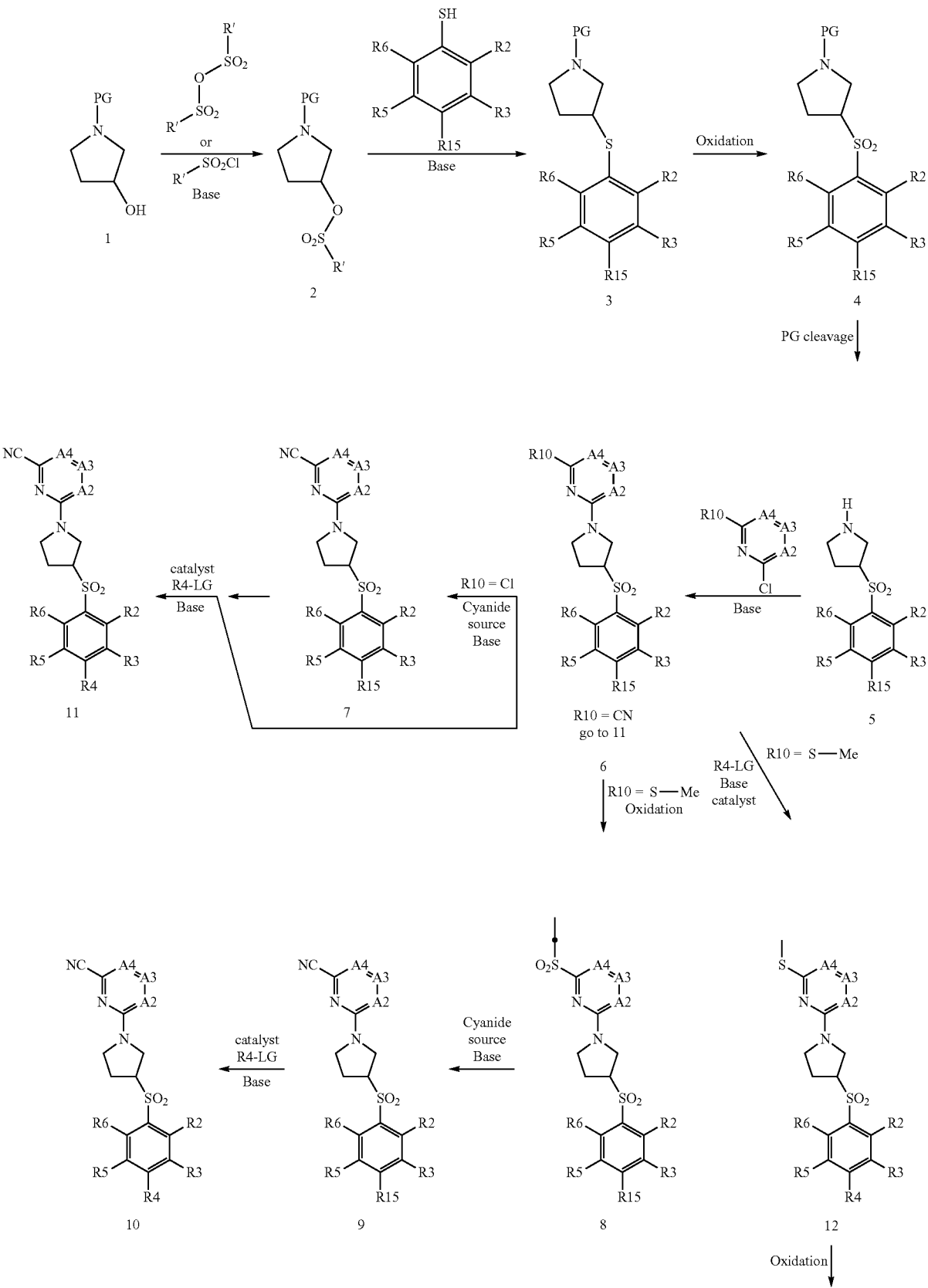
Scheme 6

-continued

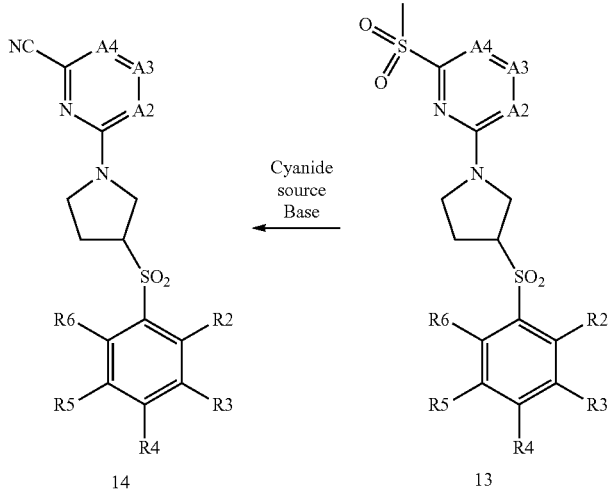

In scheme 6: R' is as defined above; PG = Protecting group e.g. Boc, Fmoc, Cbz or Teoc; X = N or O (R10 absent for O); R15 is a leaving group such as F, Cl, Br or I; R15 = F, Cl, Br or I; LG = H, B(OH)$_2$, B(OR)"$_2$ or 4,4,5,5-Pentamethyl-[1,3,2]dioxaborolanyl; R" = Me or Et; catalyst = e.g. copper or palladium salts with or without ligand well known in the art; R4 is as defined above except hydrogen.

An appropriate protected 3-hydroxy pyrrolidine derivative such as (R)-3-hydroxy-pyrrolidine-1-carboxylic acid tert-butyl ester is reacted with a sulfonyl chloride such as Mes-Cl, Nos-Cl, Tos-Cl or triflic anhydride in the presence of a base such as TEA, DIEA, pyridine, etc. to yield compound 2. Reaction of 2 with thiols, in the presence of an appropriate base such as NaH, LiHMDS, DIEA, TEA, etc yields compounds of type 3. Oxidation of the obtained thioether is accomplished by an appropriate oxidizing agent such as H$_2$O$_2$, oxone, MCPBA, etc. to yield compounds 4. The protecting group PG is removed, in the case of Boc as protecting group with TFA, HCl or formic acid in an appropriate solvent such as THF, dioxane, CH$_2$Cl$_2$, etc. to yield compounds 5. In the case of PG=Fmoc, piperidine is used for cleavage; in the case of PG=Cbz, HBr in acetic acid or catalytic hydrogenation can be used. In the case of PG=Teoc, TBAF can be used for cleavage to yield compounds 5. Reaction of compounds 5 with chloro pyridine, chloro pyrimidine and chloro pyrazine derivatives in the presence of an appropriate base such as TEA, DIEA, pyridine, Na$_2$CO$_3$, K$_2$CO$_3$, Cs$_2$CO$_3$ and KF, NaF and CsF etc. yields compounds 6. In the case of R10=CN, these compounds are directly reacted with amines or alcohols or boronic acid derivatives R4-LG in the presence of a base such as TEA, DIEA, pyridine, Na$_2$CO$_3$, K$_2$CO$_3$, Cs$_2$CO$_3$ and KF, NaF and CsF or in the presence of a base as above and a catalyst to yield compounds 11. In case of R10=Cl, compounds 6 are reacted with a cyanide source such as NaCN, KCN or tetrabutylammonium cyanide in the presence of an appropriate base such as DABCO, pyridine, TEA, DIEA to yield compounds 7. Compounds 7 are reacted with amines or alcohols or boronic acid derivatives R4-LG in the presence of a base such as TEA, DIEA, pyridine, Na$_2$CO$_3$, K$_2$CO$_3$, Cs$_2$CO$_3$ and KF, NaF and CsF or in the presence of a base as above and a catalyst to yield the final compounds 11. In case R10=S-Me, compounds 6 are oxidized to the corresponding methylsulfones 8 with e.g. H$_2$O$_2$, oxone, MCPBA, etc. Finally, compounds 8 are reacted with a cyanide source such as NaCN, KCN or tetrabutylammonium cyanide to yield compounds 9. Compounds 9 are reacted with amines or alcohols or boronic acid derivatives R4-LG in the presence of a base such as TEA, DIEA, pyridine, Na$_2$CO$_3$, K$_2$CO$_3$, Cs$_2$CO$_3$ and KF, NaF and CsF or in the presence of a base as above and a catalyst to yield the final compounds 10. Alternatively, in case R10=S-Me, compounds 6 are reacted with amines or alcohols or boronic acid derivatives R4-LG in the presence of a base such as TEA, DIEA, pyridine, Na$_2$CO$_3$, K$_2$CO$_3$, Cs$_2$CO$_3$ and KF, NaF and CsF or in the presence of a base as above and a catalyst to yield compounds 12. Compounds 12 are oxidized to the corresponding methylsulfones 13 with e.g. H$_2$O$_2$, Oxone, MCPBA, etc. Finally, compounds 13 are reacted with a cyanide source such as NaCN, KCN or tetrabutylammonium cyanide to yield the final compounds 14.

Scheme 7

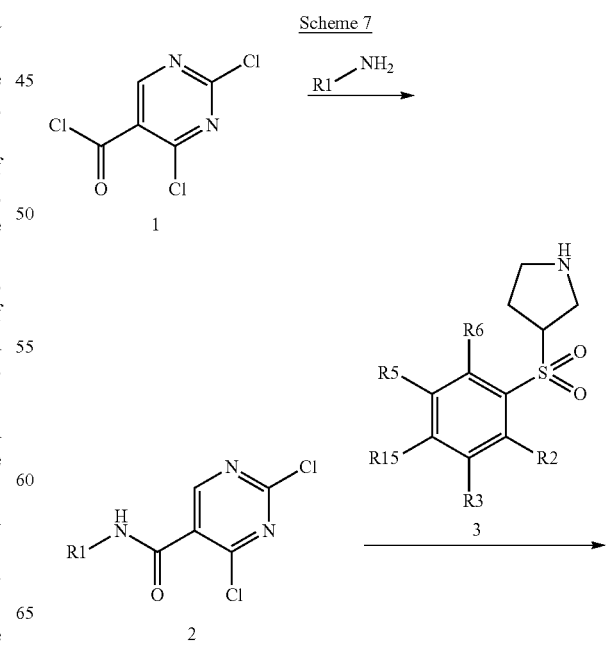

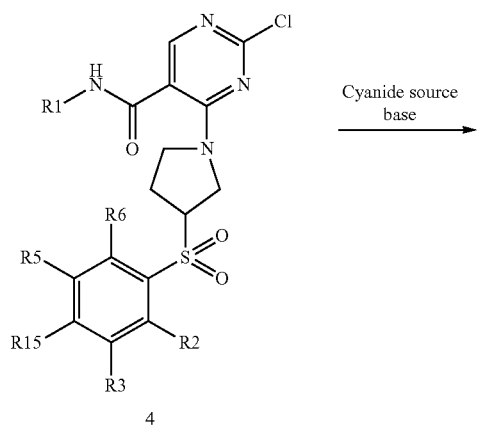

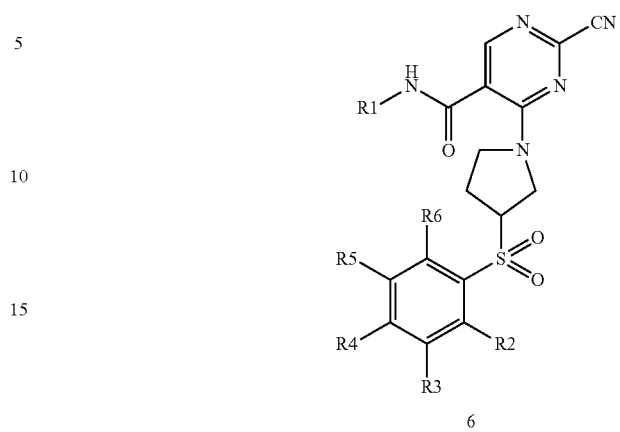

In scheme 7: R15 is a leaving group such as F, Cl, Br or I; R15 = F, Cl, Br or I; LG = H, B(OH)₂, B(OR")₂ or 4,4,5,5-Pentamethyl-[1,3,2] dioxaborolanyl; catalyst = e.g. copper or palladium salts with or without ligand well known in the art; R4 is as defined above except hydrogen.

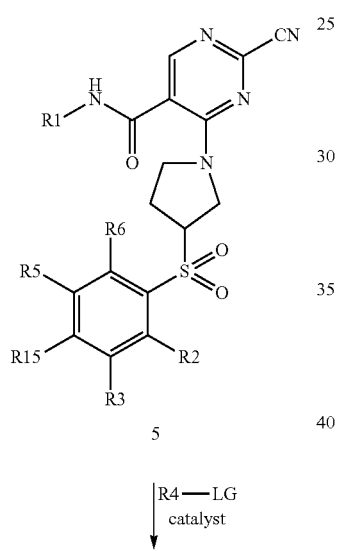

2,4-Dichloro-pyrimidine-5-carbonyl chloride 1 is reacted in the presence of a suitable base such as TEA, DIEA, pyridine, etc. with an amine R1-NH₂ in an appropriate solvent such as THF, DMF, ACN, dichloromethane, etc. to yield the corresponding amide 2. After that, 2 is reacted with the pyrrolidine derivative 3 (synthesis of 3 described above) in the presence of an appropriate base such as TEA, DIEA, pyridine, Na₂CO₃, K₂CO₃, Cs₂CO₃ and KF, NaF and CsF etc. to yield compound 4. Compound 4 is reacted with a cyanide source such as NaCN, KCN or tetrabutylammonium cyanide in the presence of an appropriate base such as DABCO, pyridine, TEA, DIEA to yield final compounds 5. Compounds 5 are reacted with amines or alcohols or boronic acid derivatives R4-LG in the presence of a base such as TEA, DIEA, pyridine, Na₂CO₃, K₂CO₃, Cs₂CO₃ and KF, NaF and CsF or in the presence of a base as above and a catalyst to yield the final compounds 6.

Scheme 8

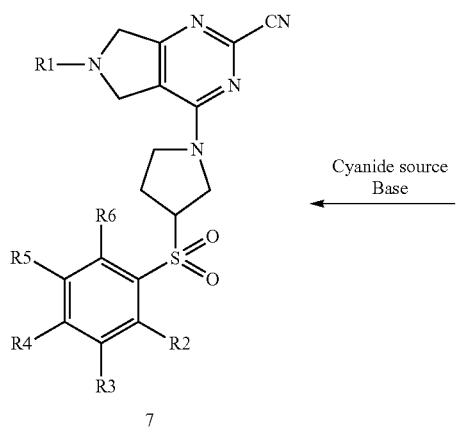
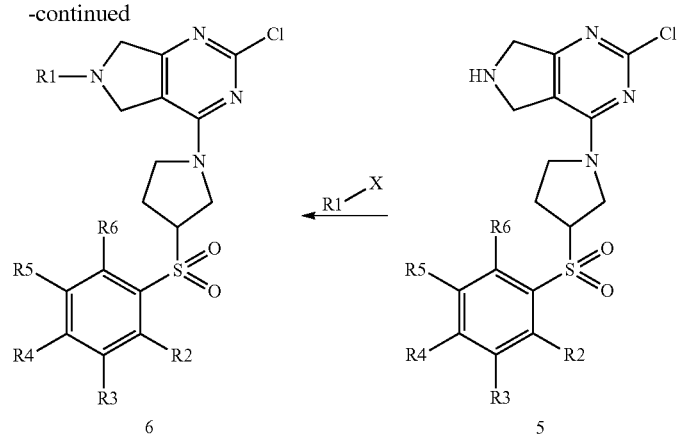

In scheme 8: PG: protecting group as defined in scheme 1; R15 is a leaving group such as F, Cl, Br or I; R15 = F, Cl, Br or I; LG = H, B(OH)₂, B(OR")₂ or 4,4,5,5-Pentamethyl-[1,3,2]dioxaborolanyl; catalyst = e.g. copper or palladium salts with or without ligand well known in the art; R4 is as defined above except hydrogen. X = triflate, tosylate, brosylate, nosylate, mesylate, Cl, Br, I, OH (in the case of carboxylic acids).

Pyrrolidine derivative 1 (synthesis described above) is reacted with amines or alcohols or boronic acid derivatives R4-LG in the presence of a base such as TEA, DIEA, pyridine, $Na_2CO_3$, $K_2CO_3$, $Cs_2CO_3$ and KF, NaF and CsF or in the presence of a base as above and a catalyst to yield the compounds 2. The protecting group PG is removed, in the case of Boc as protecting group with TFA, HCl or formic acid in an appropriate solvent such as THF, dioxane, $CH_2Cl_2$, etc. to yield compounds 3. In the case of PG=Fmoc, piperidine is used for cleavage. In the case of PG=Cbz, HBr in acetic acid or catalytic hydrogenation can be used. In the case of PG=Teoc, TBAF can be used for cleavage to yield compounds 3. After that compound 3 is reacted with a protected 2,4-dichloro-6,7-dihydro-5H-pyrrolo[3,4-d]pyrimidine in the presence of an appropriate base such as TEA, DIEA, pyridine, $Na_2CO_3$, $K_2CO_3$, $Cs_2CO_3$ and KF, NaF and CsF etc. to yield compound 4. The protecting group PG is removed, in the case of Boc as protecting group with TFA, HCl or formic acid in an appropriate solvent such as THF, dioxane, $CH_2Cl_2$, etc. to yield compounds 5. In the case of PG=Fmoc, piperidine is used for cleavage. In the case of PG=Cbz, HBr in acetic acid or catalytic hydrogenation can be used. In the case of PG=Teoc, TBAF can be used for cleavage to yield compounds 5. Compound 5 is subsequently reacted with alkylating or acylating agents R1-X with methods known in the art to yield compound 6. Compound 6 is reacted with a cyanide source such as NaCN, KCN or tetrabutyl-ammonium cyanide in the presence of an appropriate base such as DABCO, pyridine, TEA, DIEA to yield final compounds 7.

The invention is also directed to a process for the preparation of a compound of formula (I) comprising one of the following steps:

(a) the reaction of a compound of formula (A)

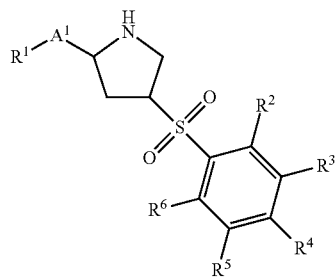
(A)

in the presence of a base and a compound of formula (B)

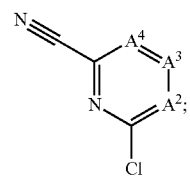
(B)

(b) the reaction of a compound of formula (C)

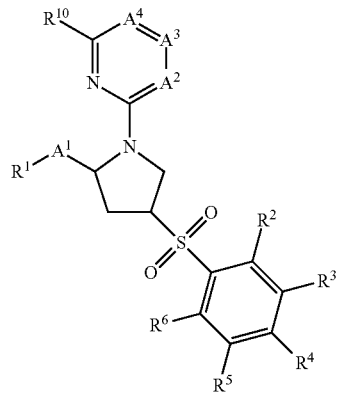
(C)

in the presence of a cyanide source and a base;
wherein $A^1$ to $A^4$ and $R^1$ to $R^6$ are as defined above and wherein $R^{10}$ is chloro, fluoro or methylsulfonyl.

In step (a), the base is for example TEA, DIEA, pyridine, $Na_2CO_3$, $K_2CO_3$, $Cs_2CO_3$ and KF or NaF and CsF.

In step (b), the cyanide source is for example NaCN, KCN, potassium ferrocyanide, tetraethylammonium cyanide or tetrabutylammonium cyanide.

In step (b), the base is for example DABCO, pyridine, lutidine, TEA or DIEA $Na_2CO_3$, $K_2CO_3$, $Cs_2CO_3$ and KF or NaF and CsF.

The invention further relates to a compound of formula (I) for use as therapeutically active substance.

The invention also relates to a compound of formula (I) for use as therapeutically active substance for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration, particularly atherosclerosis, cancer, reduction of cardiovascular events in chronic kidney disease, age related macular degeneration, diabetic nephropathy or diabetic retinopathy.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The invention is also directed to a pharmaceutical composition comprising a compound of formula (I) and a therapeutically inert carrier.

The invention is also concerned with the use of a compound of formula (I) for the preparation of medicaments for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration, particularly atherosclerosis, cancer, reduction of cardiovascular events in chronic kidney disease, age related macular degeneration, diabetic nephropathy or diabetic retinopathy.

A compound of formula (I), when manufactured according to the process of the invention is also an object of the invention.

The invention is also concerned with a method for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration, particularly atherosclerosis, cancer, reduction of cardiovascular events in chronic kidney disease, age related macular degeneration, diabetic nephropathy or diabetic retinopathy, which method comprises administering an effective amount of a compound of formula (I).

The invention will now be illustrated with the following examples which have no limiting character.

EXAMPLES

Example 1

6-[(2S,4S)-4-(2-Chloro-benzenesulfonyl)-2-(morpholine-4-carbonyl)-pyrrolidin-1-yl]pyrazine-2-carbonitrile

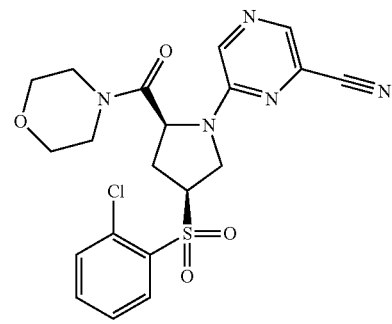 [SMILES: N#Cc1cncc(N2C[C@@H](S(=O)(=O)c3ccccc3Cl)C[C@H]2C(=O)N2CCOCC2)n1]

A) (2S,4R)-4-(3-Nitro-benzenesulfonyloxy)-pyrrolidine-1,2-dicarboxylic acid 1-tert-butyl ester 2-methyl ester

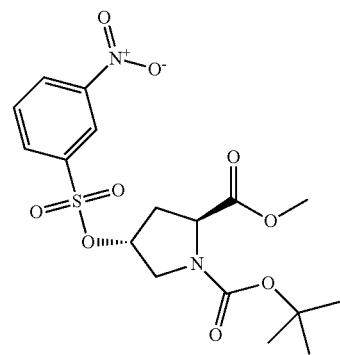 [SMILES: COC(=O)[C@@H]1C[C@@H](OS(=O)(=O)c2cccc([N+](=O)[O-])c2)CN1C(=O)OC(C)(C)C]

(2S,4R)-4-Hydroxy-pyrrolidine-1,2-dicarboxylic acid 1-tert-butyl ester 2-methyl ester (5.0 g) was dissolved in DCM (50 mL) and 3-nitrobenzenesulfonyl chloride (4.8 g) was added. This solution was cooled to 5° C. and the TEA (8.52 mL) was carefully added. The reaction mixture was stirred at 25° C. for 18 h. The reaction mixture was then extracted with 0.1 N aqueous HCl (50 mL) and aqueous $Na_2CO_3$ (50 mL) and brine (50 mL). The organic layer was dried over $Na_2SO_4$, filtrated and evaporated to dryness to yield a light brown amorphous solid (9.05 g). MS: m/z=431.4 [M+H]$^+$.

B) (2S,4S)-4-(2-Chloro-phenylsulfanyl)-pyrrolidine-1,2-dicarboxylic acid 1-tert-butyl ester 2-methyl ester

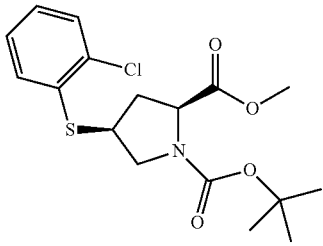 [SMILES: COC(=O)[C@@H]1C[C@H](Sc2ccccc2Cl)CN1C(=O)OC(C)(C)C]

Example 1A (3.0 g) was dissolved in ACN (30 mL). 2-Chlorothiophenol (3.0 g) and TEA (2.91 mL) were added to the reaction mixture. The reaction mixture was stirred at reflux for 18 h. The reaction mixture was then quenched with water (20 mL) and extracted with ethyl acetate (200 mL) and brine (30 mL). The organic layers were dried over Na$_2$SO$_4$, filtrated and evaporated to dryness. The crude product was purified by flash chromatography (silica gel; ethyl acetate/n-heptane) to yield a colorless oil (2.07 g; 79.9%). MS: m/z=372.0 [M+H]$^+$.

C) (2S,4S)-4-(2-Chloro-benzenesulfonyl)-pyrrolidine-1,2-dicarboxylic acid 1-tert-butyl ester 2-methyl ester

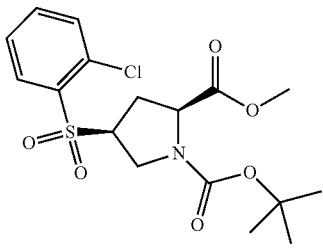 [SMILES: COC(=O)[C@@H]1C[C@H](S(=O)(=O)c2ccccc2Cl)CN1C(=O)OC(C)(C)C]

Example 1B (2.06 g) was dissolved in DCM (25 mL) and cooled to 0° C. MCPBA (2.87 g) was slowly added and the reaction mixture was allowed to warm to 25° C. The reaction mixture was stirred at 25° C. for 18 h. The reaction mixture was diluted with DCM (50 mL) and extracted three times with aqueous Na$_2$CO$_3$ solution (50 mL) and brine (50 mL). The organic layers were dried over Na$_2$SO$_4$, filtrated and evaporated (a peroxide test prior was negative) to dryness to yield a light brown oil (2.06 g; 92%). MS: m/z=404.0 [M+H]$^+$.

D) (2S,4S)-4-(2-Chloro-benzenesulfonyl)-pyrrolidine-1,2-dicarboxylic acid 1-tert-butyl ester

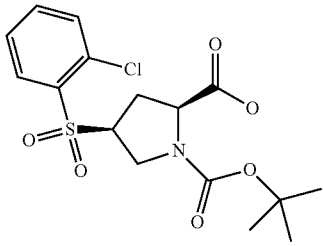 [SMILES: CC(C)(C)OC(=O)N1C[C@@H](S(=O)(=O)c2ccccc2Cl)C[C@H]1C(=O)O]

Example 1C (1.0 g) was dissolved in THF/water (7.5 ml/2.5 mL). To this stirring solution LiOH (65 mg) was added and the reaction mixture was stirred at 25° C. for 4 h. The reaction mixture was diluted with ethyl acetate (20 mL) and extracted with 1N aqueous HCl solution (10 mL) and brine. The organic layers were dried over Na$_2$SO$_4$, filtrated and evaporated to dryness to yield a colorless oil (1.16 g, 120%, crude product). MS: m/z=390.3 [M+H]$^+$; 388.2 [M−H]$^−$.

E) (2S,4S)-4-(2-Chloro-benzenesulfonyl)-2-(morpholine-4-carbonyl)-pyrrolidine-1-carboxylic acid tert-butyl ester

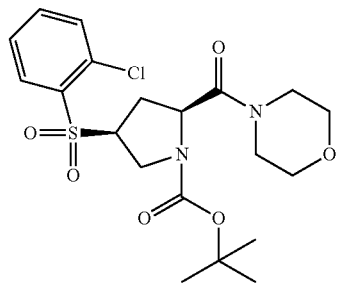 [SMILES: CC(C)(C)OC(=O)N1C[C@@H](S(=O)(=O)c2ccccc2Cl)C[C@H]1C(=O)N1CCOCC1]

Example 1D (1.1 g) was dissolved in ACN (15 mL) and EDCI (703 mg), HOBT (562 mg) and DIPEA (0.62 mL) were added. The reaction mixture was stirred for 1 h at 25° C. After that, morpholine (0.32 mL) was added and the reaction mixture was stirred at 25° C. for 18 h. After that the reaction mixture was diluted with ethyl acetate (50 mL) extracted with 1N aqueous HCl (20 mL), aqueous Na$_2$CO$_3$ solution (20 mL) and brine (20 mL). The organic layers were dried over Na$_2$SO$_4$, filtrated and evaporated to dryness. The crude material was purified by flash chromatography (20 g silica gel; ethyl acetate/n-heptane) to yield an off-white foam (0.57 g; 44%). MS: m/z=459.1 [M+H]$^+$.

F) [(2S,4S)-4-(2-Chloro-benzenesulfonyl)-pyrrolidin-2-yl]-morpholin-4-yl-methanone

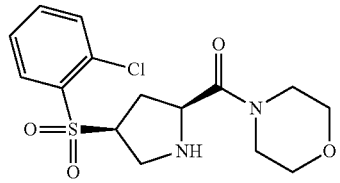 [SMILES: O=C([C@@H]1C[C@H](S(=O)(=O)c2ccccc2Cl)CN1)N1CCOCC1]

Example 1E (0.57 g) was dissolved in DCM (3.5 mL) and TFA (2.5 mL) was added. The reaction mixture was stirred at 25° C. for 18 h. The reaction mixture was diluted with DCM (3.5 mL) and extracted with aqueous Na$_2$CO$_3$ solution (10 mL) and brine (10 mL). The organic layers were dried over Na$_2$SO$_4$, filtrated and evaporated to dryness to yield a white solid (0.43 g; 96%). MS: m/z=359.1 [M+H]$^+$.

G) 6-[(2S,4S)-4-(2-Chloro-benzenesulfonyl)-2-(morpholine-4-carbonyl)-pyrrolidin-1-yl]-pyrazine-2-carbonitrile (Title compound)

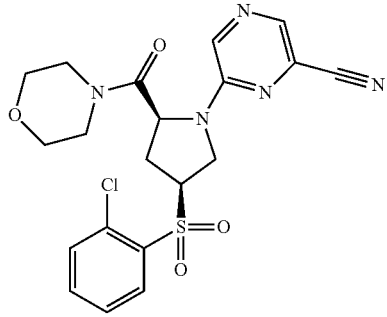 [SMILES: N#Cc1cncc(N2C[C@@H](S(=O)(=O)c3ccccc3Cl)C[C@H]2C(=O)N2CCOCC2)n1]

Example 1F (60 mg), 6-cyano-2-chloropyrazine (26 mg), KF (1 mg) and TEA (0.07 mL) were combined in a microwave tube and dissolved in ACN (2 mL). The reaction mixture was stirred in the micro wave oven at 130° C. for 1 h. The reaction mixture was filtrated and purified by preparative HPLC to yield an off-white solid (9 mg; 12%). MS: m/z=462.3 [M+H]+.

Example 2

(2S,4S)-4-(2-Chloro-benzenesulfonyl)-1-(6-cyano-pyrazin-2-yl)-pyrrolidine-2-carboxylic acid methyl ester

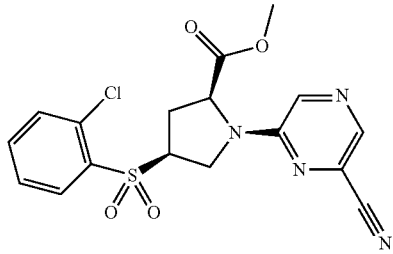

A) (2S,4S)-4-(2-Chloro-benzenesulfonyl)-pyrrolidine-2-carboxylic acid methyl ester

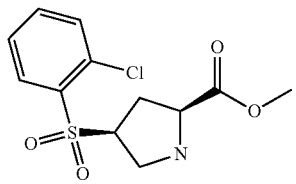 [SMILES: COC(=O)[C@@H]1C[C@H](S(=O)(=O)c2ccccc2Cl)CN1]

Example 1C (100 mg) was dissolved in DCM (1.5 mL) and TFA (0.75 mL) was added. The reaction mixture was stirred at 25° C. for 18 h. After that the reaction mixture was diluted with DCM (10 mL) and extracted with aqueous Na$_2$CO$_3$ solution (10 mL) and brine (10 mL). The organic layers were dried over Na$_2$SO$_4$, filtrated and evaporated to dryness to yield an off-white solid (71 mg; 95%). MS: m/z=304.3 [M+H]+.

B) (2S,4S)-4-(2-Chloro-benzenesulfonyl)-1-(6-cyano-pyrazin-2-yl)-pyrrolidine-2-carboxylic acid methyl ester

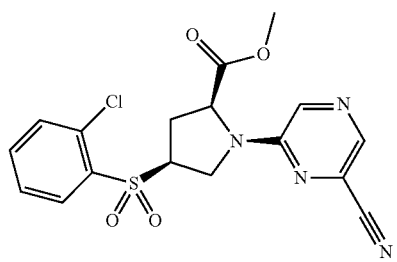

The title compound was prepared in analogy to example 1G starting from example 2A (71 mg) to yield a brown solid (9 mg; 10%). MS: m/z=407.1 [M+H]+.

Example 3

6-[3-(4-Hydroxy-benzenesulfonyl)-pyrrolidin-1-yl]-pyrazine-2-carbonitrile

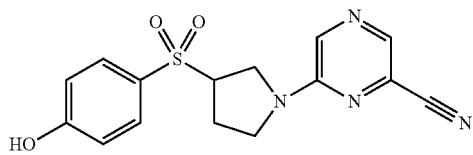 [SMILES: N#Cc1cncc(N2CCC(S(=O)(=O)c3ccc(O)cc3)C2)n1]

The title compound was prepared in analogy to the methods described for example 1G starting from CAS 371240-19-6 to yield a light brown waxy solid (19 mg; 11%). MS: m/z=331.3 [M+H]+.

Example 4

6-[3-({4-[(6-cyanopyrazin-2-yl)oxy]phenyl}sulfonyl)pyrrolidin-1-yl]pyrazine-2-carbonitrile

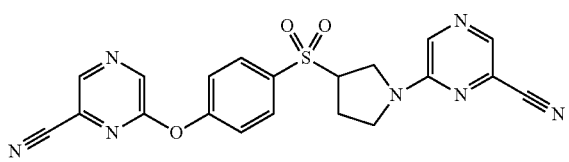 [SMILES: N#Cc1cncc(Oc2ccc(S(=O)(=O)C3CCN(c4cncc(C#N)n4)C3)cc2)n1]

The title compound was obtained as a by-product during the synthesis of example 3 to yield light brown solid (38 mg; 25%). MS: m/z=434.2 [M+H]+.

Example 5

Lithium; (2S,4S)-4-(2-chloro-benzenesulfonyl)-1-(6-cyano-pyrazin-2-yl)-pyrrolidine-2-carboxylate

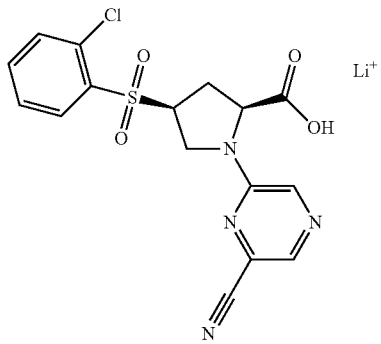 [SMILES: N#Cc1cncc(N2C[C@@H](S(=O)(=O)c3ccccc3Cl)C[C@H]2C(=O)O)n1 ; [Li+]]

Example 2 (77 mg) was dissolved in THF (1.5 mL) and LiOH hydrate (10 mg) was added. The reaction mixture was stirred at 25° C. for 1 h. After that, water (0.05 mL) was added and the mixture was stirred for 0.5 h at 25° C. The reaction mixture was evaporated to dryness to yield the title compound as a light brown solid (83 mg; 100%). MS: m/z=390.9 [M–H]⁻.

Example 6

(2S,4S)-4-(2-Chloro-benzenesulfonyl)-1-(6-cyano-pyrazin-2-yl)-pyrrolidine-2-carboxylic acid (2,2,2-trifluoro-ethyl)-amide

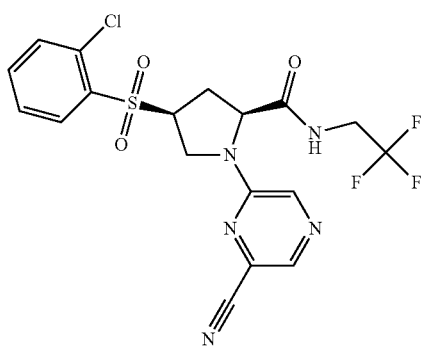 [SMILES: N#Cc1cncc(N2C[C@@H](S(=O)(=O)c3ccccc3Cl)C[C@H]2C(=O)NCC(F)(F)F)n1]

Example 5 (81 mg) was dissolved in DMF (2.0 mL) and EDCI (58 mg), HOBT (47 mg) and DIEA (0.05 mL) were added at 25° C. The reaction mixture was stirred at 25° C. for 2 h. After that, 2,2,2-trifluoroethylamine (30 mg) was added and the reaction mixture was stirred at 25° C. for 18 h. The reaction mixture was filtrated and purified by preparative HPLC to yield a light brown solid (29 mg; 30%). MS: m/z=474.1 [M+H]⁺.

Example 7

(2R,4S)-4-(2-Chloro-benzenesulfonyl)-1-(6-cyano-pyrazin-2-yl)-pyrrolidine-2-carboxylic acid ethyl Ester

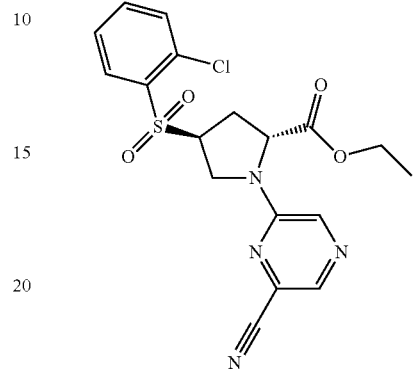

Example 7 was prepared in analogy to the methods described for example 1 and 2 starting from (2R,4R)-4-(toluene-4-sulfonyloxy)-pyrrolidine-1,2-dicarboxylic acid 1-tert-butyl ester 2-ethyl ester to yield an off-white solid. MS: m/z=421.1 [M+H]⁺.

Example 8

6-[(S)-3-(2-Chloro-benzenesulfonyl)-pyrrolidin-1-yl]-pyridine-2-carbonitrile

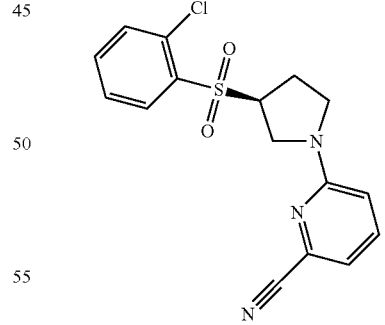

Example 8 was prepared in analogy to the methods described for example 1 and 2 starting from (R)-3-Hydroxy-pyrrolidine-1-carboxylic acid tert-butyl ester over (R)-3-(toluene-4-sulfonyloxy)-pyrrolidine-1-carboxylic acid tert-butyl ester to yield a light brown solid. MS: m/z=348.1 [M+H]⁺.

Example 9

6-[(S)-3-(2-Chloro-benzenesulfonyl)-pyrrolidin-1-yl]pyrazine-2-carbonitrile

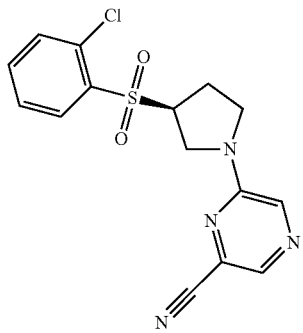 [SMILES: N#Cc1cncc(N2CC[C@H](S(=O)(=O)c3ccccc3Cl)C2)n1]

Example 9 was prepared in analogy to the methods described for example 1 and 2 starting from (R)-3-Hydroxy-pyrrolidine-1-carboxylic acid tert-butyl ester over (R)-3-(toluene-4-sulfonyloxy)-pyrrolidine-1-carboxylic acid tert-butyl ester to yield a amorphous brown solid. MS: m/z=349.1 [M+H]$^+$.

Example 10

6-[(2R,4S)-4-(2-Chloro-benzenesulfonyl)-2-(morpholine-4-carbonyl)-pyrrolidin-1-yl]-pyrazine-2-carbonitrile

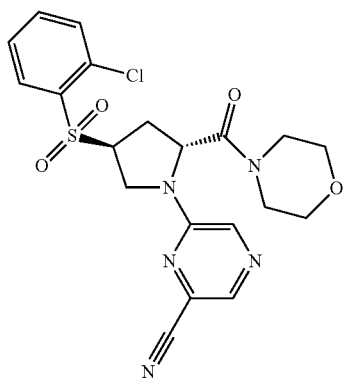 [SMILES: N#Cc1cncc(N2C[C@@H](S(=O)(=O)c3ccccc3Cl)C[C@@H]2C(=O)N2CCOCC2)n1]

Example 10 was prepared in analogy to the methods described for example 1 starting from (2R,4R)-4-(toluene-4-sulfonyloxy)-pyrrolidine-1,2-dicarboxylic acid 1-tert-butyl ester 2-ethyl ester to yield a brown solid. MS: m/z=462.2 [M+H]$^+$.

Example 11

(2R,4S)-4-(2-Chloro-benzenesulfonyl)-1-(6-cyano-pyrazin-2-yl)-pyrrolidine-2-carboxylic acid (2,2,2-trifluoro-ethyl)-amide

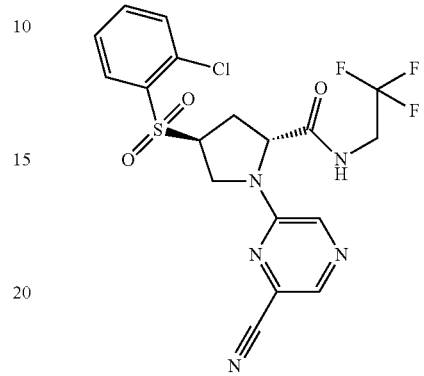

Example 10 was prepared in analogy to the methods described for example 6 starting from (2R,4R)-4-(toluene-4-sulfonyloxy)-pyrrolidine-1,2-dicarboxylic acid 1-tert-butyl ester 2-ethyl ester to yield a brown solid. MS: m/z=474.2 [M+H]$^+$.

Example 12

4-[(S)-3-(2-Chloro-benzenesulfonyl)-pyrrolidin-1-yl]pyrimidine-2-carbonitrile

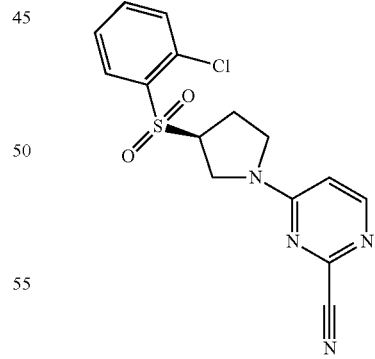

Example 12 was prepared in analogy to the methods described for example 1 starting from (R)-3-Hydroxy-pyrrolidine-1-carboxylic acid tert-butyl ester over (R)-3-(toluene-4-sulfonyloxy)-pyrrolidine-1-carboxylic acid tert-butyl ester with the exception of the last two reaction steps:

A) 2-Chloro-4-[(S)-3-(2-chloro-benzenesulfonyl)-pyrrolidin-1-yl]-pyrimidine

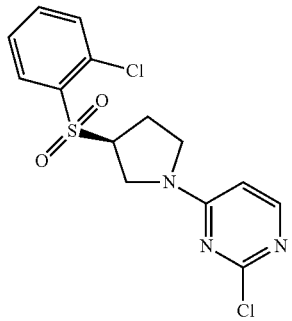 [SMILES: O=S(=O)(c1ccccc1Cl)[C@H]1CCN(c2ccnc(Cl)n2)C1]

(S)-3-(2-Chloro-benzenesulfonyl)-pyrrolidine TFA salt (250 mg) was dissolved in ACN (3.0 mL). 2,4-Dichloropyrimidine (155 mg), TEA (0.39 mL) and KF (4 mg) were added to the solution. The reaction mixture was stirred at 150° C. in the microwave oven for 2 h. The reaction mixture was evaporated to dryness and purified with preparative HPLC to yield 2-Chloro-4-[(S)-3-(2-chloro-benzenesulfonyl)-pyrrolidin-1-yl]-pyrimidine (91 mg, 36%) as a light yellow solid. MS: m/z=358.0 [M+H]$^+$.

B) 4-[(S)-3-(2-Chloro-benzenesulfonyl)-pyrrolidin-1-yl]-pyrimidine-2-carbonitrile

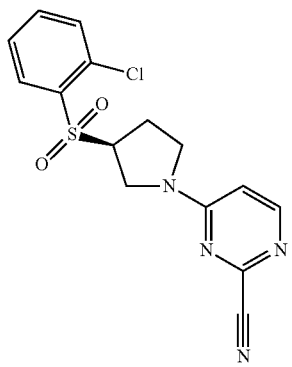 [SMILES: N#Cc1nccc(N2CC[C@H](S(=O)(=O)c3ccccc3Cl)C2)n1]

Example 12A (50 mg) was dissolved in DMSO/water (1.3 mL/0.2 mL). DABCO (31 mg) and KCN (18 mg) were added to the solution. The reaction mixture was now stirred at 80° C. for 4 h. After that, the reaction mixture was stirred at ambient temperature for 18 h. After that, the reaction mixture was again heated at 80° C. for 3 h. The reaction mixture was filtrated, evaporated to dryness and purified by preparative HPLC to yield the title compound (30 mg, 63%) as an off-white solid. MS: m/z=349.1 [M+H]$^+$.

Example 13

4-[(2R,4S)-4-(2-Chloro-benzenesulfonyl)-2-(5-methyl-[1,3,4]oxadiazol-2-yl)-pyrrolidin-1-yl]-pyrimidine-2-carbonitrile

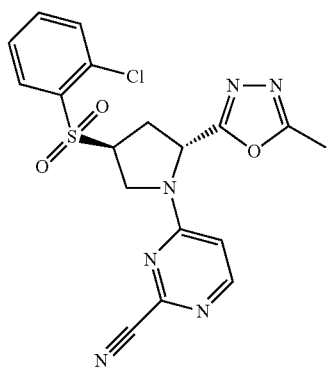 [SMILES: Cc1nnc([C@H]2C[C@H](S(=O)(=O)c3ccccc3Cl)CN2c2ccnc(C#N)n2)o1]

A) (2R,4S)-4-(2-Chloro-benzenesulfonyl)-pyrrolidine-1,2-dicarboxylic acid 1-tert-butyl ester 2-ethyl ester

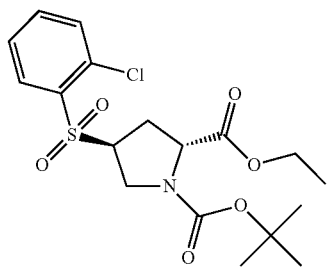 [SMILES: CCOC(=O)[C@H]1C[C@H](S(=O)(=O)c2ccccc2Cl)CN1C(=O)OC(C)(C)C]

Example 13A was prepared in analogy to example 1C starting from (2R,4R)-4-hydroxy-pyrrolidine-1,2-dicarboxylic acid 1-tert-butyl ester 2-ethyl ester to yield an off-white solid. MS: m/z=418.2; 362.0; 318.1 [M+H]$^+$.

B) (2R,4S)-4-(2-Chloro-benzenesulfonyl)-2-hydrazinocarbonyl-pyrrolidine-1-carboxylic acid test-butyl ester

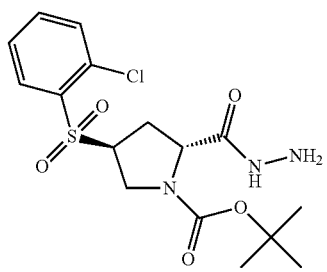 [SMILES: CC(C)(C)OC(=O)N1C[C@@H](S(=O)(=O)c2ccccc2Cl)C[C@@H]1C(=O)NN]

Example 13A (271 mg) was dissolved in ethanol (2.5 mL). Hydrazine hydrate (97 mg) was added and the reaction mixture was heated under reflux for three days. After that, the mixture was evaporated to dryness to yield a light yellow foam (250 mg; 95%). MS: m/z=304.1; 348.0; 404.2 [M+H]+.

C) (2R,4S)-4-(2-Chloro-benzenesulfonyl)-2-(5-methyl-[1,3,4]oxadiazol-2-yl)-pyrrolidine-1-carboxylic acid tert-butyl ester

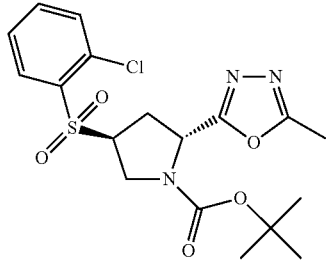 [SMILES: Cc1nnc([C@H]2C[C@H](S(=O)(=O)c3ccccc3Cl)CN2C(=O)OC(C)(C)C)o1]

Example 13B (250 mg) was dissolved in acetonitrile (3.5 mL) and acetic acid anhydride (79 mg) and DIEA (0.74 mL) were added. The reaction mixture was stirred for 3 h at 25° C. After that triphenyl phosphane (649 mg) and hexachloroethane (337 mg) were added. The reaction mixture was stirred for 18 h at 25° C. The reaction mixture was evaporated to dryness, dissolved in ethyl acetate (20 mL), extracted with water (10 mL) and brine (10 mL). The organic layers were dried over Na2SO4, filtrated and evaporated to dryness. The crude material was purified by flash chromatography using silica gel (20 g column) and ethyl acetate:n-heptane (0:1→1:0) to yield the title compound as a light yellow solid (164 mg; 62%). MS: m/z=428.1; 328.3 [M+H]+.

D) 2-[(2R,4S)-4-(2-Chloro-benzenesulfonyl)-pyrrolidin-2-yl]-5-methyl-[1,3,4]oxadiazole

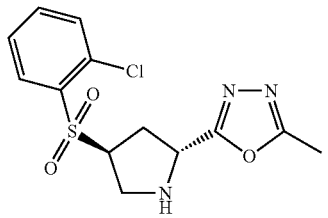 [SMILES: Cc1nnc([C@H]2C[C@H](S(=O)(=O)c3ccccc3Cl)CN2)o1]

Example 13C (164 mg) was dissolved in dichloromethane (1.5 mL) and TFA (1.5 mL) was subsequently added. The reaction mixture was stirred for 2 h at 25° C., evaporated to dryness, dissolved in dichloromethane and extracted with aqueous Na2CO3 solution and brine. The organic layers were dried over Na2SO4, filtrated and evaporated to dryness to yield a light brown solid (30 mg; 24%). MS: m/z=328.2 [M+H]+.

E) 2-Chloro-4-[(2R,4S)-4-(2-chloro-benzenesulfonyl)-2-(5-methyl-[1,3,4]oxadiazol-2-yl)-pyrrolidin-1-yl]-pyrimidine

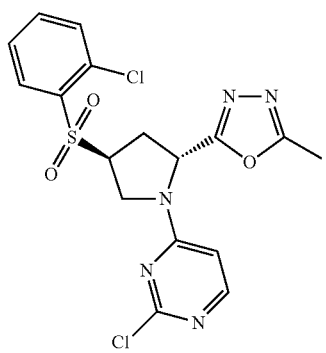 [SMILES: Cc1nnc([C@H]2C[C@H](S(=O)(=O)c3ccccc3Cl)CN2c2ccnc(Cl)n2)o1]

The title compound was prepared from 13D in analogy to example 12A to yield a yellow solid (29 mg; 72%). MS: m/z=440.1 [M+H]+.

F) 2-Chloro-4-[(2R,4S)-4-(2-chloro-benzenesulfonyl)-2-(5-methyl-[1,3,4]oxadiazol-2-yl)-pyrrolidin-1-yl]-pyrimidine

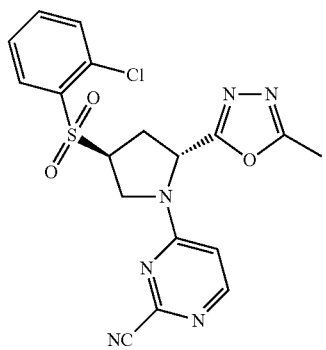 [SMILES: Cc1nnc([C@H]2C[C@H](S(=O)(=O)c3ccccc3Cl)CN2c2ccnc(C#N)n2)o1]

The title compound was prepared from example 13E in analogy to example 12B to yield an off-white solid (8 mg; 22%). MS: m/z=431.1 [M+H]+.

Example 14

4-[(S)-3-(2-Trifluoromethyl-benzenesulfonyl)-pyrrolidin-1-yl]pyrimidine-2-carbonitrile

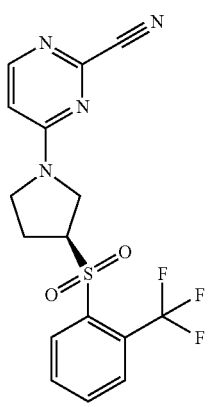 [SMILES: N#Cc1nccc(N2CC[C@H](S(=O)(=O)c3ccccc3C(F)(F)F)C2)n1]

Example 14 was prepared in analogy to example 12 to yield the title compound as a colorless amorphous solid (113 mg; 70%) MS: m/z=383.1 [M+H]$^{+s.}$

Example 15

4-[(2R,4S)-2-Hydroxymethyl-4-(2-trifluoromethyl-benzenesulfonyl)-pyrrolidin-1-yl]

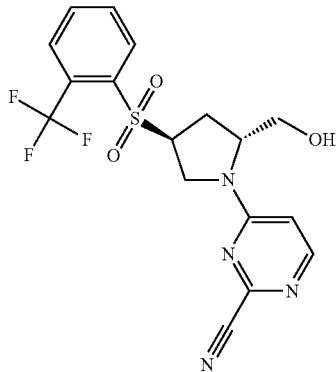 [SMILES: N#Cc1nccc(N2C[C@@H](S(=O)(=O)c3ccccc3C(F)(F)F)C[C@@H]2CO)n1]

A) (2R,4R)-2-[Dimethyl-(1,1,2-trimethyl-propyl)-silanyloxymethyl]-4-hydroxy-pyrrolidine-1-carboxylic acid tert-butyl ester

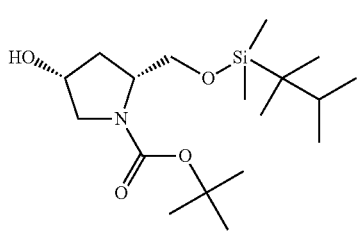 [SMILES: CC(C)C(C)(C)[Si](C)(C)OC[C@H]1C[C@@H](O)CN1C(=O)OC(C)(C)C]

(2R,4R)-4-Hydroxy-2-hydroxymethyl-pyrrolidine-1-carboxylic acid tert-butyl ester (3.8 g) was dissolved in DMF (25 mL). Imidazole (1.79 g) and thexyldimethylchlorosilane (3.75 g) were added dropwise at 0° C. After that, the reaction mixture was allowed to warm up to 25° C. The reaction mixture was then stirred at 25° C. for additional 3 h. The reaction mixture was then diluted with n-hexane (50 mL) and extracted with aqueous citric acid solution (10%, 50 mL) and brine (50 mL). The organic layers were dried over Na$_2$SO$_4$, filtrated and evaporated to dryness to yield a light brown oil (5.94 g; 94%). MS: m/z=360.3; 260.2 [M+H]$^+$.

B) (2R,4R)-2-[Dimethyl-(1,1,2-trimethyl-propyl)-silanyloxymethyl]-4-(3-nitro-benzenesulfonyloxy)-pyrrolidine-1-carboxylic acid tert-butyl ester

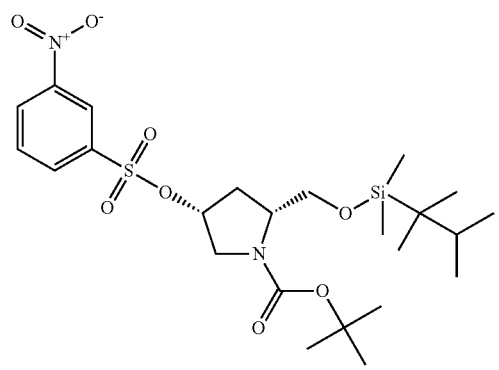 [SMILES: CC(C)C(C)(C)[Si](C)(C)OC[C@H]1C[C@@H](OS(=O)(=O)c2cccc([N+](=O)[O-])c2)CN1C(=O)OC(C)(C)C]

The title compound was prepared from example 15A (5.94 g) in analogy to the method described for example 1A to yield a brown oil (9.3 g; 99%) MS: m/z=545.3; 489.3; 445.4 [M+H]$^+$.

C) (2R,4S)-2-[Dimethyl-(1,1,2-trimethyl-propyl)-silanyloxymethyl]-4-(2-trifluoromethyl-benzenesulfonyl)-pyrrolidine-1-carboxylic acid tert-butyl ester

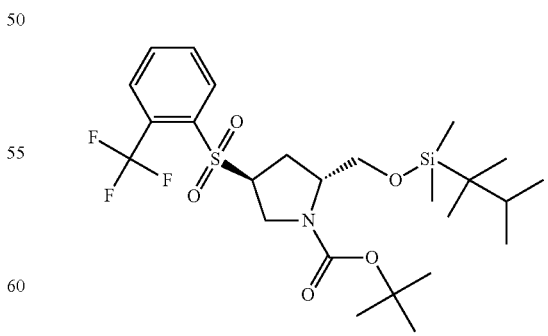

Example 15C was prepared from example 15B (9.3 g) in analogy to the methods described for example 1B and 1C to yield the title compound as a light yellow solid (2 steps, 7.4 g; 73% overall yield) MS: m/z=552.4; 496.2; 542.2 [M+H]

D) [(2R,4S)-4-(2-Trifluoromethyl-benzenesulfonyl)-pyrrolidin-2-yl]-methanol

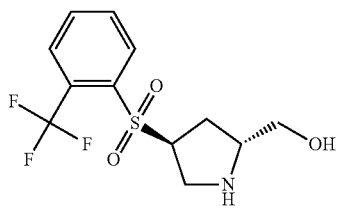 [SMILES: O=S(=O)(c1ccccc1C(F)(F)F)[C@@H]1CN[C@@H](CO)C1]

Example 15C (2 g) was dissolved in dichloromethane (15 mL). TFA (10 mL) was added and the reaction mixture was stirred for 18 h at 25° C. The reaction mixture was diluted with dichloromethane (25 mL) and extracted with aqueous Na$_2$CO$_3$ solution and brine. The organic layers were dried over Na$_2$SO$_4$, filtrated and evaporated to dryness to yield an off-white oil (654 mg; 58%). MS: m/z=310.2 [M+H]$^+$.

E) 4-[(2R,4S)-2-Hydroxymethyl-4-(2-trifluoromethyl-benzenesulfonyl)-pyrrolidin-1-yl]-pyrimidine-2-carbonitrile

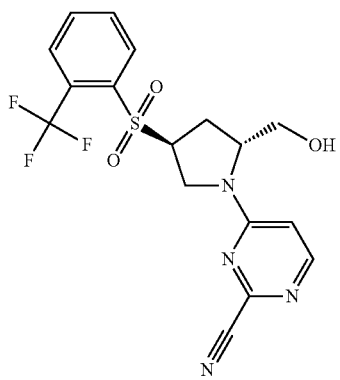

The title compound was prepared from example 15D (250 mg) in analogy to the methods described for examples 12A and 12B to yield a light yellow solid (2 steps, 47 mg; 35% overall yield) MS: m/z=413.2 [M+H]$^+$.

Example 16

4-Methyl-6-[(S)-3-(2-trifluoromethyl-benzenesulfonyl)-pyrrolidin-1-yl]-pyrimidine-2-carbonitrile

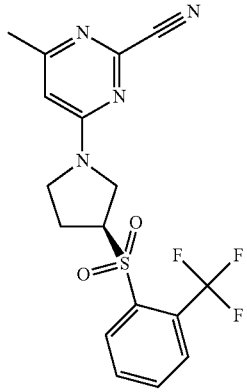 [SMILES: Cc1cc(N2CC[C@H](S(=O)(=O)c3ccccc3C(F)(F)F)C2)nc(C#N)n1]

The title compound was prepared in analogy to the methods described for example 12 to yield a colorless amorphous solid (72 mg; 61%) MS: m/z=397.1 [M+H]$^+$.

Example 17

5-Trifluoromethyl-4-[(S)-3-(2-trifluoromethyl-benzenesulfonyl)-pyrrolidin-1-yl]-pyrimidine-2-carbonitrile

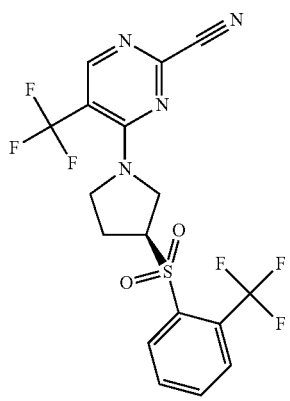 [SMILES: N#Cc1ncc(C(F)(F)F)c(N2CC[C@H](S(=O)(=O)c3ccccc3C(F)(F)F)C2)n1]

The title compound was prepared in analogy to the methods described for example 12 to yield a brown powder (48 mg; 25%) MS: m/z=451.1 [M+H]$^+$.

Example 18

5-Fluoro-4-[(S)-3-(2-trifluoromethyl-benzenesulfonyl)-pyrrolidin-1-yl]-pyrimidine-2-carbonitrile

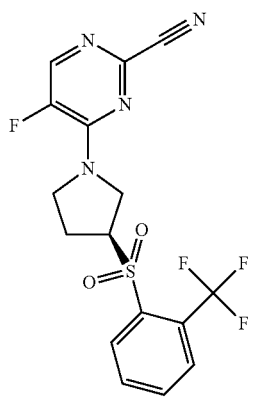 [SMILES: N#Cc1ncc(F)c(N2CC[C@H](S(=O)(=O)c3ccccc3C(F)(F)F)C2)n1]

The title compound was prepared in analogy to the methods described for example 12 to yield a light brown gum (22 mg; 28%) MS: m/z=401.1 [M+H]$^+$.

Example 19

5-Hydroxy-4-[(S)-3-(2-trifluoromethyl-benzene-sulfonyl)-pyrrolidin-1-yl]-pyrimidine-2-carbonitrile

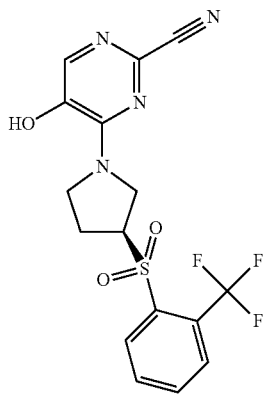 [SMILES: N#Cc1ncc(O)c(N2CC[C@H](S(=O)(=O)c3ccccc3C(F)(F)F)C2)n1]

The title compound was obtained as a by-product during the synthesis of example 18 (22 mg; 28%) MS: m/z=399.1 [M+H]$^+$.

Example 20

4-[(2R,4S)-2-Morpholin-4-ylmethyl-4-(2-trifluoromethyl-benzenesulfonyl)-pyrrolidin-1-yl]pyrimidine-2-carbonitrile

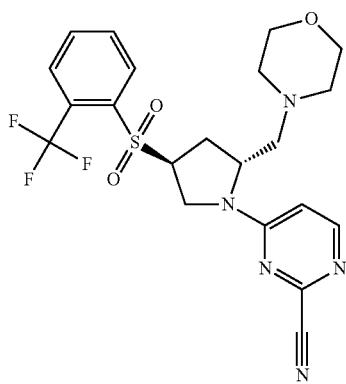 [SMILES: N#Cc1nccc(N2C[C@@H](S(=O)(=O)c3ccccc3C(F)(F)F)C[C@@H]2CN2CCOCC2)n1]

A) (2R,4S)-2-Hydroxymethyl-4-(2-trifluoromethyl-benzenesulfonyl)-pyrrolidine-1-carboxylic acid tert-butyl ester

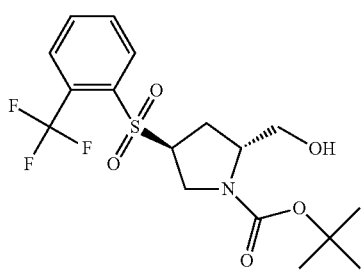 [SMILES: CC(C)(C)OC(=O)N1C[C@@H](S(=O)(=O)c2ccccc2C(F)(F)F)C[C@@H]1CO]

Example 15C (5.4 g) was dissolved in THF (55 mL) and TBAF hydrate (3.7 g) was added. The reaction mixture was stirred at 25° C. for 4 h. After that the reaction mixture was evaporated to dryness and purified by flash chromatography (200 g silica gel, ethyl acetate/n-heptane; 0:1→1:0) to yield the title compound as a light yellow oil (2.85 g; 71%) MS: m/z=410.2; 354.2; 310.2 [M+H]$^+$.

B) (2R,4S)-2-Methanesulfonyloxymethyl-4-(2-trifluoromethyl-benzenesulfonyl)-yrrolidine-1-carboxylic acid tert-butyl ester

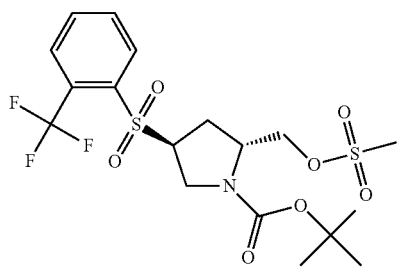 [SMILES: CC(C)(C)OC(=O)N1C[C@@H](S(=O)(=O)c2ccccc2C(F)(F)F)C[C@@H]1COS(C)(=O)=O]

Example 20A (800 mg) was dissolved in acetonitrile (8 mL). DIEA (0.4 mL) and methanesulfonyl chloride (0.18 mL) were added. The reaction mixture was stirred at 25° C. for 18 h. After that the reaction mixture was diluted with ethyl acetate (50 mL) and extracted with aqueous HCl solution (0.1 N; 10 mL), aqueous Na$_2$CO$_3$ solution (10 mL) and brine (10 mL). The organic layers were dried over Na$_2$SO$_4$, filtrated and evaporated to dryness to yield a light brown oil (977 mg; 100%). MS: m/z=388.1; 432.2 [M+H]$^+$.

C) (2R,4S)-2-Morpholin-4-ylmethyl-4-(2-trifluoromethyl-benzenesulfonyl)-pyrrolidine-1-carboxylic acid tert-butyl ester

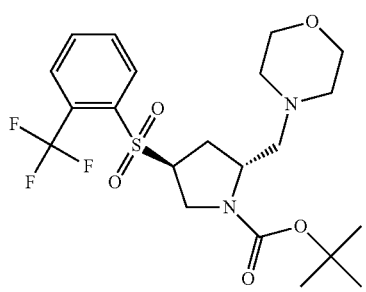 [SMILES: CC(C)(C)OC(=O)N1C[C@@H](S(=O)(=O)c2ccccc2C(F)(F)F)C[C@@H]1CN1CCOCC1]

Example 20B (488 mg) was dissolved in acetonitrile (5 mL). DIEA (0.2 mL) and morpholine (0.98 mL) were added. The reaction mixture was stirred at 25° C. for 18 h. After that the reaction mixture was stirred at 80° C. for 18 h. The reaction mixture was evaporated to dryness and purified by flash chromatography (20 g silica gel, ethyl acetate/n-heptane; 0:1→1:0) to yield the title compound as a light red solid (254 mg; 53%) MS: m/z=479.1; 423.2 [M+H]$^+$.

D) 4-[(2R,4S)-2-Morpholin-4-ylmethyl-4-(2-trifluoromethyl-benzenesulfonyl)-pyrrolidin-1-yl]-pyrimidine-2-carbonitrile

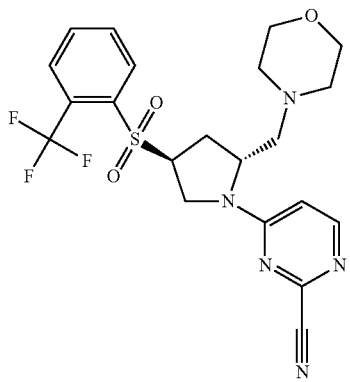 [SMILES: N#Cc1nccc(N2C[C@@H](S(=O)(=O)c3ccccc3C(F)(F)F)C[C@@H]2CN2CCOCC2)n1]

The title compound was prepared from example 20C (254 mg) in analogy to the methods described for example 12 to yield a white solid (21 mg; 50%) MS: m/z=482.1 [M+H]$^+$.

Example 21

2-[(2R,4S)-2-Morpholin-4-ylmethyl-4-(2-trifluoromethyl-benzenesulfonyl)-pyrrolidin-1-yl]-pyrimidine-4-carbonitrile

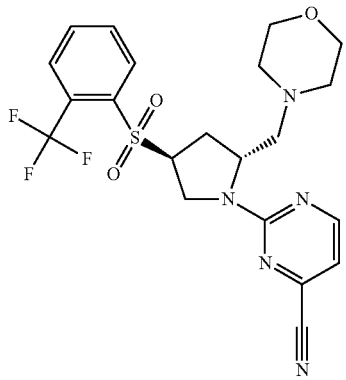 [SMILES: N#Cc1ccnc(N2C[C@@H](S(=O)(=O)c3ccccc3C(F)(F)F)C[C@@H]2CN2CCOCC2)n1]

The title compound was obtained as a by-product during the synthesis of example 20 to yield a white solid (4 mg; 30%) MS: m/z=482.2 [M+H]$^+$.

Example 22

4-[(2R,4S)-2-(3,3-Difluoro-pyrrolidin-1-ylmethyl)-4-(2-trifluoromethyl-benzenesulfonyl)-pyrrolidin-1-yl]-pyrimidine-2-carbonitrile

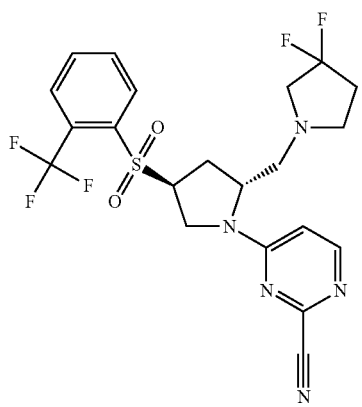 [SMILES: N#Cc1nccc(N2C[C@@H](S(=O)(=O)c3ccccc3C(F)(F)F)C[C@@H]2CN2CCC(F)(F)C2)n1]

The title compound was prepared in analogy to the methods described for example 20 to yield a white solid (15 mg; 46%) MS: m/z=502.1 [M+H]$^+$.

Example 23

4-[(S)-3-(2,3-Dichloro-benzenesulfonyl)-pyrrolidin-1-yl]-pyrimidine-2-carbonitrile

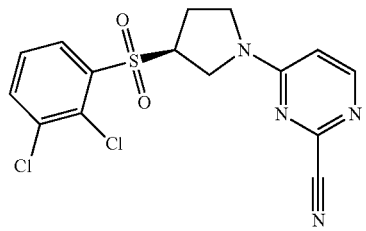 [SMILES: N#Cc1nccc(N2CC[C@H](S(=O)(=O)c3cccc(Cl)c3Cl)C2)n1]

The title compound was prepared in analogy to the methods described for example 12 to yield an off-white solid (25 mg; 28%) MS: m/z=383.1 [M+H]$^+$.

Example 24

4-[(R)-3-(2-Bromo-benzenesulfonyl)-pyrrolidin-1-yl]-pyrimidine-2-carbonitrile

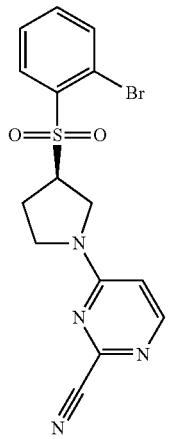 [SMILES: N#Cc1nccc(N2CC[C@@H](S(=O)(=O)c3ccccc3Br)C2)n1]

The title compound was prepared in analogy to the methods described for example 12 to yield a yellow solid (77 mg; 44%) MS: m/z=393.1 [M+H]+.

Example 25

4-[(S)-3-(3-Trifluoromethyl-benzenesulfonyl)-pyrrolidin-1-yl]-pyrimidine-2-carbonitrile

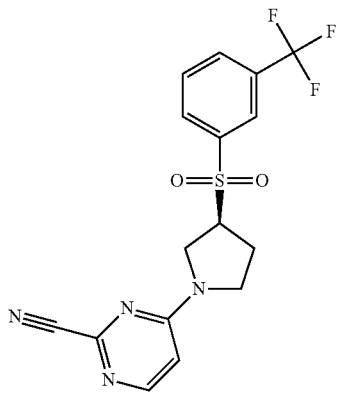 [SMILES: N#Cc1nccc(N2CC[C@H](S(=O)(=O)c3cccc(C(F)(F)F)c3)C2)n1]

The title compound was prepared in analogy to the methods described for example 12 to yield an off-white viscous oil (77 mg; 44%) MS: m/z=383.2 [M+H]+s.

Example 26

(2S,4S)-1-(2-Cyano-pyrimidin-4-yl)-4-(2-trifluoromethyl-benzenesulfonyl)-pyrrolidine-2-carboxylic acid (2,2,2-trifluoro-ethyl)-amide

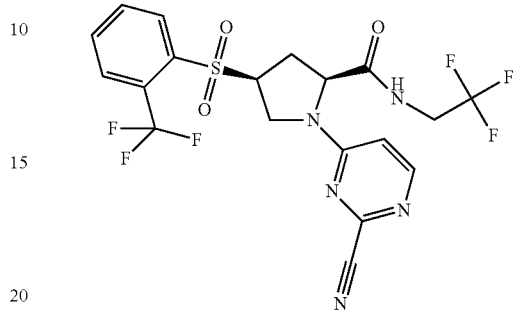

A) (2S,4S)-4-(2-Trifluoromethyl-benzenesulfonyl)-pyrrolidine-2-carboxylic acid methyl ester

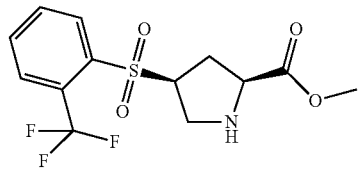 [SMILES: COC(=O)[C@@H]1C[C@H](S(=O)(=O)c2ccccc2C(F)(F)F)CN1]

Example 26A was prepared in analogy to example 2A to yield a colorless oil (2.07 g; 85%)

MS: m/z=338.2 [M+H]+.

B) (2S,4S)-1-(2-Chloro-pyrimidin-4-yl)-4-(2-trifluoromethyl-benzenesulfonyl)-pyrrolidine-2-carboxylic acid methyl ester

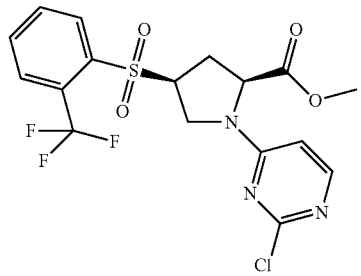 [SMILES: COC(=O)[C@@H]1C[C@H](S(=O)(=O)c2ccccc2C(F)(F)F)CN1c1ccnc(Cl)n1]

Example 26A (2.07 g) was dissolved in acetonitrile (10 mL). 2,6-Dichloro pyrimidine (1.01 g), TEA (2.57 mL) and KF (36 mg) were added to the mixture in a sealed tube. The mixture was heated in a microwave oven at 150° C. for 1.5 h. The reaction mixture was evaporated to dryness and purified by flash chromatography (50 g silica gel, ethyl acetate/n-heptane; 0:1→1:0) to yield a light brown solid (660 mg; 24%) MS: m/z=450.1 [M+H]+.

C) Lithium; (2S,4S)-1-(2-chloro-pyrimidin-4-yl)-4-(2-trifluoromethyl-benzenesulfonyl)-pyrrolidine-2-carboxylate

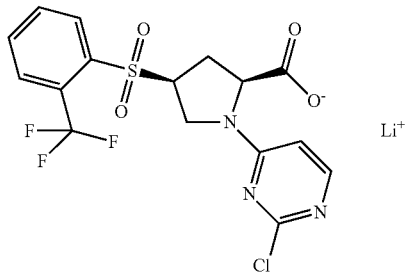 [SMILES: O=C([O-])[C@@H]1C[C@H](S(=O)(=O)c2ccccc2C(F)(F)F)CN1c1ccnc(Cl)n1 ; [Li+]]

Example 26B (580 mg) was dissolved in THF/water (4.5 mL/1.0 mL). Lithium hydroxide dihydrate (60 mg) was added to the solution. The obtained suspension was stirred at 25° C. for 2.5 h. After that water (1 mL) was added and the obtained solution was stirred for additional 3.5 h. After that additional lithium hydroxide dihydrate (11 mg) was added to the solution and the mixture was stirred for 18 h at 25° C. The reaction mixture was then evaporated to dryness to yield 590 mg (104%) of the salt. Example 26C was used without further purification for the next steps. MS: m/z=436.2 [M+H]$^+$.

D) (2S,4S)-1-(2-Chloro-pyrimidin-4-yl)-4-(2-trifluoromethyl-benzenesulfonyl)-pyrrolidine-2-carboxylic acid (2,2,2-trifluoro-ethyl)-amide

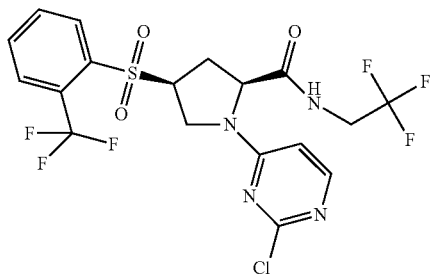 [SMILES: O=C(NCC(F)(F)F)[C@@H]1C[C@H](S(=O)(=O)c2ccccc2C(F)(F)F)CN1c1ccnc(Cl)n1]

Example 26C (147 mg) was dissolved in acetonitrile (2.0 mL). DIEA (0.17 mL), HATU (77 mg) and EDCI (96 mg) were added to the mixture. After 30 min 2,2,2-trifluoroethylamine hydrochloride (68 mg) was added. The mixture was stirred for 18 h at 25° C. After that, the reaction mixture was evaporated to dryness, dissolved in ethyl acetate (20 mL) and extracted with aqueous Na$_2$CO$_3$ solution (10%; 10 mL) and aqueous HCl solution (0.1 N; 10 mL) and brine (10 mL). The organic layers were dried over Na$_2$SO$_4$ and filtrated and evaporated to dryness to yield a light brown oil (93 mg; 54%). MS: m/z=517.2 [M+H]$^+$.

E) (2S,4S)-1-(2-Cyano-pyrimidin-4-yl)-4-(2-trifluoromethyl-benzenesulfonyl)-pyrrolidine-2-carboxylic acid (2,2,2-trifluoro-ethyl)-amide

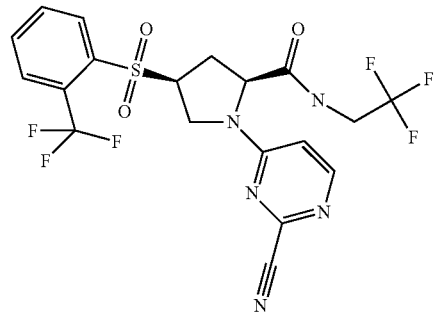 [SMILES: N#Cc1nccc(N2C[C@@H](S(=O)(=O)c3ccccc3C(F)(F)F)C[C@H]2C(=O)NCC(F)(F)F)n1]

Example 26D (93 mg) was dissolved in DMSO (1.7 mL) and DABCO (40 mg) and KCN (23 mg) were added. After that, water (0.3 mL) was added and the reaction mixture was stirred at 80° C. for 18 h. The reaction mixture was filtrated and purified by preparative HPLC to yield the title compound as a white solid (22 mg; 24%). MS: m/z=508.2 [M+H]$^+$.

Example 27

4-[(2S,4S)-2-(Azetidine-1-carbonyl)-4-(2-trifluoromethyl-benzenesulfonyl)-pyrrolidin-1-yl]-pyrimidine-2-carbonitrile

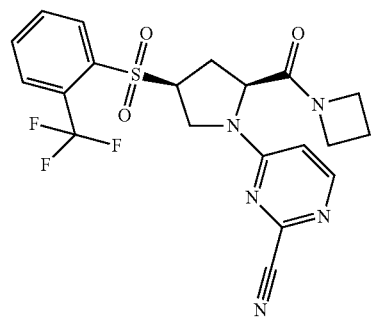 [SMILES: N#Cc1nccc(N2C[C@@H](S(=O)(=O)c3ccccc3C(F)(F)F)C[C@H]2C(=O)N2CCC2)n1]

Example 27 was prepared in analogy to the methods described for example 26 to yield the title compound as a light brown oil (26 mg; 27%). MS: m/z=466.3 [M+H]$^+$.

Example 28

(2S,4S)-1-(2-Cyano-pyrimidin-4-yl)-4-(2-trifluoromethyl-benzenesulfonyl)-pyrrolidine-2-carboxylic acid ((S)-2,2,2-trifluoro-1-methyl-ethyl)-amide

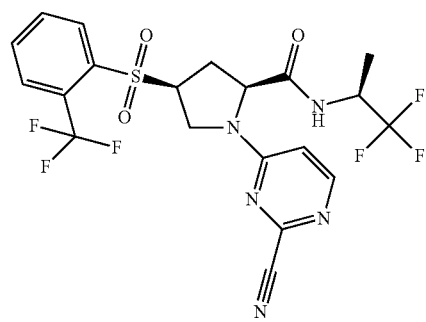 [SMILES: C[C@H](NC(=O)[C@@H]1C[C@H](S(=O)(=O)c2ccccc2C(F)(F)F)CN1c1ccnc(C#N)n1)C(F)(F)F]

Example 28 was prepared in analogy to the methods described for example 26 to yield the title compound as a yellow solid (18 mg; 15%). MS: m/z=522.2 [M+H]+.

Example 29

(2S,4S)-1-(2-Cyano-pyrimidin-4-yl)-4-(2-trifluoromethyl-benzenesulfonyl)-pyrrolidine-2-carboxylic acid diethylamide

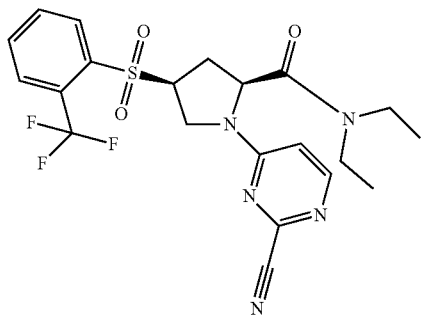 [SMILES: CCN(CC)C(=O)[C@@H]1C[C@H](S(=O)(=O)c2ccccc2C(F)(F)F)CN1c1ccnc(C#N)n1]

Example 29 was prepared in analogy to the methods described for example 26 to yield the title compound as a light yellow solid (14 mg; 17%). MS: m/z=482.3 [M+H]+.

Example 30

(2S,4S)-1-(2-Cyano-pyrimidin-4-yl)-4-(2-trifluoromethyl-benzenesulfonyl)-pyrrolidine-2-carboxylic acid

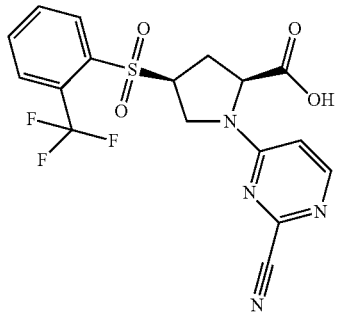 [SMILES: N#Cc1nccc(N2C[C@@H](S(=O)(=O)c3ccccc3C(F)(F)F)C[C@H]2C(=O)O)n1]

Example 30 was prepared from example 26B (80 mg) using the method described for example 26E to yield the title compound as a yellow amorphous solid (11 mg; 15%).

MS: m/z=427.1 [M+H]+.

Example 31

(2S,4S)-1-(2-Cyano-pyrimidin-4-yl)-4-(2-trifluoromethyl-benzenesulfonyl)-pyrrolidine-2-carboxylic acid amide

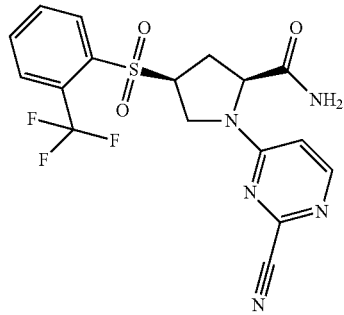 [SMILES: N#Cc1nccc(N2C[C@@H](S(=O)(=O)c3ccccc3C(F)(F)F)C[C@H]2C(N)=O)n1]

A) (2S,4S)-1-(2-Chloro-pyrimidin-4-yl)-4-(2-trifluoromethyl-benzenesulfonyl)-pyrrolidine-2-carboxylic acid amide

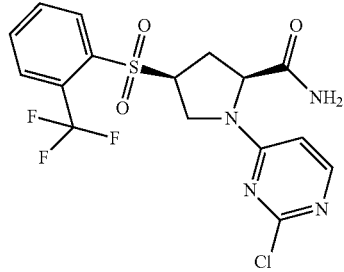 [SMILES: NC(=O)[C@@H]1C[C@H](S(=O)(=O)c2ccccc2C(F)(F)F)CN1c1ccnc(Cl)n1]

Example 26C (75 mg) was dissolved in acetonitrile (2.0 mL) and di-tert.-butyl-dicarbonat (48 mg) was added. After that, pyridine (0.01 mL) and ammonium bicarbonate (17 mg) were added. The reaction mixture was then stirred for 3 d at 25° C. After that, additional ammonium bicarbonate (8 mg) and di-tert.-butyl-dicarbonat (24 mg) were added. The reaction mixture was stirred at reflux for 18 h. After that, further ammonium bicarbonate (17 mg) and di-tert.-butyl-dicarbonat (48 mg) were added and the reaction mixture was refluxed for additional 18 h. After that, the reaction mixture was diluted with ethyl acetate (20 mL) and extracted with aqueous Na$_2$CO$_3$ (10%; 10 mL) and brine (10 mL). The organic layers were dired over Na$_2$SO$_4$, filtrated and evaporated to dryness to yield example 31A as a light brown oil (56 mg, 76%) which was used without further purification. MS: m/z=435.3 [M+H]+.

B) (2S,4S)-1-(2-Cyano-pyrimidin-4-yl)-4-(2-trifluoromethyl-benzenesulfonyl)-pyrrolidine-2-carboxylic acid amide

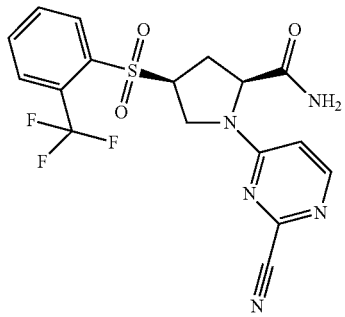

Example 31B was prepared in analogy to the method described for example 26E to yield the title compound as off-white solid (13 mg; 24%). MS: m/z=426.2 [M+H]+.

Example 32

(2S,4S)-1-(2-Cyano-pyrimidin-4-yl)-4-(2-trifluoromethyl-benzenesulfonyl)-pyrrolidine-2-carboxylic acid ethylamide

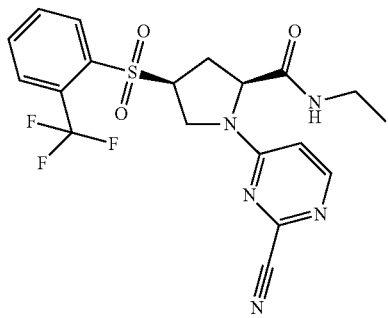 [SMILES: CCNC(=O)[C@@H]1C[C@H](S(=O)(=O)c2ccccc2C(F)(F)F)CN1c1ccnc(C#N)n1]

Example 32 was prepared in analogy to the methods described for example 26 to yield the title compound as a light yellow amorphous material (13 mg; 27%). MS: m/z=454.2 [M+H]+.

Example 33

(2S,4S)-1-(2-Cyano-pyrimidin-4-yl)-4-(2-trifluoromethyl-benzenesulfonyl)-pyrrolidine-2-carboxylic acid cyanomethyl-amide

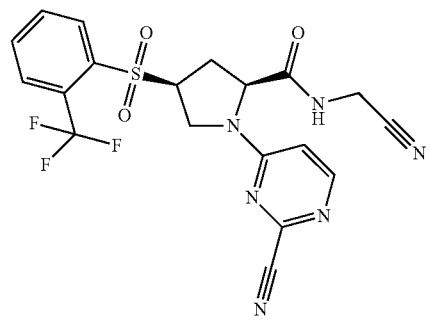 [SMILES: N#CCNC(=O)[C@@H]1C[C@H](S(=O)(=O)c2ccccc2C(F)(F)F)CN1c1ccnc(C#N)n1]

Example 33 was prepared in analogy to the methods described for example 26 to yield the title compound as an off-white solid (23 mg; 43%). MS: m/z=465.1 [M+H]+.

Example 34

4-[(2S,4S)-2-(3,3-Difluoro-pyrrolidine-1-carbonyl)-4-(2-trifluoromethyl-benzenesulfonyl)-pyrrolidin-1-yl]pyrimidine-2-carbonitrile

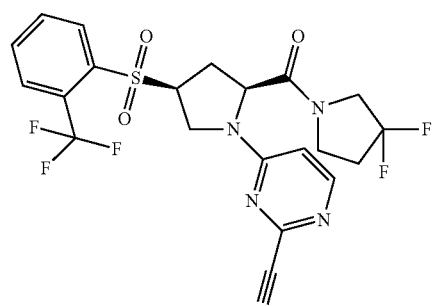

Example 34 was prepared in analogy to the methods described for example 26 to yield the title compound as a light yellow amorphous material (25 mg; 29%). MS: m/z=516.4 [M+H]+.

Example 35

(2S,4S)-1-(2-Cyano-pyrimidin-4-yl)-4-(2-trifluoromethyl-benzenesulfonyl)-pyrrolidine-2-carboxylic acid 4-fluoro-benzylamide

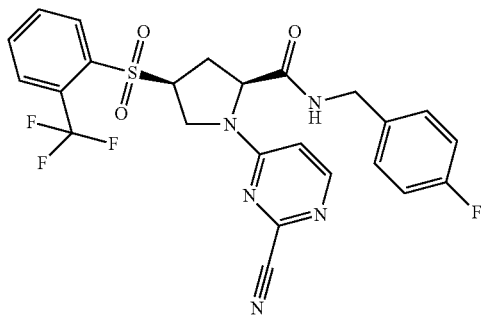 [SMILES: N#Cc1nccc(N2C[C@@H](S(=O)(=O)c3ccccc3C(F)(F)F)C[C@H]2C(=O)NCc2ccc(F)cc2)n1]

Example 35 was prepared in analogy to the methods described for example 26 to yield the title compound as a light yellow solid (19 mg; 22%). MS: m/z=534.2 [M+H]⁺.

Example 36

(2S,4S)-1-(2-Cyano-pyrimidin-4-yl)-4-(2-trifluoromethyl-benzenesulfonyl)-pyrrolidine-2-carboxylic acid (1-cyano-cyclopropyl)-amide

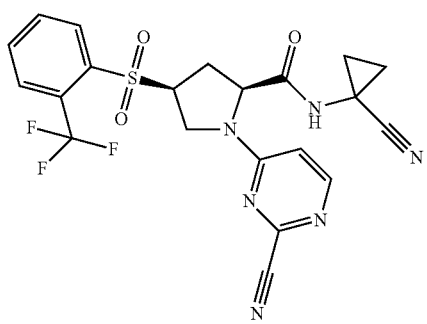 [SMILES: N#Cc1nccc(N2C[C@@H](S(=O)(=O)c3ccccc3C(F)(F)F)C[C@H]2C(=O)NC2(C#N)CC2)n1]

Example 36 was prepared in analogy to the methods described for example 26 to yield the title compound as a white solid (20 mg; 27%). MS: m/z=491.2 [M+H]⁺.

Example 37

(2S,4S)-1-(2-Cyano-pyrimidin-4-yl)-4-(2-trifluoromethyl-benzenesulfonyl)-pyrrolidine-2-carboxylic acid isopropylamide

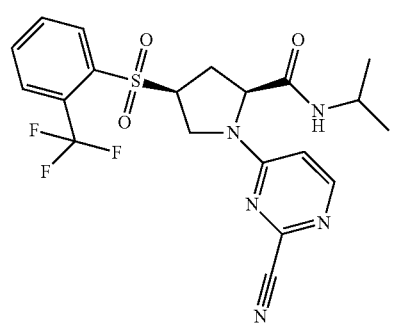 [SMILES: CC(C)NC(=O)[C@@H]1C[C@H](S(=O)(=O)c2ccccc2C(F)(F)F)CN1c1ccnc(C#N)n1]

Example 32 was prepared in analogy to the methods described for example 26 to yield the title compound as an off-white solid (7 mg; 27%). MS: m/z=468.2 [M+H]⁺.

Example 38

4-[(S)-3-(2-Trifluoromethyl-benzenesulfonyl)-pyrrolidin-1-yl]-6,7-dihydro-5H-cyclopentapyrimidine-2-carbonitrile

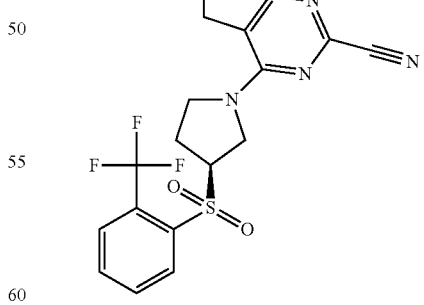

The title compound was prepared in analogy to the methods described for example 12 to yield a light yellow solid (17 mg; 7%) MS: m/z=423.2 [M+H]⁺.

Example 39

5-Methyl-4-[(S)-3-(2-trifluoromethyl-benzenesulfonyl)-pyrrolidin-1-yl]-pyrimidine-2-carbonitrile

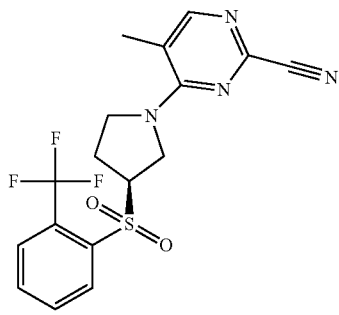 [SMILES: Cc1cnc(C#N)nc1N1CC[C@H](S(=O)(=O)c2ccccc2C(F)(F)F)C1]

The title compound was prepared in analogy to the methods described for example 12 to yield a brown solid (13 mg; 26%) MS: m/z=397.2 [M+H]$^+$.

Example 40

4-Trifluoromethyl-6-[(S)-3-(2-trifluoromethyl-benzenesulfonyl)-pyrrolidin-1-yl]-pyrimidine-2-carbonitrile

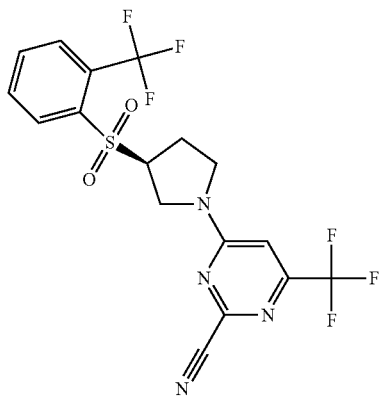 [SMILES: N#Cc1nc(N2CC[C@H](S(=O)(=O)c3ccccc3C(F)(F)F)C2)cc(C(F)(F)F)n1]

A) 2-Methylsulfanyl-4-trifluoromethyl-6-[(S)-3-(2-trifluoromethyl-benzenesulfonyl)-pyrrolidin-1-yl]-pyrimidine

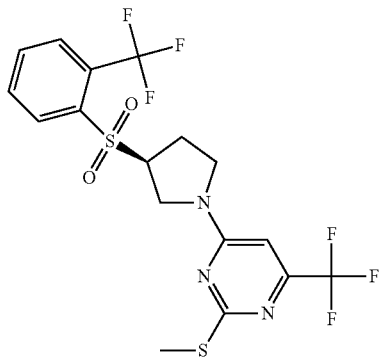 [SMILES: CSc1nc(N2CC[C@H](S(=O)(=O)c3ccccc3C(F)(F)F)C2)cc(C(F)(F)F)n1]

(S)-3-(2-Trifluoromethyl-benzenesulfonyl)-pyrrolidine (500 mg) was dissolved in acetonitrile (3.5 mL) in a microwave tube. 4-Chloro-2-(methylsulfanyl)-6-(trifluoromethyl) pyrimidine (450 mg), TEA (0.75 mL) and KF (10 mg) were added. The reaction mixture was irradiated in the microwave oven at 150° C. for 1.5 h. The reaction mixture was evaporated to dryness and purified by flash chromatography (50 g silica gel, ethyl acetate/n-heptane:0:1→1:0) to yield a light yellow oil (790 mg; 94%) MS: m/z=472.2 [M+H]$^+$.

B) 2-Methanesulfonyl-4-trifluoromethyl-6-[(S)-3-(2-trifluoromethyl-benzenesulfonyl)-pyrrolidin-1-yl]-pyrimidine

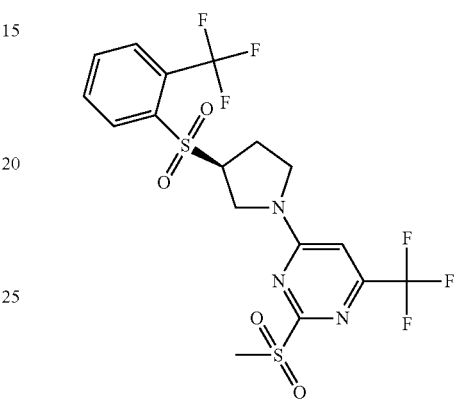

Example 40A (790 mg) was dissolved in dichloromethane (10 mL) and cooled to 0° C. After that MCPBA hydrate (496 mg) was carefully added. The reaction mixture was stirred at 25° C. for 2 h. After that the reaction mixture was diluted with dichloromethane (20 mL) and extracted with aqueous Na$_2$CO$_3$ solution (10%, 10 mL) and brine (10 mL). The organic layers were dired over Na$_2$SO$_4$, filtrated and evaporated to dryness to yield a yellow oil (930 mg; 110%) which was used for the next step without purification. MS: m/z=504.1 [M+H]$^+$.

C) 4-Trifluoromethyl-6-[(S)-3-(2-trifluoromethyl-benzenesulfonyl)-pyrrolidin-1-yl]-pyrimidine-2-carbonitrile

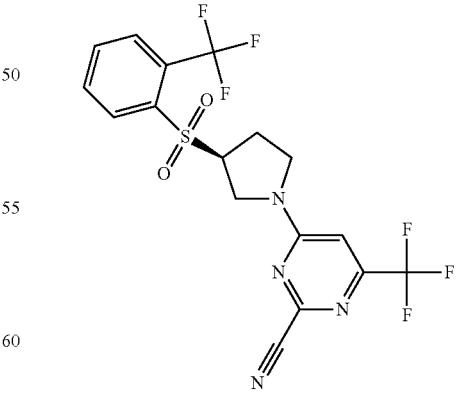

Example 40B (930 mg) was dissolved in DMSO/water (5.0 mL/1.0 mL) and NaCN (91 mg) was added. The reaction mixture was stirred at 25° C. for 18 h. After that the reaction mixture was diluted with ethyl acetate (20 mL) and extracted Example 41

(S)-1-(2-Cyano-6-trifluoromethyl-pyrimidin-4-yl)-4-(2-trifluoromethyl-benzenesulfonyl)-pyrrolidine-2-carboxylic acid amide

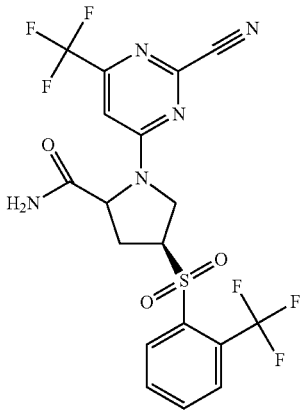 [SMILES: N#Cc1nc(N2C[C@@H](S(=O)(=O)c3ccccc3C(F)(F)F)CC2C(N)=O)cc(C(F)(F)F)n1]

Example 41 was prepared in analogy to the methods described for examples 31A and 40 to yield a white solid (81 mg; 24%). Epimerization of the amide residue occurred at the last synthesis step. MS: m/z=494.1 [M+H]+.

Example 42

4-[(S)-3-(2-Chloro-4-fluoro-benzenesulfonyl)-pyrrolidin-1-yl]-6-trifluoromethyl-pyrimidine-2-carbonitrile

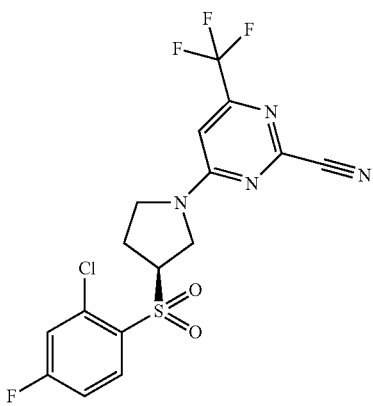 [SMILES: N#Cc1nc(N2CC[C@H](S(=O)(=O)c3ccc(F)cc3Cl)C2)cc(C(F)(F)F)n1]

Example 42 was prepared in analogy to the methods described for example 40 to yield a yellow solid (50 mg; 45%). MS: m/z=435.3 [M+H]+.

Example 43

4-{(S)-3-[2-Chloro-4-(4-methyl-piperazin-1-yl)-benzenesulfonyl]-pyrrolidin-1-yl}-6-trifluoromethyl-pyrimidine-2-carbonitrile

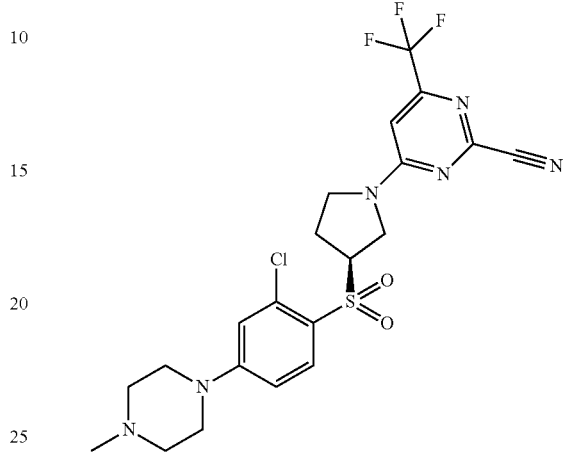

Example 42 (50 mg) was dissolved in acetonitrile (2.0 mL). DIEA (0.04 mL) and 1-methylpiperazine (0.03 mL) were added. The reaction mixture was stirred at 25° C. for 4 h. After that, 1-methylpiperazine (0.04 mL) was added and the mixture was stirred at 25° C. for 24 h. The reaction mixture was then purified by preparative HPLC to yield the title compound as an off-white solid (33 mg; 56%). MS: m/z=515.4 [M+H]+.

Example 44

4-{(S)-3-[4-(4-tert-Butyl-piperazin-1-yl)-2-chloro-benzenesulfonyl]-pyrrolidin-1-yl}-6-trifluoromethyl-pyrimidine-2-carbonitrile; compound with formic acid

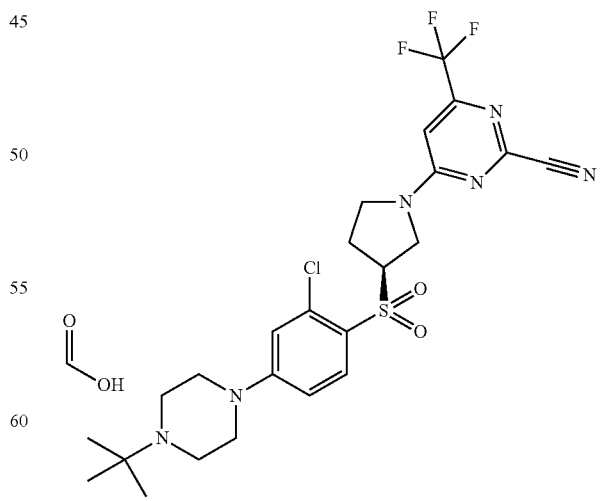

Example 44 was prepared in analogy to the methods described for example 43 to yield a light brown foam (87 mg; 63%). MS: m/z=557.3 [M+H]+.

Example 45

4-[(S)-3-((S)-2-Chloro-4-hexahydro-pyrrolo[1,2-a]pyrazin-2-yl-benzenesulfonyl)-pyrrolidin-1-yl]-6-trifluoromethyl-pyrimidine-2-carbonitrile; compound with formic acid

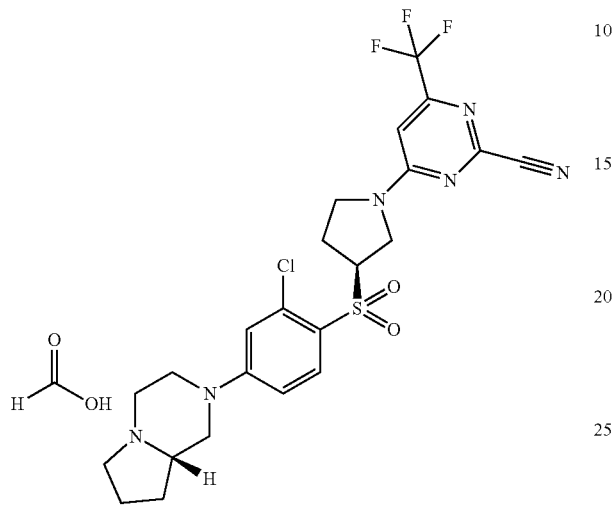

Example 45 was prepared in analogy to the methods described for example 43 to yield a light brown solid (71 mg; 53%). MS: m/z=541.4 [M+H]$^+$.

Example 46

4-{(S)-3-[2-Chloro-4-((S)-2,2,2-trifluoro-1-methyl-ethoxy)-benzenesulfonyl]-pyrrolidin-1-yl}-6-trifluoromethyl-pyrimidine-2-carbonitrile

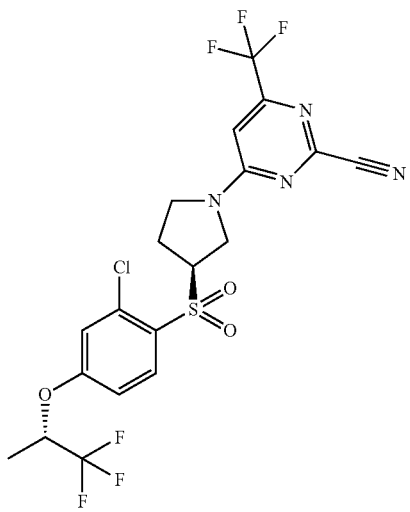 [SMILES: C[C@H](Oc1ccc(S(=O)(=O)[C@H]2CCN(c3cc(C(F)(F)F)nc(C#N)n3)C2)c(Cl)c1)C(F)(F)F]

Example 42 (100 mg) was dissolved in DMA (2 mL). Cesium carbonate (150 mg) and (S)-trifluoroisopropanol (52 mg) were added. The reaction mixture was stirred in the microwave oven for 30 min at 80° C. The reaction mixture was purified with preparative HPLC to yield a colorless solid (27 mg; 22%). MS: m/z=529.1 [M+H]$^+$.

Example 47

4-[(S)-3-(2-Chloro-4-pyrazol-1-yl-benzenesulfonyl)-pyrrolidin-1-yl]-6-trifluoromethyl-pyrimidine-2-carbonitrile

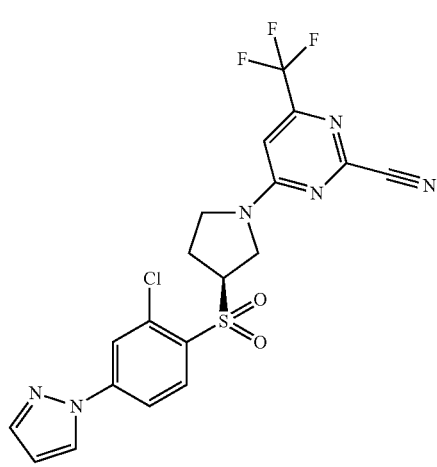 [SMILES: N#Cc1nc(N2CC[C@H](S(=O)(=O)c3ccc(-n4cccn4)cc3Cl)C2)cc(C(F)(F)F)n1]

Example 47 was prepared in analogy to the methods described for example 46 to yield a colorless solid (21 mg; 21%). MS: m/z=483.1 [M+H]$^+$.

Example 48

4-{(S)-3-[2-Chloro-4-(4-cyclopropyl-piperazin-1-yl)-benzenesulfonyl]-pyrrolidin-1-yl}-6-trifluoromethyl-pyrimidine-2-carbonitrile

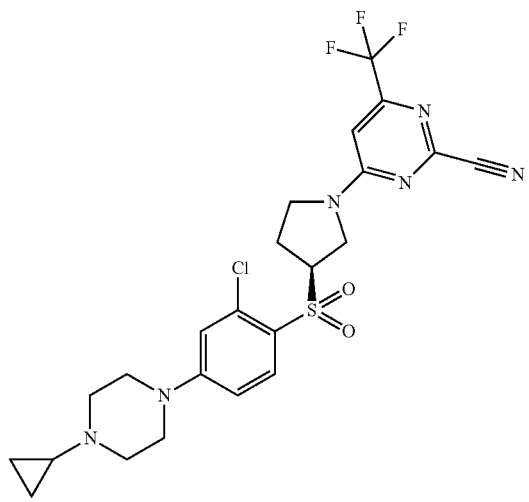 [SMILES: N#Cc1nc(N2CC[C@H](S(=O)(=O)c3ccc(N4CCN(C5CC5)CC4)cc3Cl)C2)cc(C(F)(F)F)n1]

Example 48 was prepared in analogy to the methods described for example 43 to yield a white solid (14 mg; 11%). MS: m/z=541.4 [M+H]$^+$.

Example 49

4-{(S)-3-[2-Chloro-4-(2,2,2-trifluoro-ethoxy)-benzenesulfonyl]-pyrrolidin-1-yl}-6-trifluoromethyl-pyrimidine-2-carbonitrile

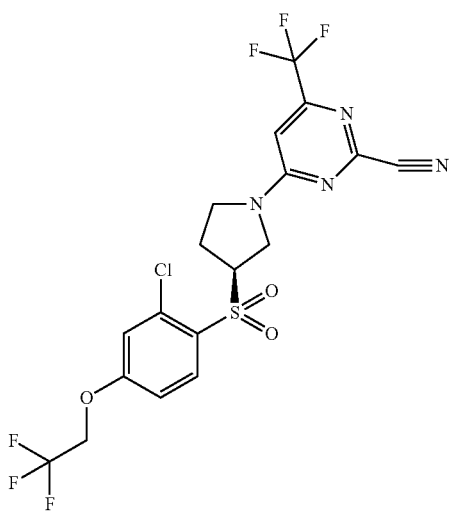 [SMILES: N#Cc1nc(N2CC[C@H](S(=O)(=O)c3ccc(OCC(F)(F)F)cc3Cl)C2)cc(C(F)(F)F)n1]

Example 49 was prepared in analogy to the methods described for example 46 to yield a white solid (14 mg; 12%). MS: m/z=515.3 [M+H]$^+$.

Example 50

4-[(S)-3-(2-Chloro-4-imidazol-1-yl-benzenesulfonyl)-pyrrolidin-1-yl]-6-trifluoromethyl-pyrimidine-2-carbonitrile

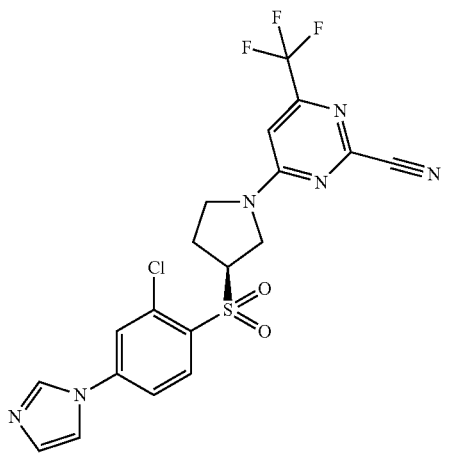 [SMILES: N#Cc1nc(N2CC[C@H](S(=O)(=O)c3ccc(-n4ccnc4)cc3Cl)C2)cc(C(F)(F)F)n1]

Example 50 was prepared in analogy to the methods described for example 46 with the exception that the mixture was heated for 3 d at 80° C. to yield a colorless solid (51 mg; 46%). MS: m/z=483.1 [M+H]$^+$.

Example 51

4-{(S)-3-[2-Chloro-4-(2-methoxy-ethoxy)-benzenesulfonyl]-pyrrolidin-1-yl}-6-trifluoromethyl-pyrimidine-2-carbonitrile A) 4-{(S)-3-[2-Chloro-4-(2-methoxy-ethoxy)-benzenesulfonyl]-pyrrolidin-1-yl}-2-methylsulfanyl-6-trifluoromethyl-pyrimidine

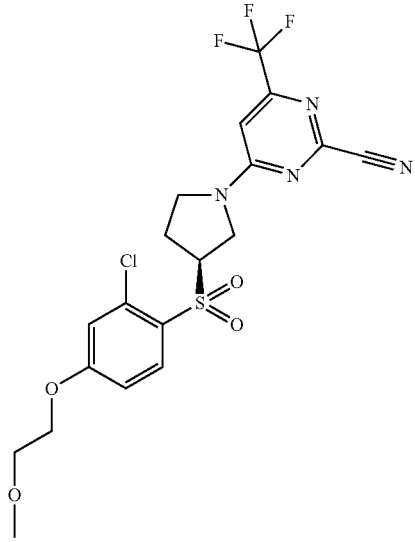 [SMILES: COCCOc1ccc(S(=O)(=O)[C@H]2CCN(c3cc(C(F)(F)F)nc(C#N)n3)C2)c(Cl)c1]

4-[(S)-3-(2-Chloro-4-fluoro-benzenesulfonyl)-pyrrolidin-1-yl]-2-methylsulfanyl-6-trifluoromethyl-pyrimidine (Intermediate of example 42; 300 mg) was dissolved in DMF (5.0 mL). Cs$_2$CO$_3$ (429 mg) and 2-methoxy-ethanol (0.10 mL) were added. The reaction mixture was stirred for 24 h at 25° C. After that, the reaction mixture was diluted with ethyl acetate (20 mL) and extracted with water (10 mL). The organic layers were dried over Na$_2$SO$_4$, filtrated and evaporated to dryness. The crude material was purified by flash chromatography (50 g silica gel; ethyl acetate/n-heptane) to yield a colorless waxy solid (170 mg; 50%) MS: m/z=512.2 [M+H]+.

B) 4-{(S)-3-[2-Chloro-4-(2-methoxy-ethoxy)-benzenesulfonyl]-pyrrolidin-1-yl}-2-methanesulfonyl-6-trifluoromethyl-pyrimidine

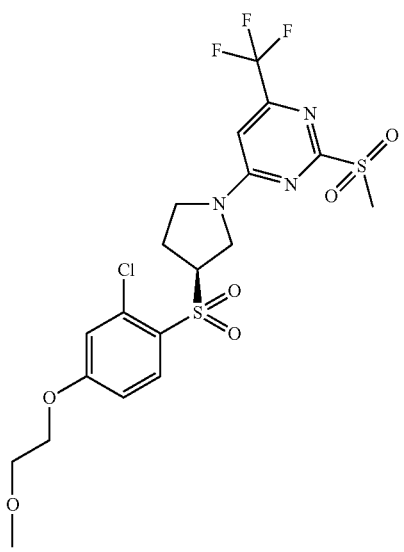 [SMILES: COCCOc1ccc(S(=O)(=O)[C@H]2CCN(c3cc(C(F)(F)F)nc(S(C)(=O)=O)n3)C2)c(Cl)c1]

Example 51B was prepared in analogy to the methods described for example 40B to yield a white foam (158 mg; 87%). MS: m/z=544.2 [M+H]+.

C) 4-{(S)-3-[2-Chloro-4-(2-methoxy-ethoxy)-benzenesulfonyl]-pyrrolidin-1-yl}-6-trifluoromethyl-pyrimidine-2-carbonitrile

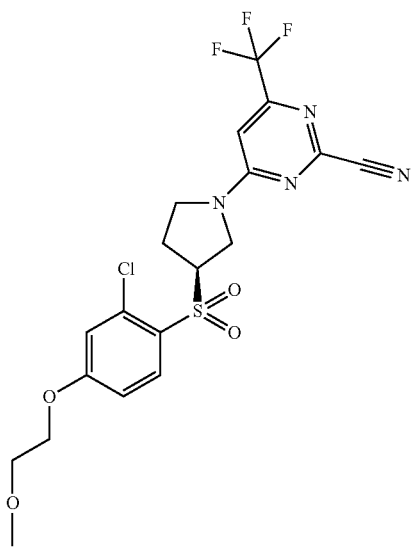 [SMILES: COCCOc1ccc(S(=O)(=O)[C@H]2CCN(c3cc(C(F)(F)F)nc(C#N)n3)C2)c(Cl)c1]

The title compound was prepared in analogy to the methods described for example 40C to yield light brown waxy solid (82 mg; 61%). MS: m/z=491.1 [M+H]+.

Example 52

4-[(S)-3-(2-Chloro-4-fluoro-benzenesulfonyl)-pyrrolidin-1-yl]-2-cyano-pyrimidine-5-carboxylic acid (2,2,2-trifluoro-ethyl)-amide

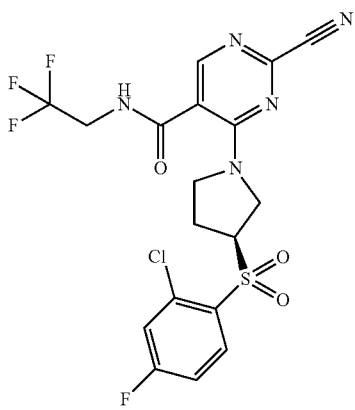 [SMILES: N#Cc1ncc(C(=O)NCC(F)(F)F)c(N2CC[C@H](S(=O)(=O)c3ccc(F)cc3Cl)C2)n1]

A) Synthesis of 2,4-dichloro-pyrimidine-5-carboxylic acid (2,2,2-trifluoro-ethyl)-amide

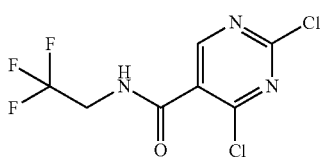 [SMILES: O=C(NCC(F)(F)F)c1cnc(Cl)nc1Cl]

2,4-Dichloropyrimidine-5-carbonyl chloride (1 g, 5 mmol) was dissolved in $CH_2Cl_2$ (20 mL), 2,2,2-trifluoroethylamine (515 mg, 5 mmol) and triethylamine (1.31 mL, 9 mmol) were added. The reaction mixture was stirred at 25° C. for 2 h. The reaction mixture was purified by flash chromatography to yield a white solid (780 mg, 60%). MS: m/z=271.9 [M–H]−.

B) (R)-3-(3-Nitro-benzenesulfonyloxy)-pyrrolidine-1-carboxylic acid tert-butyl ester

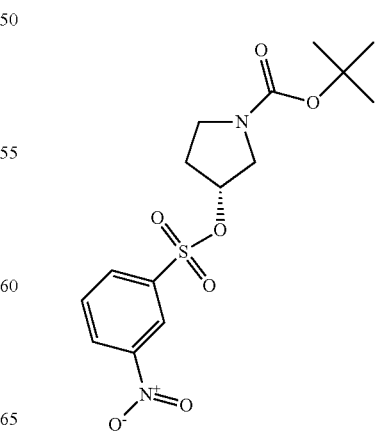

(R)-(−)-N-Boc-3-pyrrolidinol (25 g, 134 mmol) was dissolved in CH$_2$Cl$_2$ (250 mL) and Nos-Cl (31.36 g, 142 mmol) was added. The solution was cooled down to 0° C. and TEA (55.5 mL, 401 mmol) was slowly and carefully added through a dropping funnel. The icebath was removed and the reaction mixture was stirred at 25° C. for 18 h. The reaction mixture was extracted with aqueous 10% Na$_2$CO$_3$ solution and 0.1 N aqueous HCl solution. The organic layers were dried over Na$_2$SO$_4$, filtered and evaporated to dryness to yield a dark brown oil (39.8 g, 80%). MS: m/z=373.1 [M+H]$^+$.

C) (S)-3-(2-Chloro-4-fluoro-phenylsulfanyl)-pyrrolidine-1-carboxylic acid tert-butyl ester

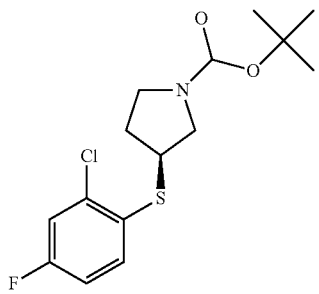 [SMILES: CC(C)(C)OC(O)N1CC[C@H](Sc2ccc(F)cc2Cl)C1]

Example 52B) (39.8 g, 107 mmol) was dissolved in propionitrile (500 mL), 2-chloro-4-fluorothiophenol (26.07 g, 160 mmol) was added. After that, TEA (29.6 mL) was carefully added. The reaction mixture was stirred at reflux over night. The reaction mixture was diluted with AcOEt and extracted with aqueous 10% Na$_2$CO$_3$ and aqueous 0.1 N HCl solutions. The organic layers were dried over Na$_2$SO$_4$, filtrated and evaporated. The reaction mixture was purified by flash chromatography to yield a light yellow oil (31.8 g, 90%). MS: m/z=276.0 [M+H-tBu]$^+$.

D) (S)-3-(2-Chloro-4-fluoro-benzenesulfonyl)-pyrrolidine-1-carboxylic acid tert-butyl ester

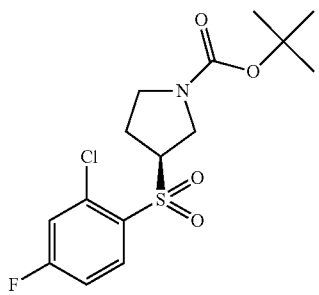 [SMILES: CC(C)(C)OC(=O)N1CC[C@H](S(=O)(=O)c2ccc(F)cc2Cl)C1]

Example 52C) (31.8 g, 96 mmol) was dissolved in CH$_2$Cl$_2$ (200 mL) at 25° C. and MCPBA (24.8 g, 201 mmol) was carefully added portion wise. The reaction mixture was stirred at 25° C. over night. The reaction mixture was extracted with aqueous 10% Na$_2$CO$_3$ and aqueous 0.1 N HCl solutions and a saturated aqueous solution of Na$_2$S$_2$O$_3$. The organic layers were dried over Na$_2$SO$_4$ and Na$_2$SO$_3$ for 2 h, filtrated and evaporated to yield a colorless oil (34.3 g, 98%). MS: m/z=308.4 [M+H-tBu]$^+$.

E) (S)-3-(2-Chloro-4-fluoro-benzenesulfonyl)-pyrrolidine

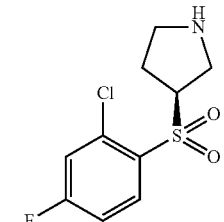

Example 52D) (6.0 g, 16 mmol) was dissolved in formic acid (160 mL) and stirred at 25° C. for 4 h. The reaction mixture was adjusted carefully with cold aqueous 10% Na$_2$CO$_3$-solution (1600 mL) to pH=8 and extracted with CH$_2$Cl$_2$. The water layer was washed three times with CH$_2$Cl$_2$, the combined organic layers were dried over Na$_2$SO$_4$, filtered and evaporated to yield a light brown waxy solid (4.26 g, 98%). MS: m/z=264.1 [M+H]$^+$.

F) 2-Chloro-4-[(S)-3-(2-chloro-4-fluoro-benzenesulfonyl)-pyrrolidin-1-yl]-pyrimidine-5-carboxylic acid (2,2,2-trifluoro-ethyl)-amide

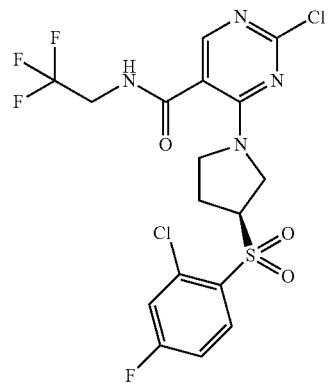 [SMILES: O=C(NCC(F)(F)F)c1cnc(Cl)nc1N1CC[C@H](S(=O)(=O)c2ccc(F)cc2Cl)C1]

Example 52A) (200 mg; 2 mmol) was dissolved in ACN (20 mL), example 53E) (614 mg, 2 mmol) and DIEA (400 µL, 2 mmol) were added. The reaction mixture was stirred at 25° C. over night. The reaction mixture was purified by flash chromatography. MS: m/z=501.1 [M+H]⁺.

G) 4-[(S)-3-(2-Chloro-4-fluoro-benzenesulfonyl)-pyrrolidin-1-yl]-2-cyano-pyrimidine-5-carboxylic acid (2,2,2-trifluoro-ethyl)-amide

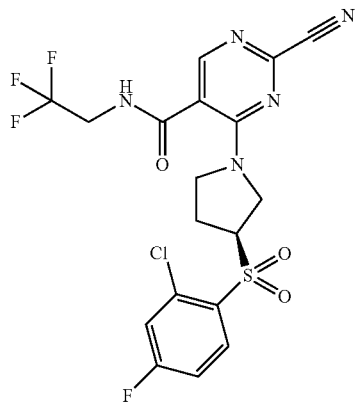 [SMILES: N#Cc1ncc(C(=O)NCC(F)(F)F)c(N2CC[C@H](S(=O)(=O)c3ccc(F)cc3Cl)C2)n1]

Example 52F) (180 mg) was dissolved in DMSO (1.7 mL), DABCO (81 mg) and KCN (47 mg) and water (0.3 mL) were added. The reaction mixture was stirred at 80° C. for 1 h. The mixture was purified by preparative HPLC to yield an orange solid (43 mg, 24%). MS: m/z=492.1 [M+H]⁺.

Example 53

4-{(S)-3-[4-(4-tert-Butyl-piperazin-1-yl)-2-chloro-benzenesulfonyl]-pyrrolidin-1-yl}-2-cyano-pyrimidine-5-carboxylic acid (2,2,2-trifluoro-ethyl)-amide

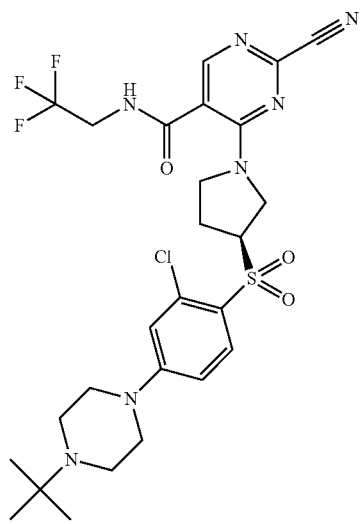 [SMILES: CC(C)(C)N1CCN(c2ccc(S(=O)(=O)[C@H]3CCN(c4nc(C#N)ncc4C(=O)NCC(F)(F)F)C3)c(Cl)c2)CC1]

Example 52G) (40 mg) was dissolved in ACN (2.0 mL), DIEA (0.03 mL, 2 eq) and N-tert.-butylpiperazine (23 mg, 2 eq) were added. The reaction mixture was stirred for 24 h at 25° C. The reaction mixture was purified by preparative HPLC to yield a brown solid (18 mg, 36%). MS: m/z=614.1 [M+H]⁺.

Example 54

4-{(S)-3-[2-Chloro-4-(2,2,2-trifluoro-ethoxy)-benzenesulfonyl]-pyrrolidin-1-yl}-2-cyano-pyrimidine-5-carboxylic acid (2,2,2-trifluoro-ethyl)-amide

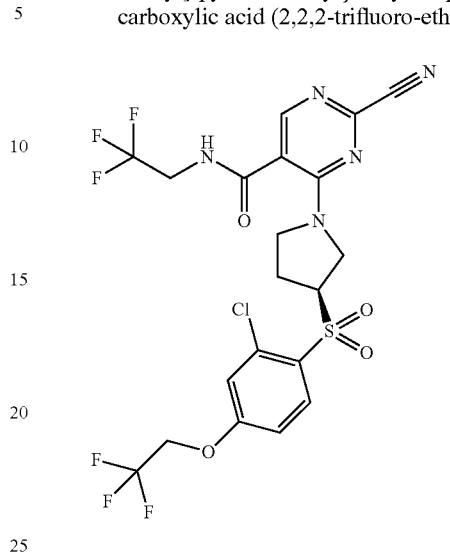

Example 52G) (43 mg) was dissolved in DMF (1 mL), Cs₂CO₃ (56 mg, 2 eq) and 2,2,2-trifluoroethanol (0.01 mL, 2 eq) were added. The reaction mixture was stirred for 24 h at 25° C. The reaction mixture was purified by preparative HPLC to yield an off-white solid (24 mg, 49%). MS: m/z=572.1 [M+H]⁺.

Example 55

4-{(S)-3-[2-Chloro-4-(4-cyclopropyl-piperazin-1-yl)-benzenesulfonyl]-pyrrolidin-1-yl}-2-cyano-pyrimidine-5-carboxylic acid (2,2,2-trifluoro-ethyl)-amide

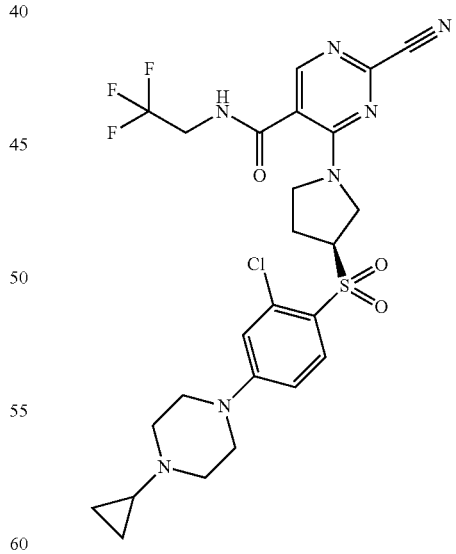

Example 52G) (43 mg) was dissolved in ACN (1.0 mL), DIEA (0.06 mL, 4 eq) and 1-cyclopropylpiperazine dihydrochloride (34 mg, 2 eq) were added. The reaction mixture was stirred for 24 h at 25° C. After that, additional DIEA (0.03 mL, 2 eq) and 1-cyclopropylpiperazine dihydrochloride (34 mg, 2 eq) were added. The reaction mixture was stirred for addi- A) 4-[(S)-3-(2-Chloro-4-fluoro-benzenesulfonyl)-pyrrolidin-1-yl]-2-cyano-pyrimidine-5-carboxylic acid [2-(4-chloro-phenyl)-propyl]-amide

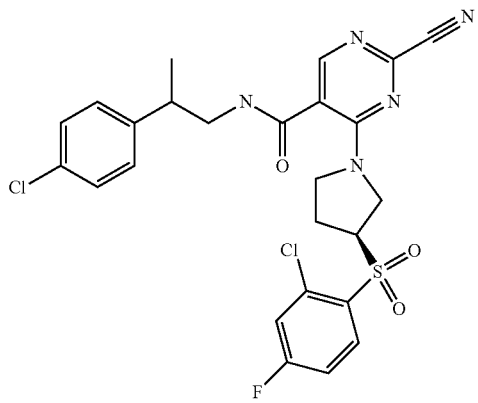

Example 57A) was prepared in analogy to methods described for example 52 to yield the title compound as a light yellow oil (100 mg, 25%). MS: m/z=562.1 [M+H]$^+$.

B) 4-{(S)-3-[4-(4-tert-Butyl-piperazin-1-yl)-2-chloro-benzenesulfonyl]-pyrrolidin-1-yl}-2-cyano-pyrimidine-5-carboxylic acid [2-(4-chloro-phenyl)-propyl]-amide

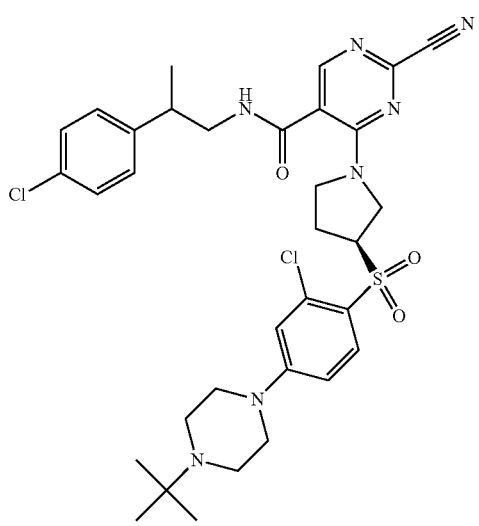

Example 57B) was prepared in analogy to methods described for example 52 to yield the title compound as a light yellow solid (25 mg, 44%). MS: m/z=686.3 [M+H]$^+$.

tional 24 h at 25° C. After that, additional DIEA (0.03 mL, 2 eq) and 1-cyclopropylpiperazine dihydrochloride (34 mg, 2 eq) were added. The reaction mixture was stirred for additional 48 h at 25° C. The reaction mixture was purified by preparative HPLC to yield a light yellow solid (18 mg, 35%). MS: m/z=598.2 [M+H]$^+$.

Example 56

4-[(S)-3-(2-Chloro-4-imidazol-1-yl-benzenesulfonyl)-pyrrolidin-1-yl]-2-cyano-pyrimidine-5-carboxylic acid (2,2,2-trifluoro-ethyl)-amide

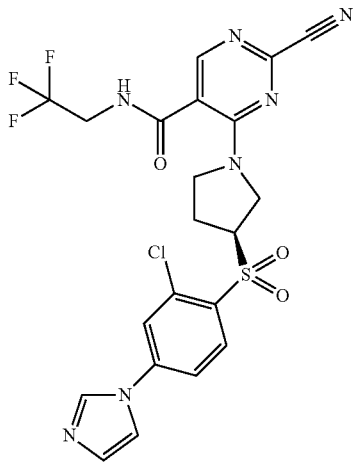 [SMILES: N#Cc1ncc(C(=O)NCC(F)(F)F)c(N2CC[C@H](S(=O)(=O)c3ccc(-n4ccnc4)cc3Cl)C2)n1]

Example 52G) (43 mg) was dissolved in ACN (1.0 mL), DIEA (0.03 mL, 2 eq) and imidazole (12 mg, 2 eq) were added. The reaction mixture was stirred for 24 h at 80° C. After that, additional imidazole (12 mg, 2 eq) was added. The reaction mixture was stirred for additional 24 h at 80° C. After that, additional imidazole (12 mg, 2 eq) was added. The reaction mixture was stirred for additional 48 h at 80° C. The reaction mixture was purified by preparative HPLC to yield a light yellow solid (16 mg, 34%). MS: m/z=540.3 [M+H]$^+$.

Example 57

4-{(S)-3-[4-(4-tert-Butyl-piperazin-1-yl)-2-chloro-benzenesulfonyl]pyrrolidin-1-yl}-2-cyano-pyrimidine-5-carboxylic acid [2-(4-chloro-phenyl)-propyl]-amide

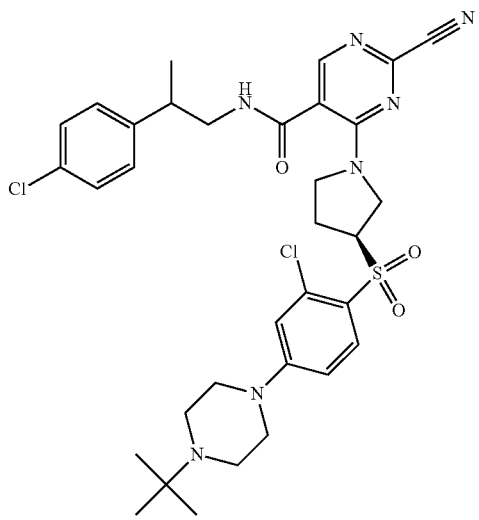 [SMILES: CC(CNC(=O)c1cnc(C#N)nc1N1CC[C@H](S(=O)(=O)c2ccc(N3CCN(C(C)(C)C)CC3)cc2Cl)C1)c1ccc(Cl)cc1]

Example 58

4-{(S)-3-[2-Chloro-4-(2,2,2-trifluoro-ethoxy)-benzenesulfonyl]-pyrrolidin-1-yl}-6-(2,2,2-trifluoro-ethyl)-6,7-dihydro-5H-pyrrolo[3,4-d]pyrimidine-2-carbonitrile

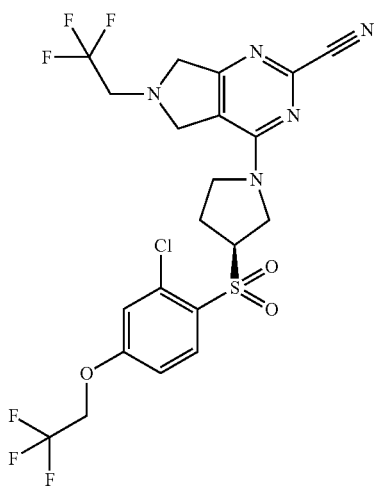 [SMILES: N#Cc1nc2c(c(N3CC[C@H](S(=O)(=O)c4ccc(OCC(F)(F)F)cc4Cl)C3)n1)CN(CC(F)(F)F)C2]

A) (S)-3-[2-Chloro-4-(2,2,2-trifluoro-ethoxy)-benzenesulfonyl]-pyrrolidine-1-carboxylic acid test-butyl ester

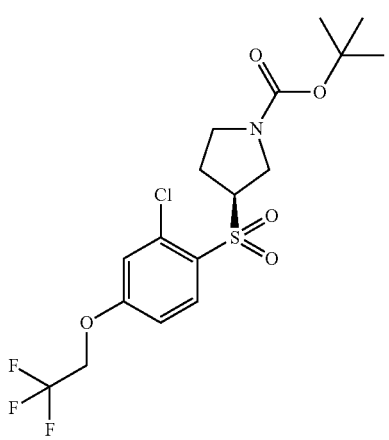 [SMILES: CC(C)(C)OC(=O)N1CC[C@H](S(=O)(=O)c2ccc(OCC(F)(F)F)cc2Cl)C1]

Example 52D) (1.2 g) was dissolved in DMF (20 mL), Cs₂CO₃ (2.15 g, 2 eq) and 2,2,2-trifluoroethanol (0.47 mL) were added. The reaction mixture was stirred for 48 h at 25° C. The reaction mixture was purified by flash chromatography to yield a colorless oil (1.28 g, 87%). MS: m/z=369.9 [M+H−OtBu]⁺.

B) (S)-3-[2-Chloro-4-(2,2,2-trifluoro-ethoxy)-benzenesulfonyl]-pyrrolidine

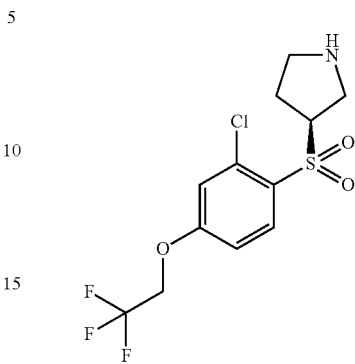

The title compound was prepared in analogy to example 52E) to yield a light brown oil (910 mg, 92%). MS: m/z=344.1 [M+H]⁺.

C) 2-Chloro-4-{(S)-3-[2-chloro-4-(2,2,2-trifluoro-ethoxy)-benzenesulfonyl]-pyrrolidin-1-yl}-5,7-dihydro-pyrrolo[3,4-d]pyrimidine-6-carboxylic acid tert-butyl ester

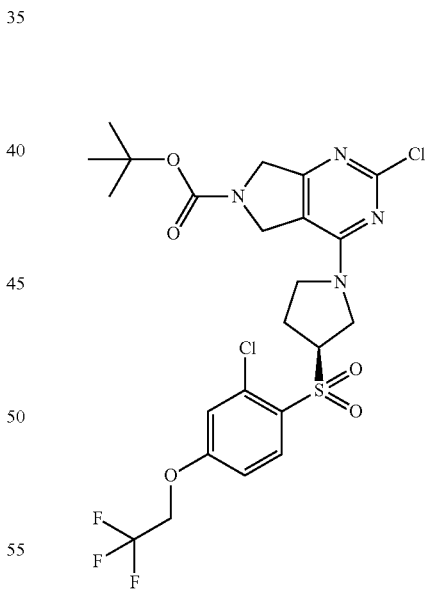

Tert.-butyl 2,4-dichloro-5H-pyrrolo[3,4-d]-pyrmidine6(7H)-carboxylate (500 mg) was dissolved in ACN (20 mL), DIEA (0.59 mL) and example 58B) (652 mg, 1.1 eq) were added. The reaction mixture was stirred for 3 h at 25° C. The reaction mixture was purified by flash chromatography to yield a white solid (510 mg, 50%). MS: m/z=597.3 [M+H]⁺.

D) 2-Chloro-4-{(S)-3-[2-chloro-4-(2,2,2-trifluoro-ethoxy)-benzenesulfonyl]-pyrrolidin-1-yl}-6,7-dihydro-5H-pyrrolo[3,4-d]pyrimidine

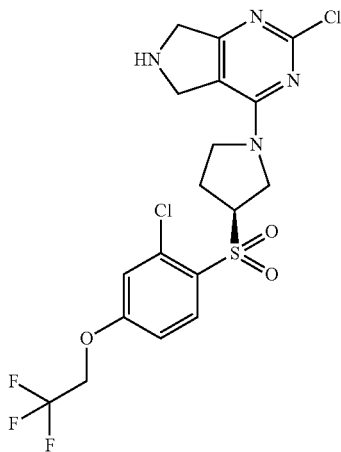 [SMILES: O=S(=O)(c1ccc(OCC(F)(F)F)cc1Cl)[C@H]1CCN(c2nc(Cl)nc3c2CNC3)C1]

Example 58C) (510 mg) was dissolved in CH$_2$Cl$_2$ (5 mL) and TFA (1.31 mL) was added. The reaction mixture was stirred 2 h at 25° C. The reaction mixture was extracted with saturated aqueous Na$_2$CO$_3$-solution and CH$_2$Cl$_2$. The combined organic layers were dried over Na$_2$SO$_4$, filtered and evaporated to yield a white solid (350 mg, 82%). MS: m/z=497.1 [M+H]$^+$.

E) 2-Chloro-4-{(S)-3-[2-chloro-4-(2,2,2-trifluoro-ethoxy)-benzenesulfonyl]-pyrrolidin-1-yl}-6-(2,2,2-trifluoro-ethyl)-6,7-dihydro-5H-pyrrolo[3,4-d]pyrimidine

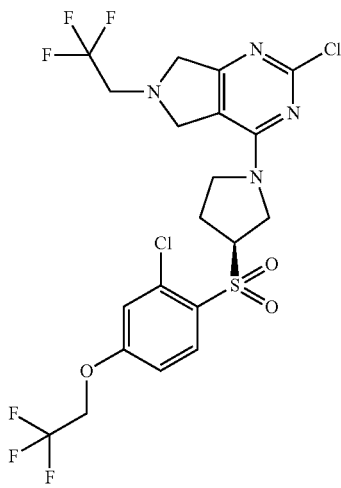 [SMILES: O=S(=O)(c1ccc(OCC(F)(F)F)cc1Cl)[C@H]1CCN(c2nc(Cl)nc3c2CN(CC(F)(F)F)C3)C1]

Example 58D) (175 mg) was dissolved in CH$_2$Cl$_2$ (3 mL), 2,2,2-trifluoroethyl trifluoromethanesulfonate (82 mg, 4 eq) and DIEA (0.12 mL) were added to the above suspension. The mixture was stirred at 25° C. for 24 h. After that, the reaction mixture was heated at 40° C. for 18 h. After that, additional 2,2,2-trifluoroethyl trifluoromethane-sulfonate (82, mg, 4 eq) and DIEA (0.12 mL) were added and the reaction mixture was heated at 40° C. for 24 h. After that, additional 2,2,2-trifluoroethyl trifluoromethane-sulfonate (164, mg, 8 eq) was added and the reaction mixture was heated at 40° C. for three days. The reaction mixture was purified by flash chromatography to yield a white foam (142 mg, 70%). MS: m/z=579.1 [M+H]$^+$.

F) 4-{(S)-3-[2-Chloro-4-(2,2,2-trifluoro-ethoxy)-benzenesulfonyl]-pyrrolidin-1-yl}-6-(2,2,2-trifluoro-ethyl)-6,7-dihydro-5H-pyrrolo[3,4-d]pyrimidine-2-carbonitrile

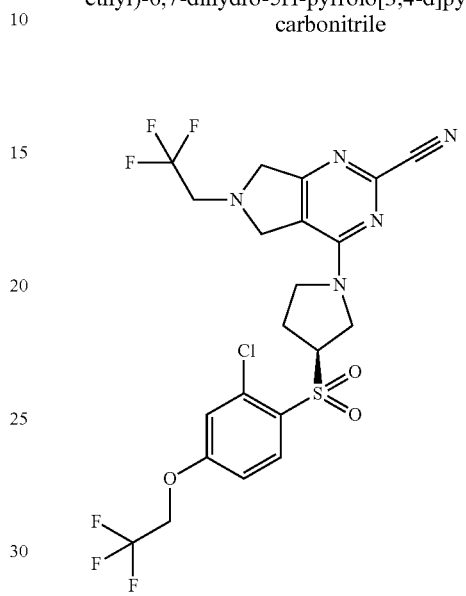

The title compound was synthesized according to the methods described for example 52G) to yield a light brown solid (56 mg, 40%). MS: m/z=570.3 [M+H]$^+$.

Example 59

4-[(S)-3-(2-Chloro-4-pyrazol-1-yl-benzenesulfonyl)-pyrrolidin-1-yl]-6-(2,2,2-trifluoro-ethyl)-6,7-dihydro-5H-pyrrolo[3,4-d]pyrimidine-2-carbonitrile

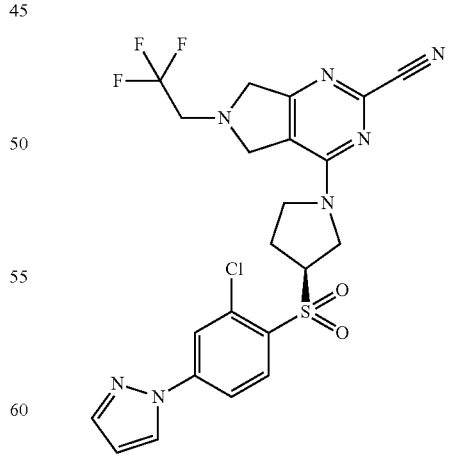

The title compound was prepared in analogy to the methods described for examples 58B)-F) to yield a brown foam (34 mg, 39%). MS: m/z=538.2 [M+H]$^+$. with the exception of step A):

91

A) (S)-3-(2-Chloro-4-pyrazol-1-yl-benzenesulfonyl)-pyrrolidine-1-carboxylic acid tert-butyl ester

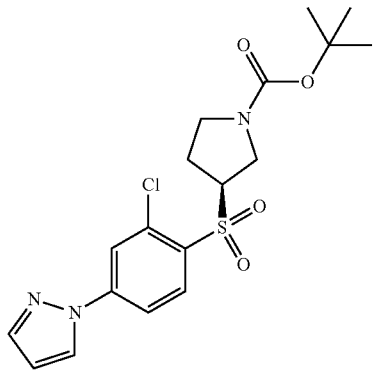 [SMILES: CC(C)(C)OC(=O)N1CC[C@H](S(=O)(=O)c2ccc(-n3cccn3)cc2Cl)C1]

Example 52D) (1 g) was dissolved in DMA (7.5 mL) at 25° C. Pyrazole (374 mg, 2 eq) and $Cs_2CO_3$ (1.8 g, 2 eq) were added. The reaction mixture was stirred in the microwave oven at 100° C. for 60 min. The reaction mixture was diluted with AcOEt (10 mL) and extracted with water. The organic layers were dried over $Na_2SO_4$, filtrated and evaporated to dryness. The reaction mixture was purified by flash chromatography to yield a white foam (610 mg, 54%). MS: m/z=356.1 $[M+H-tBu]^+$.

Example 60

4-[(S)-3-(2-Chloro-4-pyrazol-1-yl-benzenesulfonyl)-pyrrolidin-1-yl]-6-formyl-6,7-dihydro-5H-pyrrolo[3,4-d]pyrimidine-2-carbonitrile

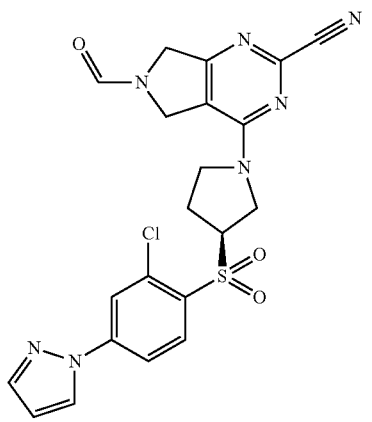 [SMILES: N#Cc1nc2c(c(N3CC[C@H](S(=O)(=O)c4ccc(-n5cccn5)cc4Cl)C3)n1)CN(C=O)C2]

The title compound was prepared in analogy to the methods described for examples 58B)-F) and 59A) to yield a brown foam (34 mg, 39%). MS: m/z=538.2 $[M+H]^+$. with the exception of step E):

92

E) 2-Chloro-4-[(S)-3-(2-chloro-4-pyrazol-1-yl-benzenesulfonyl)-pyrrolidin-1-yl]-5,7-dihydro-pyrrolo[3,4-d]pyrimidine-6-carbaldehyde

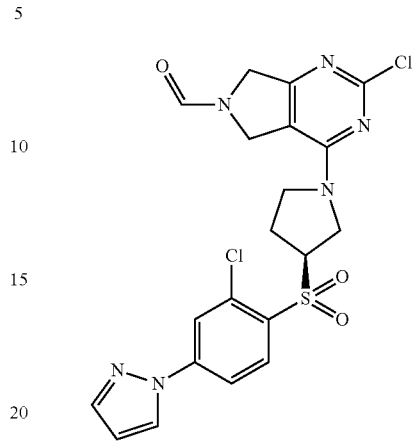

Methylcyclopropane-carboxylic acid (60 mg) was dissolved in $CH_2Cl_2$ (5 mL) and 3 drops of DMF. After that, oxalylchlorid (177 mg, 2.6 eq) was slowly added. The reaction mixture was stirred for 2 h at 25° C. The reaction mixture was evaporated and resolved in $CH_2Cl_2$ (2 mL) Now, example 60D) (215 mg) and TEA (109 mg, 2 eq) were added and stirred for 24 h at 25° C. The reaction mixture was purified with preparative HPLC to yield the title compound as sole by-product as a dark brown foam (62 mg, 21%). MS: m/z=520.1 $[M+H]^+$.

Example 61

6-[(S)-3-((S)-2-Chloro-4-hexahydro-pyrrolo[1,2-a]pyrazin-2-yl-benzenesulfonyl)-pyrrolidin-1-yl]pyridine-2-carbonitrile; compound with formic acid

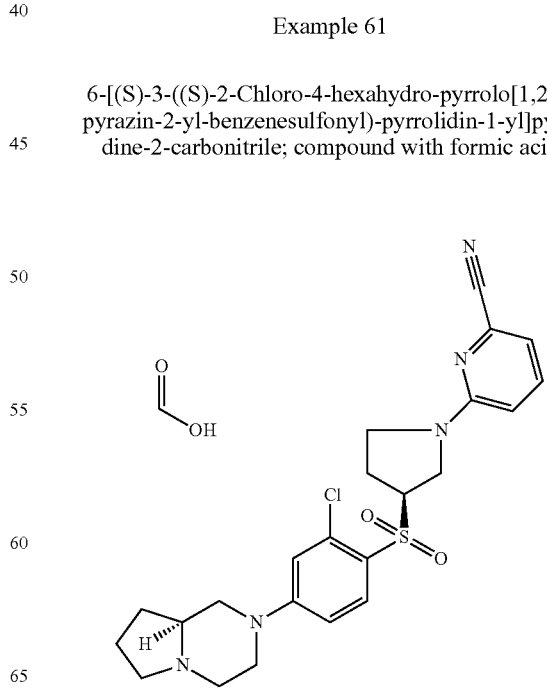

A) (S)-3-((S)-2-Chloro-4-hexahydro-pyrrolo[1,2-a]pyrazin-2-yl-benzenesulfonyl)-pyrrolidine-1-carboxylic acid tert-butyl ester

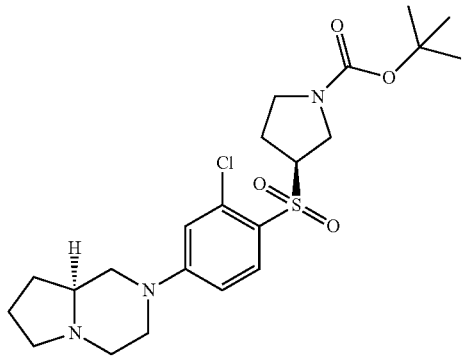 [SMILES: CC(C)(C)OC(=O)N1CC[C@H](S(=O)(=O)c2ccc(N3CCN4CCC[C@H]4C3)cc2Cl)C1]

In a 50 mL round-bottomed flask, (S)-tert-butyl 3-(2-chloro-4-fluorophenylsulfonyl)-pyrrolidine-1-carboxylate, example 52D) (2 g, 5.5 mmol, 1 eq) was combined with acetonitrile (20 mL) to give a light yellow solution. (S)-octahydropyrrolo[1,2-a]pyrazine (1.04 g, 8.25 mmol, 1.5 eq) and DIEA (1.42 g, 1.92 mL, 11.0 mmol, 2 eq) were added. The reaction mixture was stirred for 15 h. The reaction mixture was heated to 60° C. and stirred for 5 h. The crude reaction mixture was concentrated in vacuo. The reaction mixture was poured into EtOAc (25 mL) and extracted with aqueous 10% $Na_2CO_3$ (2×20 mL) and brine. The organic layers were dried over $Na_2SO_4$ and concentrated in vacuo to yield a colorless viscous oil (2.48 g, 96%).

B) (S)-2-[3-Chloro-4-((S)-pyrrolidine-3-sulfonyl)-phenyl]-octahydro-pyrrolo[1,2-a]pyrazine

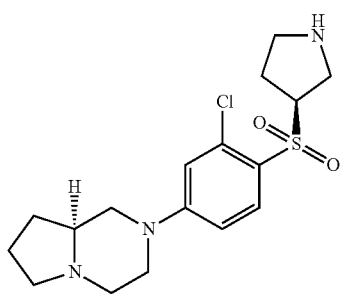 [SMILES: O=S(=O)(c1ccc(N2CCN3CCC[C@H]3C2)cc1Cl)[C@H]1CCNC1]

In a 100 mL round-bottomed flask, (S)-tert-butyl 3-(2-chloro-4-((S)-hexahydropyrrolo[1,2-a]pyrazin-2(1H)-yl)phenylsulfonyl)pyrrolidine-1-carboxylate, example 61A) (2.58 g, 5.49 mmol, 1.0 eq) was combined with dichloromethane (20 mL) to give a light brown solution. TFA (10.4 g, 7 mL, 90.9 mmol, 16.6 eq) was added. The reaction mixture was stirred for 16 h. The crude reaction mixture was concentrated in vacuo with toluene and used without further purification to yield a brown liquid containing toluene (35% purity, 5.7 g crude material, 98% yield).

C) 6-[(S)-3-((S)-2-Chloro-4-hexahydro-pyrrolo[1,2-a]pyrazin-2-yl-benzenesulfonyl)-pyrrolidin-1-yl]-pyridine-2-carbonitrile; compound with formic acid

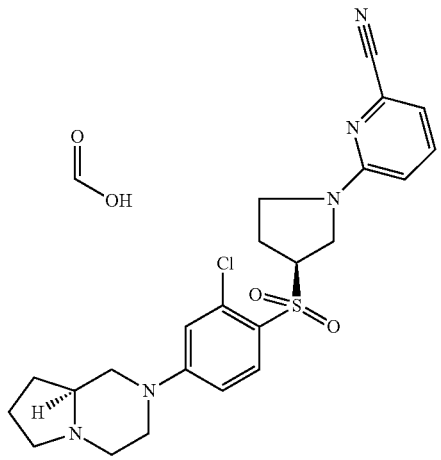

In a 5 mL MW-Tube, (S)-2-(3-chloro-4-((S)-pyrrolidin-3-ylsulfonyl)phenyl)-octahydropyrrolo[1,2-a]pyrazine, example 61B) (0.2 g, 189 μmol) was combined with acetonitrile (2 mL) to give a light brown solution. 6-Chloropicolinonitrile (34.1 mg, 246 μmol, 1.3 eq) and triethylamine (95.7 mg, 132 μL, 946 μmol, 5 eq) were added. The reaction mixture was heated to 160° C. and stirred for 30 min in the micro wave oven. The crude material was purified by preparative HPLC to yield a brown solid (42 mg, 43%).

MS: m/z=472.3 [M+H]⁺.

Example 62

6-[(S)-3-((S)-2-Chloro-4-hexahydro-pyrrolo[1,2-a]pyrazin-2-yl-benzenesulfonyl)-pyrrolidin-1-yl]-pyrazine-2-carbonitrile; compound with formic acid

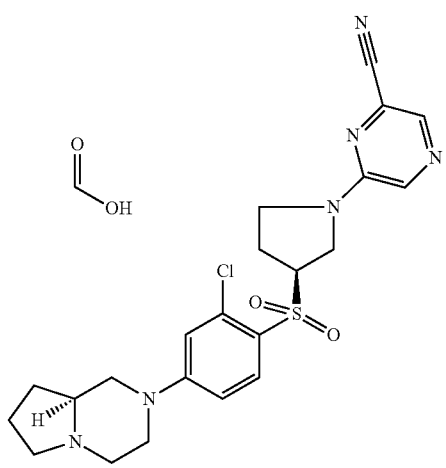

The title compound was prepared in analogy to the methods described for examples 61A-C) to yield a light brown solid (55 mg, 40%). MS: m/z=473.3 [M+H]⁺.

Example 63

2-[(S)-3-((S)-2-Chloro-4-hexahydro-pyrrolo[1,2-a]pyrazin-2-yl-benzenesulfonyl)-pyrrolidin-1-yl]-pyrimidine-4-carbonitrile; compound with formic acid

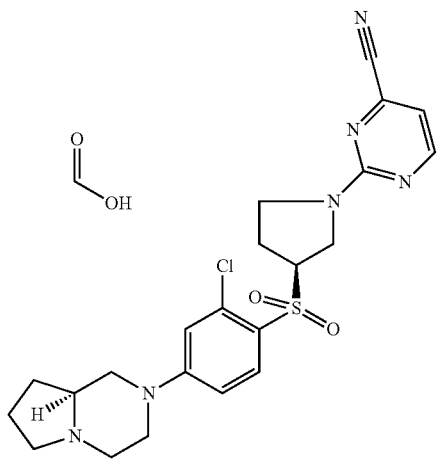

The title compound was prepared in analogy to the methods described for examples 61A-C) to yield a light brown solid (55 mg, 40%). MS: m/z=473.3 [M+H]$^+$.

Example 64

6-[3-((S)-2-Chloro-4-hexahydro-pyrrolo[1,2-a]pyrazin-2-yl-benzenesulfonyl)-pyrrolidin-1-yl]-3-nitro-pyridine-2-carbonitrileformic acid

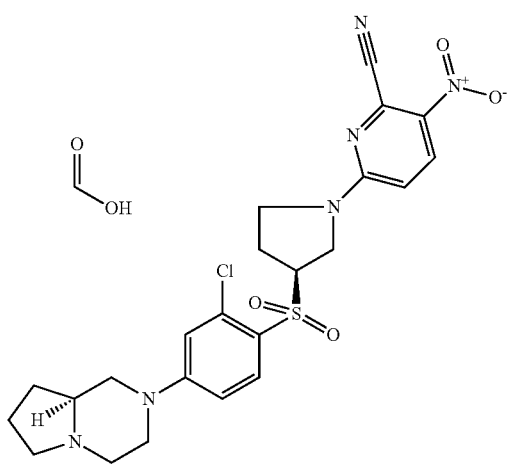

The title compound was prepared in analogy to the methods described for examples 61A-C) to yield a light brown solid (55 mg, 40%). MS: m/z=517.3 [M+H]$^+$.

Example 65

(S)-6-(3-(2-(Trifluoromethyl)phenylsulfonyl)pyrrolidin-1-yl)picolinonitrile

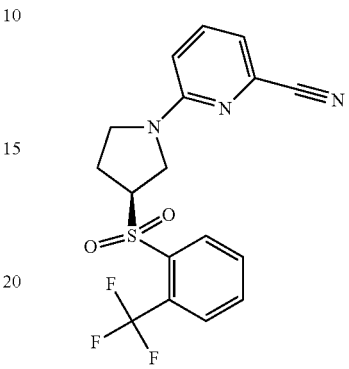

The title compound was prepared in analogy to the methods described for examples 61A-C) and example 12 to yield a yellow solid (88 mg, 32%). MS: m/z=382.0861 [M+H]$^+$.

Example 66

(S)-2-(3-(2-(Trifluoromethyl)phenylsulfonyl)pyrrolidin-1-yl)pyrimidine-4-carbonitrile

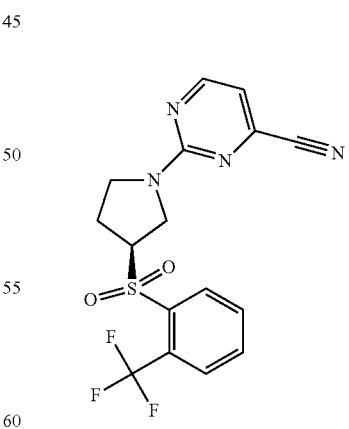

The title compound was prepared in analogy to the methods described for examples 61A-C) and example 12 to yield a yellow gum (220 mg, 80%). MS: m/z=383.0821 [M+H]$^+$.

Example 67

(S)-6-(3-(2-(Trifluoromethyl)phenylsulfonyl)pyrrolidin-1-yl)pyrazine-2-carbonitrile

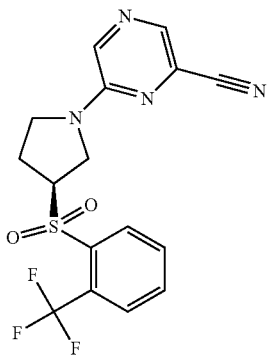 [SMILES: N#Cc1cncc(N2CC[C@H](S(=O)(=O)c3ccccc3C(F)(F)F)C2)n1]

The title compound was prepared in analogy to the methods described for examples 61A-C) and example 12 to yield a yellow gum (90 mg, 33%). MS: m/z=383.0813 [M+H]+.

Example 68

6-((S)-3-{2-Chloro-4-[4-(2-methoxy-ethyl)-piperazin-1-yl]-benzenesulfonyl}pyrrolidin-1-yl)-pyrazine-2-carbonitrile

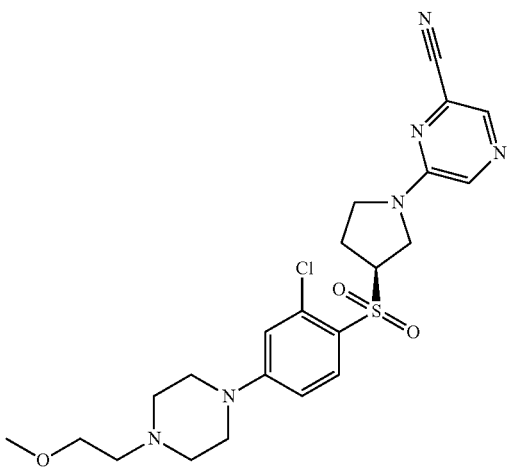 [SMILES: COCCN1CCN(c2ccc(S(=O)(=O)[C@H]3CCN(c4cncc(C#N)n4)C3)c(Cl)c2)CC1]

The title compound was prepared in analogy to the methods described for examples 61A-C) to yield a light brown gum (24 mg, 20%). MS: m/z=491.2 [M+H]+.

Example 69

2-((S)-3-{2-Chloro-4-[4-(2-methoxy-ethyl)-piperazin-1-yl]-benzenesulfonyl}-pyrrolidin-1-yl)-pyrimidine-4-carbonitrile

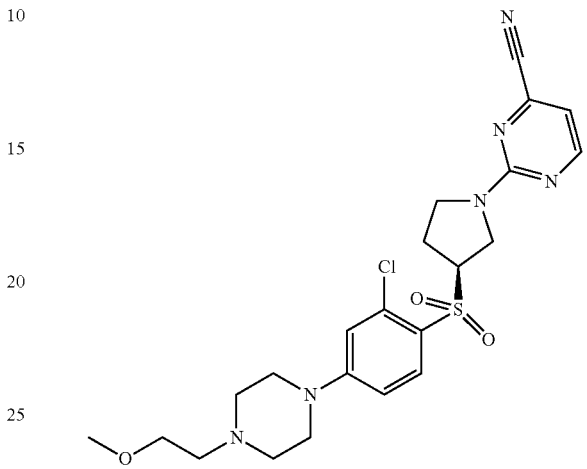

The title compound was prepared in analogy to the methods described for examples 61A-C) to yield a light brown gum (60 mg, 49%). MS: m/z=491.2 [M+H]+.

Example 70

6-((S)-3-{2-Chloro-4-[4-(2-methoxy-ethyl)-piperazin-1-yl]-benzenesulfonyl}-pyrrolidin-1-yl)-pyridine-2-carbonitrile

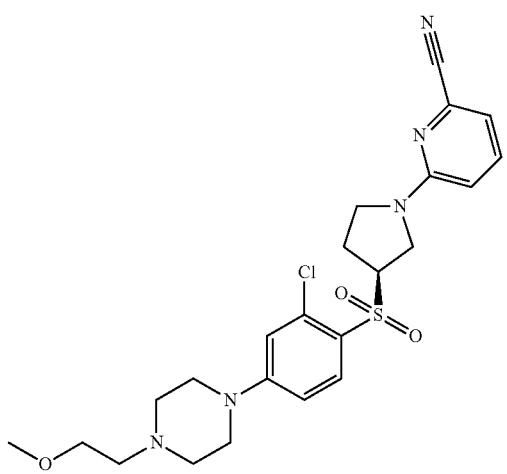 [SMILES: COCCN1CCN(c2ccc(S(=O)(=O)[C@H]3CCN(c4cccc(C#N)n4)C3)c(Cl)c2)CC1]

The title compound was prepared in analogy to the methods described for examples 61A-C) to yield a light brown gum (14 mg, 12%). MS: m/z=490.3 [M+H]+.

Example 71

6-((S)-3-{2-Chloro-4-[4-(2-methoxy-ethyl)-piperazin-1-yl]benzenesulfonyl}pyrrolidin-1-yl)-3-nitro-pyridine-2-carbonitrile

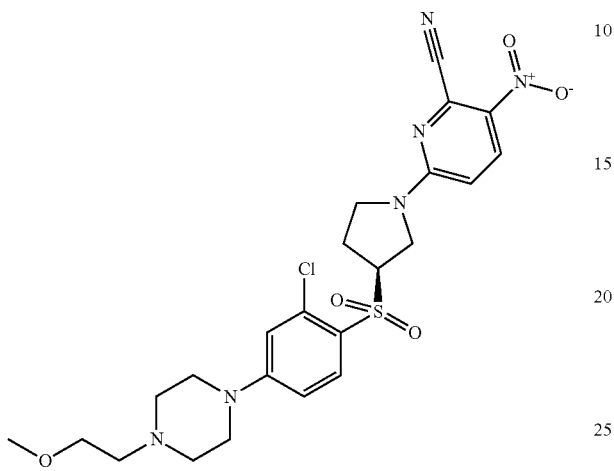

The title compound was prepared in analogy to the methods described for examples 61A-C) to yield a yellow solid (45 mg, 34%). MS: m/z=535.3 [M+H]$^+$.

Example 72

(S)-6-(3-(2-Chloro-4-fluorophenylsulfonyl)pyrrolidin-1-yl)picolinonitrile

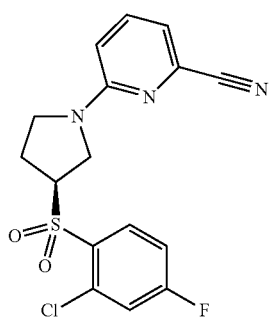 [SMILES: N#Cc1cccc(N2CC[C@H](S(=O)(=O)c3ccc(F)cc3Cl)C2)n1]

The title compound was prepared in analogy to the methods described for examples 61A-C) starting from intermediate 52E) to yield a light brown solid (4 mg, 1%). MS: m/z=366.0496 [M+H]$^+$.

Example 73

(S)-2-(3-(2-Chloro-4-fluorophenylsulfonyl)pyrrolidin-1-yl)pyrimidine-4-carbonitrile

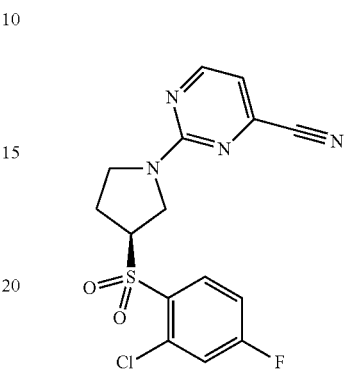

The title compound was prepared in analogy to the methods described for examples 61A-C) starting from intermediate 52E) to yield a yellow solid (60 mg, 14%). MS: m/z=367.0441 [M+H]$^+$.

Example 74

(S)-6-(3-(2-Chloro-4-fluorophenylsulfonyl)pyrrolidin-1-yl)pyrazine-2-carbonitrile

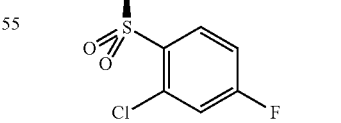

The title compound was prepared in analogy to the methods described for examples 61A-C) starting from intermediate 52E) to yield a brown oil (63 mg, 13%). MS: m/z=367.0413 [M+H]$^+$.

Example 75

(S)-2-(3-(2-Chloro-4-(4-methylpiperazin-1-yl)phenylsulfonyl)pyrrolidin-1-yl)pyrimidine-4-carbonitrile

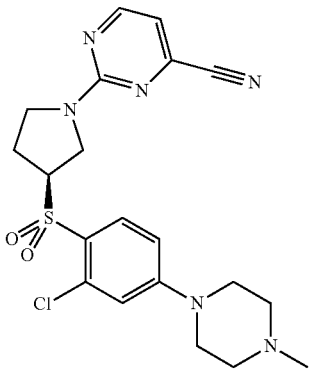 [SMILES: CN1CCN(c2ccc(S(=O)(=O)[C@H]3CCN(c4nccc(C#N)n4)C3)c(Cl)c2)CC1]

In a 10 mL round-bottomed flask, (S)-2-(3-(2-chloro-4-fluorophenylsulfonyl)pyrrolidin-1-yl)pyrimidine-4-carbonitrile (example 73) (50 mg, 136 µmol, 1 eq) was combined with acetonitrile (4 mL) to give a light yellow solution. 1-Methylpiperazine (20.7 mg, 22.9 µl, 204 µmol, 1.5 eq) and DIEA (35.2 mg, 47.6 µl, 273 µmol, 2 eq) were added. The reaction mixture was heated to 60° C. and stirred for 20 h. After that, 1-methylpiperazine (0.7 eq) and of DIEA (1 eq) were added. The reaction mixture was stirred at 60° C. for 5 h. After that, additional 1-methylpiperazine (1 eq) and DIEA (1.2 eq) were added. The reaction mixture was stirred at 60° C. for 16 h. The crude reaction mixture was concentrated in vacuo. The reaction mixture was poured into aqueous 5% $Na_2CO_3$ solution and extracted with EtOAc (3×10 mL). The organic layers were combined and washed with saturated aqueous NaCl solution (1×). The organic layers were dried over $Na_2SO_4$ and concentrated in vacuo. The crude material was purified by flash chromatography (silica gel, 10 g, $CH_2Cl_2$/MeOH 98/2) to yield a light yellow foam (42 mg, 69%). MS: m/z=447.1409 [M+H]$^+$.

Example 76

(S)-6-(3-(2-Chloro-4-(4-methylpiperazin-1-yl)phenylsulfonyl)pyrrolidin-1-yl)pyrazine-2-carbonitrile

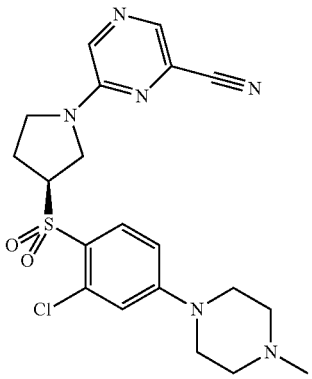 [SMILES: CN1CCN(c2ccc(S(=O)(=O)[C@H]3CCN(c4cncc(C#N)n4)C3)c(Cl)c2)CC1]

The title compound was prepared in analogy to the methods described for example 75 to yield a light yellow foam (40 mg, 56%). MS: m/z=447.1412 [M+H]$^+$.

Example 77

2-Cyano-4-[(S)-3-(2-trifluoromethyl-benzenesulfonyl)-pyrrolidin-1-yl]pyrimidine-5-carboxylic acid (2-phenyl-cyclopropyl)-amide

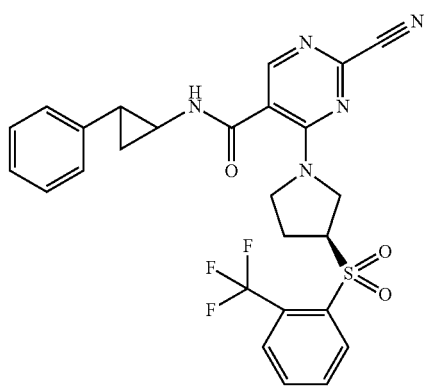 [SMILES: N#Cc1ncc(C(=O)NC2CC2c2ccccc2)c(N2CC[C@H](S(=O)(=O)c3ccccc3C(F)(F)F)C2)n1]

The title compound was prepared in analogy to the methods described for examples 52 and example 12 to yield a light yellow foam (536 mg, 70%) as a mixture of diastereomers [1:1]. MS: m/z=542.4 [M+H]$^+$.

Example 78

2-Cyano-4-[(S)-3-(2-trifluoromethyl-benzenesulfonyl)-pyrrolidin-1-yl]pyrimidine-5-carboxylic acid [2-(4-chloro-phenyl)-propyl]-amide

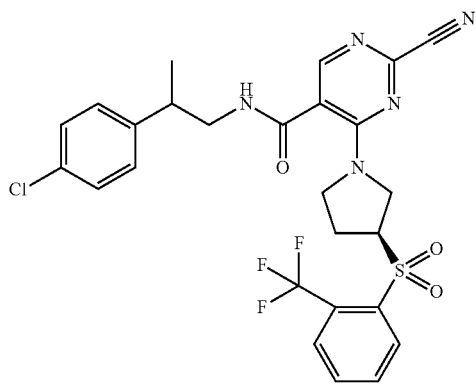 [SMILES: CC(CNC(=O)c1cnc(C#N)nc1N1CC[C@H](S(=O)(=O)c2ccccc2C(F)(F)F)C1)c1ccc(Cl)cc1]

The title compound was prepared in analogy to the methods described for examples 52 and example 12 to yield a white foam (315 mg, 57%) as a mixture of diastereomers [1:1]. MS: m/z=578.2 [M+H]$^+$.

Example 79

2-Cyano-4-[(S)-3-(2-trifluoromethyl-benzenesulfonyl)-pyrrolidin-1-yl]pyrimidine-5-carboxylic acid 4-trifluoromethyl-benzylamide

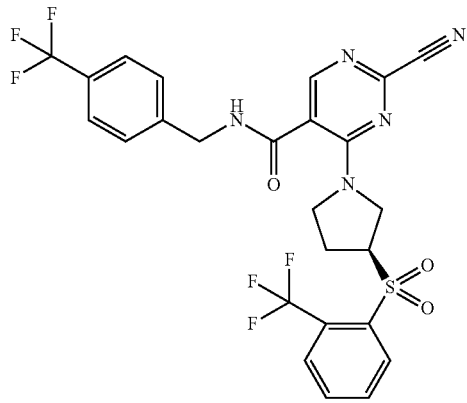 [SMILES: N#Cc1ncc(C(=O)NCc2ccc(C(F)(F)F)cc2)c(N2CC[C@H](S(=O)(=O)c3ccccc3C(F)(F)F)C2)n1]

The title compound was prepared in analogy to the methods described for examples 52 and example 12 to yield a white solid (13 mg, 38%). MS: m/z=584.2 [M+H]$^+$.

Example 80

2-Cyano-4-[(S)-3-(2,3-dichloro-benzenesulfonyl)-pyrrolidin-1-yl]pyrimidine-5-carboxylic acid 4-trifluoromethyl-benzylamide

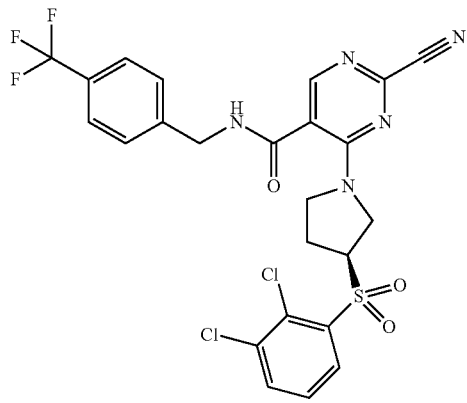 [SMILES: N#Cc1ncc(C(=O)NCc2ccc(C(F)(F)F)cc2)c(N2CC[C@H](S(=O)(=O)c3cccc(Cl)c3Cl)C2)n1]

The title compound was prepared in analogy to the methods described for examples 52 and example 12 to yield a white solid (15 mg, 29%). MS: m/z=584.2 [M+H]$^+$.

Example 81

2-Cyano-4-[(S)-3-(2-trifluoromethyl-benzenesulfonyl)-pyrrolidin-1-yl]pyrimidine-5-carboxylic acid [1-(4-fluoro-phenyl)-cyclopropyl]-amide

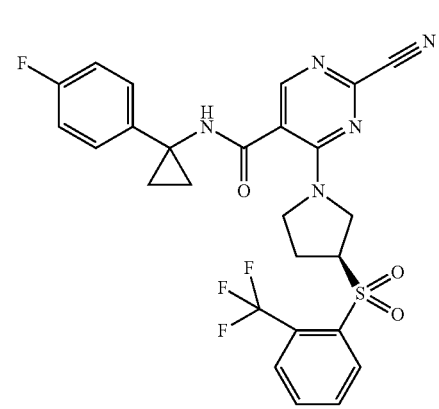 [SMILES: N#Cc1ncc(C(=O)NC2(c3ccc(F)cc3)CC2)c(N2CC[C@H](S(=O)(=O)c3ccccc3C(F)(F)F)C2)n1]

The title compound was prepared in analogy to the methods described for examples 52 and example 12 to yield a white solid (18 mg, 44%). MS: m/z=560.2 [M+H]$^+$.

Example 82

2-Cyano-4-[(S)-3-(2,3-dichloro-benzenesulfonyl)-pyrrolidin-1-yl]pyrimidine-5-carboxylic acid [1-(4-fluoro-phenyl)-cyclopropyl]-amide

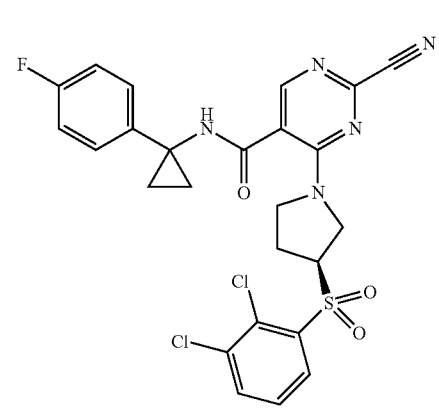 [SMILES: N#Cc1ncc(C(=O)NC2(c3ccc(F)cc3)CC2)c(N2CC[C@H](S(=O)(=O)c3cccc(Cl)c3Cl)C2)n1]

The title compound was prepared in analogy to the methods described for examples 52 and example 12 to yield a white solid (16 mg, 24%). MS: m/z=560.1 [M+H]$^+$.

Example 83

2-Cyano-4-[(S)-3-(2-trifluoromethyl-benzenesulfonyl)-pyrrolidin-1-yl]pyrimidine-5-carboxylic acid (2,2,2-trifluoro-ethyl)-amide

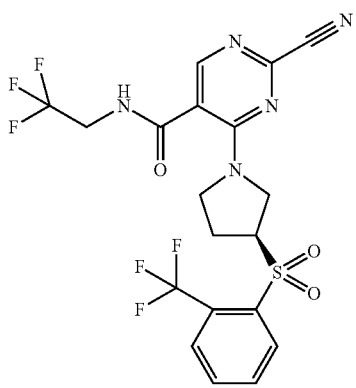 [SMILES: N#Cc1ncc(C(=O)NCC(F)(F)F)c(N2CC[C@H](S(=O)(=O)c3ccccc3C(F)(F)F)C2)n1]

The title compound was prepared in analogy to the methods described for examples 52 and example 12 to yield a white solid (10 mg, 42%). MS: m/z=508.1 [M+H]$^+$.

Example 84

2-Cyano-4-[(S)-3-(2,3-dichloro-benzenesulfonyl)-pyrrolidin-1-yl]pyrimidine-5-carboxylic acid (2,2,2-trifluoro-ethyl)-amide

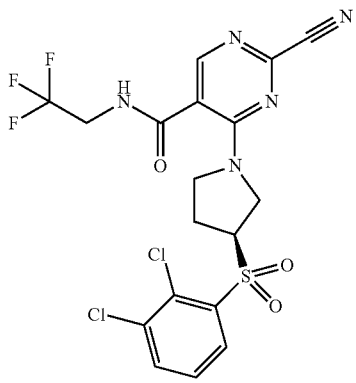 [SMILES: N#Cc1ncc(C(=O)NCC(F)(F)F)c(N2CC[C@H](S(=O)(=O)c3cccc(Cl)c3Cl)C2)n1]

The title compound was prepared in analogy to the methods described for examples 52 and example 12 to yield a white solid (16 mg, 25%). MS: m/z=508.0 [M+H]$^+$.

Example 85

2-Cyano-4-[(S)-3-(2-trifluoromethyl-benzenesulfonyl)-pyrrolidin-1-yl]pyrimidine-5-carboxylic acid [2-(4-chloro-phenyl)-propyl]-amide (Entity A)

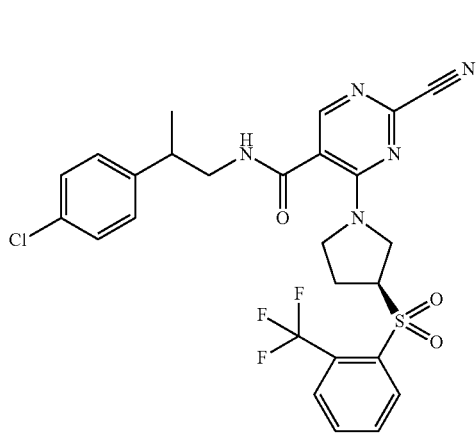 [SMILES: CC(CNC(=O)c1cnc(C#N)nc1N1CC[C@H](S(=O)(=O)c2ccccc2C(F)(F)F)C1)c1ccc(Cl)cc1]

The title compound was obtained as a pure enantiomer after purification of example 78 by chiral HPLC to yield a light brown solid (132 mg, 60%). MS: m/z=578.2 [M+H]$^+$.

Example 86

2-Cyano-4-[(S)-3-(2-trifluoromethyl-benzenesulfonyl)-pyrrolidin-1-yl]pyrimidine-5-carboxylic acid [2-(4-chloro-phenyl)-propyl]-amide (Entity B)

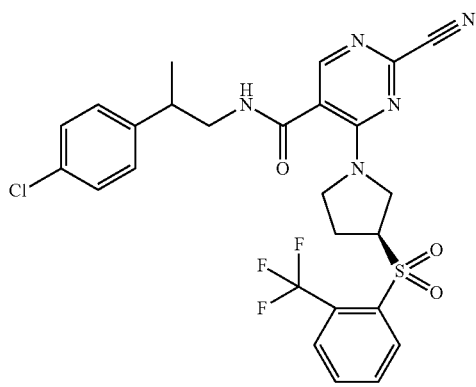 [SMILES: CC(CNC(=O)c1cnc(C#N)nc1N1CC[C@H](S(=O)(=O)c2ccccc2C(F)(F)F)C1)c1ccc(Cl)cc1]

The title compound was obtained as a pure enantiomer after purification of example 78 by chiral HPLC to yield a light brown solid (32 mg, 15%). MS: m/z=578.2 [M+H]$^+$.

Example 87

2-Cyano-4-[(S)-3-(2-trifluoromethyl-benzenesulfonyl)-pyrrolidin-1-yl]pyrimidine-5-carboxylic acid [1-(4-chloro-phenyl)-cyclopropylmethyl]-amide

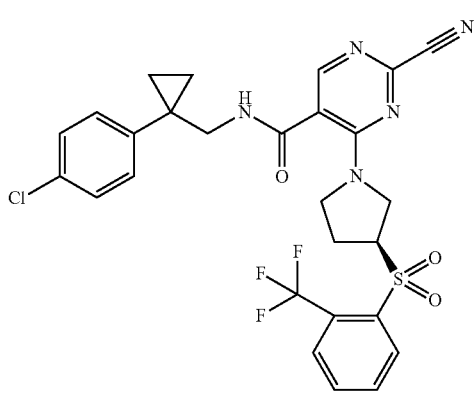 [SMILES: N#Cc1ncc(C(=O)NCC2(c3ccc(Cl)cc3)CC2)c(N2CC[C@H](S(=O)(=O)c3ccccc3C(F)(F)F)C2)n1]

The title compound was prepared in analogy to the methods described for examples 52 and example 12 to yield a white solid (239 mg, 66%). MS: m/z=590.3 [M+H]$^+$.

Example 88

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L.

Substrate (20 µM): Z-Val-Val-Arg-AMC, except for Cat K which uses Z-Leu-Arg-AMC (both from Bachem).

Z=Benzyloxycarbonyl.
AMC=7-Amino-4-Methyl-Coumarin.
DTT=dithiothreitol.
Final volume: 100 µL.
Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. IC$_{50}$ are calculated by standard methods.

Inhibition of human Cat S, mouse Cat S, human Cat K, mouse Cat K, human Cat B, mouse Cat B, human Cat L and mouse Cat L have been measured separately. The results obtained for human Cat S for representative compounds of the invention are expressed in the following table.

| Example | IC$_{50}$ [uM] |
| --- | --- |
| 1 | 0.415 |
| 2 | 0.051 |
| 3 | 0.315 |
| 4 | 0.136667 |
| 5 | 0.246667 |
| 6 | 0.0645 |
| 7 | 0.0875 |
| 8 | 0.0675 |
| 9 | 0.063 |
| 10 | 0.11 |
| 11 | 0.087 |
| 12 | 0.0015 |
| 13 | 0.0078 |
| 14 | 0.00031 |
| 15 | 0.0032 |
| 16 | 0.000245 |
| 17 | 0.0175 |
| 18 | 0.00065 |
| 19 | 1.96938 |
| 20 | 0.004 |
| 21 | 0.036 |
| 22 | 0.0036 |
| 23 | 0.00535 |
| 24 | 0.00063 |
| 25 | 0.0056 |
| 26 | 0.000935 |
| 27 | 0.00165 |
| 28 | 0.000665 |
| 29 | 0.00073 |
| 30 | 0.0015 |
| 31 | 0.0018 |
| 32 | 0.001433 |
| 33 | 0.008733 |
| 34 | 0.007 |
| 35 | 0.0023 |
| 36 | 0.000883 |
| 37 | 0.004967 |
| 38 | 0.000205 |
| 39 | 0.00055 |
| 40 | 0.000167 |
| 41 | 0.00052 |
| 42 | 0.000335 |
| 43 | 0.000415 |
| 44 | 0.00015 |
| 45 | 0.000355 |
| 46 | 0.0017 |
| 47 | 0.000052 |
| 48 | 0.00056 |
| 49 | 0.000535 |
| 50 | 0.00011 |
| 51 | 0.00013 |
| 52 | 0.00315 |
| 53 | 0.00235 |
| 54 | 0.004 |
| 55 | 0.00355 |
| 56 | 0.0012 |
| 57 | 0.0027 |
| 58 | 0.0017 |
| 59 | 0.000945 |
| 60 | 0.00275 |
| 61 | 0.014495 |
| 62 | 0.009114 |
| 63 | 0.002121 |
| 64 | — |
| 65 | 0.015695 |
| 66 | 0.002202 |
| 67 | 0.010615 |
| 68 | 0.035625 |
| 69 | 0.005068 |
| 70 | 0.039665 |
| 71 | 6.857 |
| 72 | 0.48745 |
| 73 | 0.01985 |
| 74 | 0.1215 |
| 75 | 0.004372 |
| 76 | 0.019948 |
| 77 | 0.00066 |
| 78 | 0.000056 |
| 79 | 0.000029 |
| 80 | 0.000155 |
| 81 | 0.00063 |
| 82 | 0.0005 |
| 83 | 0.000061 |
| 84 | 0.00032 |

-continued

| Example | IC$_{50}$ [uM] |
|---|---|
| 85 | 0.000365 |
| 86 | 0.031 |
| 87 | 0.000305 |

In the foregoing assay, the compounds according to the invention have an IC$_{50}$ which is between 0.00001 and 100 μM, preferably between 0.00001 and 50 μM, more preferably between 0.00001 and 20 μM.

Example A

A compound of formula (I) can be used in a manner known per se as the active ingredient for the production of tablets of the following composition:
Per Tablet

| Active ingredient | 200 mg |
|---|---|
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:
Per Capsule

| Active ingredient | 100.0 mg |
|---|---|
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of formula (I)

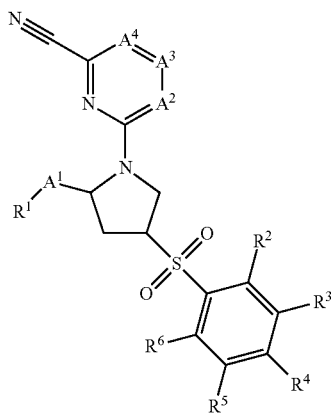

wherein
R$^1$ is selected from the group consisting of hydrogen, alkyl, morpholinyl, haloalkylamino, alkyloxadiazolyl, hydroxyl, halopyrrolidinyl, azetidinyl, alkylamino, amino, cyanoalkylamino, halophenylalkylamino and cyanocycloalkylamino;
R$^2$, R$^3$, R$^4$, R$^5$ and R$^6$ are each independently selected from the group consisting of hydrogen, alkyl, haloalkyl, hydroxyalkyl, alkoxy, haloalkyloxy, halogen, hydroxyl, cyanopyrazinyloxy, pyrazolyl, alkylpyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, haloalkylpiperidinyl, piperidinylalkoxy, oxetanyloxy, alkylpyrazolyl, halopyridinyl, alkylpyridinyl, cycloalkyl, cycloalkylalkyl, halophenyl, alkylcarbonylaminocycloalkylalkyl, haloalkylpiperazinyl, alkylamino, alkoxyalkylpiperazinyl, cycloalkylpiperazinyl, hexahydropyrrolo[1,2-a]pyrazinyl, 5,6-dihydro-8H-[1,2,4]triazolo[4,3-a]pyrazin-7-yl, alkylimidazolyl, azetidinyl, cycloalkylpiperazinyl, alkylimidazolyl, alkoxyalkoxy, imidazo[4,5-c]pyridinyl, alkylpiperazinyl, hexahydro-pyrrolo[1,2-a]pyrazinyl, haloazetidinyl, pyrimindinyl and alkenyloxy;
A$^1$ is —CH$_2$—, carbonyl, —C(O)O— or absent;
A$^2$ is nitrogen or CR$^7$;
A$^3$ is nitrogen or CR$^8$;
A$^4$ is nitrogen or CR$^9$;
R$^7$ is selected from the group consisting of hydrogen, alkyl, haloalkyl, halogen, hydroxyl, haloalkylaminocarbonyl; halophenylalkylaminocarbonyl, phenylcycloalkylaminocarbonyl, haloalkylphenylalkylaminocarbonyl, halophenylcycloalkylaminocarbonyl and halophenylcycloalkylalkylaminocarbonyl;
R$^8$ is selected from the group consisting of hydrogen, alkyl, haloalkyl, halogen and hydroxyl;
or R$^7$ and R$^8$ together with the carbon atom to which they are attached form cycloalkyl or substituted pyrrolidine, wherein substituted pyrrolidine is pyrrolidine N-substituted with haloalkyl or formyl;
R$^9$ is selected from the group consisting of hydrogen, alkyl, haloalkyl, halogen and nitro;
or R$^8$ and R$^9$ together with the carbon atom to which they are attached form cycloalkyl;
or a pharmaceutically acceptable salt thereof.
2. A compound according to claim 1, wherein
R$^7$ is selected from the group consisting of hydrogen, alkyl, haloalkyl, halogen and hydroxyl;
R$^8$ is selected from the group consisting of hydrogen, alkyl, haloalkyl, halogen and hydroxyl;
or R$^7$ and R$^8$ together with the carbon atom to which they are attached form cycloalkyl;
R$^9$ is selected from the group consisting of hydrogen, alkyl, haloalkyl and halogen;
or R$^8$ and R$^9$ together with the carbon atom to which they are attached form cycloalkyl.
3. A compound according to claim 1, wherein R$^1$ is hydrogen or amino.
4. A compound according to claim 1, wherein R$^2$, R$^3$, R$^4$, R$^5$ and R$^6$ are each independently selected from the group consisting of hydrogen, halogen, hydroxyl, haloalkyl, cyanopyrazinyloxy, alkylpiperazinyl, hexahydro-pyrrolo[1,2-a]pyrazinyl, haloalkyloxy, pyrazolyl, cycloalkylpiperazinyl, imidazolyl and alkoxyalkoxy.

5. A compound according to claim 1, wherein $R^2$ and $R^6$ are independently selected from the group consisting of hydrogen, halogen and haloalkyl.

6. A compound according to claim 1, wherein one of $R^2$ and $R^6$ is halogen or haloalkyl and the other one is hydrogen.

7. A compound according to claim 1, wherein one of $R^2$ and $R^6$ is chloro or trifluoromethyl and the other one is hydrogen.

8. A compound according to claim 1, wherein $R^3$ and $R^5$ are each independently selected from the group consisting of hydrogen, halogen and haloalkyl.

9. A compound according to claim 1, wherein $R^3$ and $R^5$ are each independently selected from the group consisting of hydrogen, chloro and trifluoromethyl.

10. A compound according to claim 1, wherein $R^3$ and $R^5$ are both hydrogen.

11. A compound according to claim 1, wherein $R^4$ is selected from the group consisting of hydrogen, hydroxyl, halogen, cyanopyrazinyloxy, alkylpiperazinyl, hexahydropyrrolo[1,2-a]pyrazinyl, haloalkoxy, pyrazolyl, cycloalkylpiperazinyl, imidazolyl and alkoxyalkoxy.

12. A compound according to claim 1, wherein $R^4$ is selected from the group consisting of hydrogen, halogen, alkylpiperazinyl, hexahydropyrrolo[1,2-a]pyrazinyl, haloalkoxy, pyrazolyl, cycloalkylpiperazinyl and alkoxyalkoxy.

13. A compound according to claim 1, wherein $R^4$ is selected from the group consisting of hydrogen, halogen, methylpiperazinyl, tert-butylpiperazinyl, hexahydropyrrolo[1,2-a]pyrazinyl, trifluoroethyloxy, trifluoropropyloxy, pyrazolyl, cyclopropylpiperazinyl and methoxyethoxy.

14. A compound according to claim 1, wherein $A^1$ is absent or carbonyl.

15. A compound according to claim 1, wherein $A^2$ is $CR^7$.

16. A compound according to claim 1, wherein $A^3$ is $CR^8$.

17. A compound according to claim 1, wherein $A^4$ is nitrogen.

18. A compound according to claim 1, wherein $R^7$ is hydrogen.

19. A compound according to claim 1, wherein $R^8$ is hydrogen, alkyl or haloalkyl.

20. A compound according to claim 1, wherein $R^8$ is trifluoromethyl.

21. A compound according to claim 1, wherein $R^9$ is hydrogen.

22. A compound according to claim 1 selected from the group consisting of:
- 6-[(2S,4S)-4-(2-Chloro-benzenesulfonyl)-2-(morpholine-4-carbonyl)-pyrrolidin-1-yl]-pyrazine-2-carbonitrile;
- (2S,4S)-4-(2-Chloro-benzenesulfonyl)-1-(6-cyano-pyrazin-2-yl)-pyrrolidine-2-carboxylic acid methyl ester;
- 6-[3-(4-Hydroxy-benzenesulfonyl)-pyrrolidin-1-yl]-pyrazine-2-carbonitrile;
- 6-[3-({4-[(6-cyanopyrazin-2-yl)oxy]phenyl}sulfonyl)pyrrolidin-1-yl]pyrazine-2-carbonitrile;
- (2S,4S)-4-(2-chloro-benzenesulfonyl)-1-(6-cyano-pyrazin-2-yl)-pyrrolidine-2-carboxylic acid;
- (2S,4S)-4-(2-Chloro-benzenesulfonyl)-1-(6-cyano-pyrazin-2-yl)-pyrrolidine-2-carboxylic acid (2,2,2-trifluoro-ethyl)-amide;
- (2R,4S)-4-(2-Chloro-benzenesulfonyl)-1-(6-cyano-pyrazin-2-yl)-pyrrolidine-2-carboxylic acid ethyl ester;
- 6-[(S)-3-(2-Chloro-benzenesulfonyl)-pyrrolidin-1-yl]-pyridine-2-carbonitrile;
- 6-[(S)-3-(2-Chloro-benzenesulfonyl)-pyrrolidin-1-yl]-pyrazine-2-carbonitrile; and
- 6-[(2R,4S)-4-(2-Chloro-benzenesulfonyl)-2-(morpholine-4-carbonyl)-pyrrolidin-1-yl]-pyrazine-2-carbonitrile.

23. A compound according to claim 1 selected from the group consisting of:
- (2R,4S)-4-(2-Chloro-benzenesulfonyl)-1-(6-cyano-pyrazin-2-yl)-pyrrolidine-2-carboxylic acid (2,2,2-trifluoro-ethyl)-amide;
- 4-[(S)-3-(2-Chloro-benzenesulfonyl)-pyrrolidin-1-yl]-pyrimidine-2-carbonitrile;
- 4-[(2R,4S)-4-(2-Chloro-benzenesulfonyl)-2-(5-methyl-[1,3,4]oxadiazol-2-yl)-pyrrolidin-1-yl]-pyrimidine-2-carbonitrile;
- 4-[(S)-3-(2-Trifluoromethyl-benzenesulfonyl)-pyrrolidin-1-yl]-pyrimidine-2-carbonitrile;
- 4-[(2R,4S)-2-Hydroxymethyl-4-(2-trifluoromethyl-benzenesulfonyl)-pyrrolidin-1-yl]-pyrimidine-2-carbonitrile;
- 4-Methyl-6-[(S)-3-(2-trifluoromethyl-benzenesulfonyl)-pyrrolidin-1-yl]-pyrimidine-2-carbonitrile;
- 5-Trifluoromethyl-4-[(S)-3-(2-trifluoromethyl-benzenesulfonyl)-pyrrolidin-1-yl]-pyrimidine-2-carbonitrile;
- 5-Fluoro-4-[(S)-3-(2-trifluoromethyl-benzenesulfonyl)-pyrrolidin-1-yl]-pyrimidine-2-carbonitrile;
- 5-Hydroxy-4-[(S)-3-(2-trifluoromethyl-benzenesulfonyl)-pyrrolidin-1-yl]-pyrimidine-2-carbonitrile; and
- 4-[(2R,4S)-2-Morpholin-4-ylmethyl-4-(2-trifluoromethyl-benzenesulfonyl)-pyrrolidin-1-yl]-pyrimidine-2-carbonitrile.

24. A compound according to claim 1 selected from the group consisting of:
- 2-[(2R,4S)-2-Morpholin-4-ylmethyl-4-(2-trifluoromethyl-benzenesulfonyl)-pyrrolidin-1-yl]-pyrimidine-4-carbonitrile;
- 4-[(2R,4S)-2-(3,3-Difluoro-pyrrolidin-1-ylmethyl)-4-(2-trifluoromethyl-benzenesulfonyl)-pyrrolidin-1-yl]-pyrimidine-2-carbonitrile;
- 4-[(S)-3-(2,3-Dichloro-benzenesulfonyl)-pyrrolidin-1-yl]-pyrimidine-2-carbonitrile;
- 4-[(R)-3-(2-Bromo-benzenesulfonyl)-pyrrolidin-1-yl]-pyrimidine-2-carbonitrile;
- 4-[(S)-3-(3-Trifluoromethyl-benzenesulfonyl)-pyrrolidin-1-yl]-pyrimidine-2-carbonitrile;
- (2S,4S)-1-(2-Cyano-pyrimidin-4-yl)-4-(2-trifluoromethyl-benzenesulfonyl)-pyrrolidine-2-carboxylic acid (2,2,2-trifluoro-ethyl)-amide;
- 4-[(2S,4S)-2-(Azetidine-1-carbonyl)-4-(2-trifluoromethyl-benzenesulfonyl)-pyrrolidin-1-yl]-pyrimidine-2-carbonitrile;
- (2S,4S)-1-(2-Cyano-pyrimidin-4-yl)-4-(2-trifluoromethyl-benzenesulfonyl)-pyrrolidine-2-carboxylic acid ((S)-2,2,2-trifluoro-1-methyl-ethyl)-amide;
- (2S,4S)-1-(2-Cyano-pyrimidin-4-yl)-4-(2-trifluoromethyl-benzenesulfonyl)-pyrrolidine-2-carboxylic acid diethylamide; and
- (2S,4S)-1-(2-Cyano-pyrimidin-4-yl)-4-(2-trifluoromethyl-benzenesulfonyl)-pyrrolidine-2-carboxylic acid.

25. A compound according to claim 1 selected from the group consisting of:
- (2S,4S)-1-(2-Cyano-pyrimidin-4-yl)-4-(2-trifluoromethyl-benzenesulfonyl)-pyrrolidine-2-carboxylic acid amide;
- (2S,4S)-1-(2-Cyano-pyrimidin-4-yl)-4-(2-trifluoromethyl-benzenesulfonyl)-pyrrolidine-2-carboxylic acid ethylamide;

(2S,4S)-1-(2-Cyano-pyrimidin-4-yl)-4-(2-trifluoromethyl-benzenesulfonyl)-pyrrolidine-2-carboxylic acid cyanomethyl-amide;

4-[(2S,4S)-2-(3,3-Difluoro-pyrrolidine-1-carbonyl)-4-(2-trifluoromethyl-benzenesulfonyl)-pyrrolidin-1-yl]-pyrimidine-2-carbonitrile;

(2S,4S)-1-(2-Cyano-pyrimidin-4-yl)-4-(2-trifluoromethyl-benzenesulfonyl)-pyrrolidine-2-carboxylic acid 4-fluoro-benzylamide;

(2S,4S)-1-(2-Cyano-pyrimidin-4-yl)-4-(2-trifluoromethyl-benzenesulfonyl)-pyrrolidine-2-carboxylic acid (1-cyano-cyclopropyl)-amide;

(2S,4S)-1-(2-Cyano-pyrimidin-4-yl)-4-(2-trifluoromethyl-benzenesulfonyl)-pyrrolidine-2-carboxylic acid isopropylamide;

4-[(S)-3-(2-Trifluoromethyl-benzenesulfonyl)-pyrrolidin-1-yl]-6,7-dihydro-5H-cyclopentapyrimidine-2-carbonitrile;

5-Methyl-4-[(S)-3-(2-trifluoromethyl-benzenesulfonyl)-pyrrolidin-1-yl]-pyrimidine-2-carbonitrile; and 4-Trifluoromethyl-6-[(S)-3-(2-trifluoromethyl-benzenesulfonyl)-pyrrolidin-1-yl]-pyrimidine-2-carbonitrile.

26. A compound according to claim 1 selected from the group consisting of:

(S)-1-(2-Cyano-6-trifluoromethyl-pyrimidin-4-yl)-4-(2-trifluoromethyl-benzenesulfonyl)-pyrrolidine-2-carboxylic acid amide;

4-[(S)-3-(2-Chloro-4-fluoro-benzenesulfonyl)-pyrrolidin-1-yl]-6-trifluoromethyl-pyrimidine-2-carbonitrile;

4-{(S)-3-[2-Chloro-4-(4-methyl-piperazin-1-yl)-benzenesulfonyl]-pyrrolidin-1-yl}-6-trifluoromethyl-pyrimidine-2-carbonitrile;

4-{(S)-3-[4-(4-tert-Butyl-piperazin-1-yl)-2-chloro-benzenesulfonyl]-pyrrolidin-1-yl}-6-trifluoromethyl-pyrimidine-2-carbonitrile;

4-[(S)-3-((S)-2-Chloro-4-hexahydro-pyrrolo[1,2-a]pyrazin-2-yl-benzenesulfonyl)-pyrrolidin-1-yl]-6-trifluoromethyl-pyrimidine-2-carbonitrile;

4-{(S)-3-[2-Chloro-4-((S)-2,2,2-trifluoro-1-methyl-ethoxy)-benzenesulfonyl]-pyrrolidin-1-yl}-6-trifluoromethyl-pyrimidine-2-carbonitrile;

4-[(S)-3-(2-Chloro-4-pyrazol-1-yl-benzenesulfonyl)-pyrrolidin-1-yl]-6-trifluoromethyl-pyrimidine-2-carbonitrile;

4-{(S)-3-[2-Chloro-4-(4-cyclopropyl-piperazin-1-yl)-benzenesulfonyl]-pyrrolidin-1-yl}-6-trifluoromethyl-pyrimidine-2-carbonitrile;

4-{(S)-3-[2-Chloro-4-(2,2,2-trifluoro-ethoxy)-benzenesulfonyl]-pyrrolidin-1-yl}-6-trifluoromethyl-pyrimidine-2-carbonitrile; and 4-[(S)-3-(2-Chloro-4-imidazol-1-yl-benzenesulfonyl)-pyrrolidin-1-yl]-6-trifluoromethyl-pyrimidine-2-carbonitrile.

27. A compound according to claim 1 selected from the group consisting of:

4-{(S)-3-[2-Chloro-4-(2-methoxy-ethoxy)-benzenesulfonyl]-pyrrolidin-1-yl}-6-trifluoromethyl-pyrimidine-2-carbonitrile;

4-[(S)-3-(2-Chloro-4-fluoro-benzenesulfonyl)-pyrrolidin-1-yl]-2-cyano-pyrimidine-5-carboxylic acid (2,2,2-trifluoro-ethyl)-amide;

4-{(S)-3-[4-(4-tert-Butyl-piperazin-1-yl)-2-chloro-benzenesulfonyl]-pyrrolidin-1-yl}-2-cyano-pyrimidine-5-carboxylic acid (2,2,2-trifluoro-ethyl)-amide;

4-{(S)-3-[2-Chloro-4-(2,2,2-trifluoro-ethoxy)-benzenesulfonyl]-pyrrolidin-1-yl}-2-cyano-pyrimidine-5-carboxylic acid (2,2,2-trifluoro-ethyl)-amide;

4-{(S)-3-[2-Chloro-4-(4-cyclopropyl-piperazin-1-yl)-benzenesulfonyl]-pyrrolidin-1-yl}-2-cyano-pyrimidine-5-carboxylic acid (2,2,2-trifluoro-ethyl)-amide;

4-[(S)-3-(2-Chloro-4-imidazol-1-yl-benzenesulfonyl)-pyrrolidin-1-yl]-2-cyano-pyrimidine-5-carboxylic acid (2,2,2-trifluoro-ethyl)-amide;

4-{(S)-3-[4-(4-tert-Butyl-piperazin-1-yl)-2-chloro-benzenesulfonyl]-pyrrolidin-1-yl}-2-cyano-pyrimidine-5-carboxylic acid [2-(4-chloro-phenyl)-propyl]-amide;

4-{(S)-3-[2-Chloro-4-(2,2,2-trifluoro-ethoxy)-benzenesulfonyl]-pyrrolidin-1-yl}-6-(2,2,2-trifluoro-ethyl)-6,7-dihydro-5H-pyrrolo[3,4-d]pyrimidine-2-carbonitrile;

4-[(S)-3-(2-Chloro-4-pyrazol-1-yl-benzenesulfonyl)-pyrrolidin-1-yl]-6-(2,2,2-trifluoro-ethyl)-6,7-dihydro-5H-pyrrolo[3,4-d]pyrimidine-2-carbonitrile; and 4-[(S)-3-(2-Chloro-4-pyrazol-1-yl-benzenesulfonyl)-pyrrolidin-1-yl]-6-formyl-6,7-dihydro-5H-pyrrolo[3,4-d]pyrimidine-2-carbonitrile.

28. A compound according to claim 1 selected from the group consisting of:

6-[(S)-3-((S)-2-Chloro-4-hexahydro-pyrrolo[1,2-a]pyrazin-2-yl-benzenesulfonyl)-pyrrolidin-1-yl]-pyridine-2-carbonitrile; compound with formic acid;

6-[(S)-3-((S)-2-Chloro-4-hexahydro-pyrrolo[1,2-a]pyrazin-2-yl-benzenesulfonyl)-pyrrolidin-1-yl]-pyrazine-2-carbonitrile; compound with formic acid;

2-[(S)-3-((S)-2-Chloro-4-hexahydro-pyrrolo[1,2-a]pyrazin-2-yl-benzenesulfonyl)-pyrrolidin-1-yl]-pyrimidine-4-carbonitrile; compound with formic acid;

6-[3-((S)-2-Chloro-4-hexahydro-pyrrolo[1,2-a]pyrazin-2-yl-benzenesulfonyl)-pyrrolidin-1-yl]-3-nitro-pyridine-2-carbonitrileformic acid;

(S)-6-(3-(2-(trifluoromethyl)phenylsulfonyl)pyrrolidin-1-yl)picolinonitrile;

(S)-2-(3-(2-(trifluoromethyl)phenylsulfonyl)pyrrolidin-1-yl)pyrimidine-4-carbonitrile;

(S)-6-(3-(2-(trifluoromethyl)phenylsulfonyl)pyrrolidin-1-yl)pyrazine-2-carbonitrile;

6-((S)-3-{2-Chloro-4-[4-(2-methoxy-ethyl)-piperazin-1-yl]-benzenesulfonyl}-pyrrolidin-1-yl)-pyrazine-2-carbonitrile;

2-((S)-3-{2-Chloro-4-[4-(2-methoxy-ethyl)-piperazin-1-yl]-benzenesulfonyl}-pyrrolidin-1-yl)-pyrimidine-4-carbonitrile; and 6-((S)-3-{2-Chloro-4-[4-(2-methoxy-ethyl)-piperazin-1-yl]-benzenesulfonyl}-pyrrolidin-1-yl)-pyridine-2-carbonitrile.

29. A compound according to claim 1 selected from the group consisting of:

6-((S)-3-{2-Chloro-4-[4-(2-methoxy-ethyl)-piperazin-1-yl]-benzenesulfonyl}-pyrrolidin-1-yl)-3-nitro-pyridine-2-carbonitrile;

(S)-6-(3-(2-chloro-4-fluorophenylsulfonyl)pyrrolidin-1-yl)picolinonitrile;

(S)-2-(3-(2-chloro-4-fluorophenylsulfonyl)pyrrolidin-1-yl)pyrimidine-4-carbonitrile;

(S)-6-(3-(2-chloro-4-fluorophenylsulfonyl)pyrrolidin-1-yl)pyrazine-2-carbonitrile;

(S)-2-(3-(2-chloro-4-(4-methylpiperazin-1-yl)phenylsulfonyl)pyrrolidin-1-yl)pyrimidine-4-carbonitrile;

(S)-6-(3-(2-chloro-4-(4-methylpiperazin-1-yl)phenylsulfonyl)pyrrolidin-1-yl)pyrazine-2-carbonitrile;

2-Cyano-4-[(S)-3-(2-trifluoromethyl-benzenesulfonyl)-pyrrolidin-1-yl]-pyrimidine-5-carboxylic acid (2-phenyl-cyclopropyl)-amide;

2-Cyano-4-[(S)-3-(2-trifluoromethyl-benzenesulfonyl)-pyrrolidin-1-yl]-pyrimidine-5-carboxylic acid [2-(4-chloro-phenyl)-propyl]-amide;

2-Cyano-4-[(S)-3-(2-trifluoromethyl-benzenesulfonyl)-pyrrolidin-1-yl]-pyrimidine-5-carboxylic acid 4-trifluoromethyl-benzylamide; and 2-Cyano-4-[(S)-3-(2,3-dichloro-benzenesulfonyl)-pyrrolidin-1-yl]-pyrimidine-5-carboxylic acid 4-trifluoromethyl-benzylamide.

30. A compound according to claim 1 selected from the group consisting of:

2-Cyano-4-[(S)-3-(2-trifluoromethyl-benzenesulfonyl)-pyrrolidin-1-yl]-pyrimidine-5-carboxylic acid [1-(4-fluoro-phenyl)-cyclopropyl]-amide;

2-Cyano-4-[(S)-3-(2,3-dichloro-benzenesulfonyl)-pyrrolidin-1-yl]-pyrimidine-5-carboxylic acid [1-(4-fluoro-phenyl)-cyclopropyl]-amide;

2-Cyano-4-[(S)-3-(2-trifluoromethyl-benzenesulfonyl)-pyrrolidin-1-yl]-pyrimidine-5-carboxylic acid (2,2,2-trifluoro-ethyl)-amide;

2-Cyano-4-[(S)-3-(2,3-dichloro-benzenesulfonyl)-pyrrolidin-1-yl]-pyrimidine-5-carboxylic acid (2,2,2-trifluoro-ethyl)-amide;

2-Cyano-4-[(S)-3-(2-trifluoromethyl-benzenesulfonyl)-pyrrolidin-1-yl]-pyrimidine-5-carboxylic acid [2-(4-chloro-phenyl)-propyl]-amide;

2-Cyano-4-[(S)-3-(2-trifluoromethyl-benzenesulfonyl)-pyrrolidin-1-yl]-pyrimidine-5-carboxylic acid [2-(4-chloro-phenyl)-propyl]-amide; and 2-Cyano-4-[(S)-3-(2-trifluoromethyl-benzenesulfonyl)-pyrrolidin-1-yl]-pyrimidine-5-carboxylic acid [1-(4-chloro-phenyl)-cyclopropylmethyl]-amide.

31. A compound according to claim 1 selected from

4-Trifluoromethyl-6-[(S)-3-(2-trifluoromethyl-benzenesulfonyl)-pyrrolidin-1-yl]-pyrimidine-2-carbonitrile;

(S)-1-(2-Cyano-6-trifluoromethyl-pyrimidin-4-yl)-4-(2-trifluoromethyl-benzenesulfonyl)-pyrrolidine-2-carboxylic acid amide;

4-{(S)-3-[2-Chloro-4-(4-methyl-piperazin-1-yl)-benzenesulfonyl]-pyrrolidin-1-yl}-6-trifluoromethyl-pyrimidine-2-carbonitrile;

4-{(S)-3-[4-(4-tert-Butyl-piperazin-1-yl)-2-chloro-benzenesulfonyl]-pyrrolidin-1-yl}-6-trifluoromethyl-pyrimidine-2-carbonitrile;

4-[(S)-3-((S)-2-Chloro-4-hexahydro-pyrrolo[1,2-a]pyrazin-2-yl-benzenesulfonyl)-pyrrolidin-1-yl]-6-trifluoromethyl-pyrimidine-2-carbonitrile;

4-{(S)-3-[2-Chloro-4-((S)-2,2,2-trifluoro-1-methyl-ethoxy)-benzenesulfonyl]-pyrrolidin-1-yl}-6-trifluoromethyl-pyrimidine-2-carbonitrile;

4-[(S)-3-(2-Chloro-4-pyrazol-1-yl-benzenesulfonyl)-pyrrolidin-1-yl]-6-trifluoromethyl-pyrimidine-2-carbonitrile;

4-{(S)-3-[2-Chloro-4-(4-cyclopropyl-piperazin-1-yl)-benzenesulfonyl]-pyrrolidin-1-yl}-6-trifluoromethyl-pyrimidine-2-carbonitrile;

4-{(S)-3-[2-Chloro-4-(2,2,2-trifluoro-ethoxy)-benzenesulfonyl]-pyrrolidin-1-yl}-6-trifluoromethyl-pyrimidine-2-carbonitrile; and 4-{(S)-3-[2-Chloro-4-(2-methoxy-ethoxy)-benzenesulfonyl]-pyrrolidin-1-yl}-6-trifluoromethyl-pyrimidine-2-carbonitrile.

32. A pharmaceutical composition comprising a compound according to claim 1 and a therapeutically inert carrier.

* * * * *